United States Patent [19]

Sprecker et al.

[11] Patent Number: 5,789,374
[45] Date of Patent: Aug. 4, 1998

[54] METHYL-SUBSTITUTED 1(2-NORBORNYL) ALKANOLS ACETATE ESTERS THEREOF AND PERFUMERY USES OF SAID ESTERS, AND PROCESS INTERMEDIATES FOR PRODUCING SAME

[75] Inventors: Mark A. Sprecker, Sea Bright; Richard A. Weiss, Livingston; Marie R. Hanna, Keyport, all of N.J.

[73] Assignee: International Flavors & Fragrances Inc., New York, N.Y.

[21] Appl. No.: 733,457

[22] Filed: Oct. 18, 1996

[51] Int. Cl.$^6$ .................................................. A61K 7/46
[52] U.S. Cl. .......................... 512/18; 512/14; 560/256; 568/820; 252/174.11; 252/8.6
[58] Field of Search .................... 512/18, 14; 560/256; 568/820, 374; 252/174.11, 8.6

[56] References Cited

U.S. PATENT DOCUMENTS

| | | | |
|---|---|---|---|
| 3,780,109 | 12/1973 | Schleppnik, III | 260/598 |
| 3,803,244 | 4/1974 | Schleppnik, II | 260/611 F |
| 3,942,761 | 3/1976 | Schleppnik, I | 252/522 |
| 4,076,853 | 2/1978 | Light et al. | 426/538 |
| 4,128,509 | 12/1978 | Schleppnik | 252/522 |
| 4,153,811 | 5/1979 | Light et al. | 568/820 |
| 4,390,464 | 6/1983 | Klemarczyk et al. | 512/6 |

OTHER PUBLICATIONS

Arctander, *Perfume and Flavor Chemicals (Aroma Chemicals)*, vol. I, monograph 1029 entitled "3,3–Dimethyl–Δ–2, β–Norbornane–2–Ethylacetate", (1969).
Schleppnik, IV, *Chemical Abstracts*, vol. 90:121081 (abstract of U.S. Patent No. 4,128,509), (1982).

*Primary Examiner*—James H. Reamer
*Attorney, Agent, or Firm*—Arthur L. Liberman

[57] ABSTRACT

Described are methyl-substituted 1(2-norbornyl) alkanols and acetate esters thereof defined according to the structures:

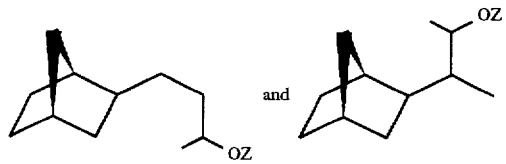

(wherein Z represents hydrogen or acetyl). The compounds wherein Z is acetyl, the esters, are useful in augmenting or enhancing the aroma of perfume compositions, colognes and perfumed articles, such as solid or liquid anionic, cationic, nonionic or zwitterionic detergents, fabric softeners, fabric softener articles, hair sprays, shampoos, bath oils and perfumed polymers. Also described are process intermediates for making such compounds defined according to the structures:

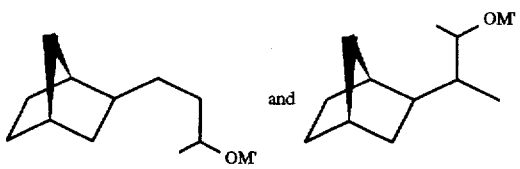

wherein M' represents MgX or Li and wherein X represents chloro, bromo or iodo.

30 Claims, 37 Drawing Sheets

GLC PROFILE FOR EXAMPLE I(A).

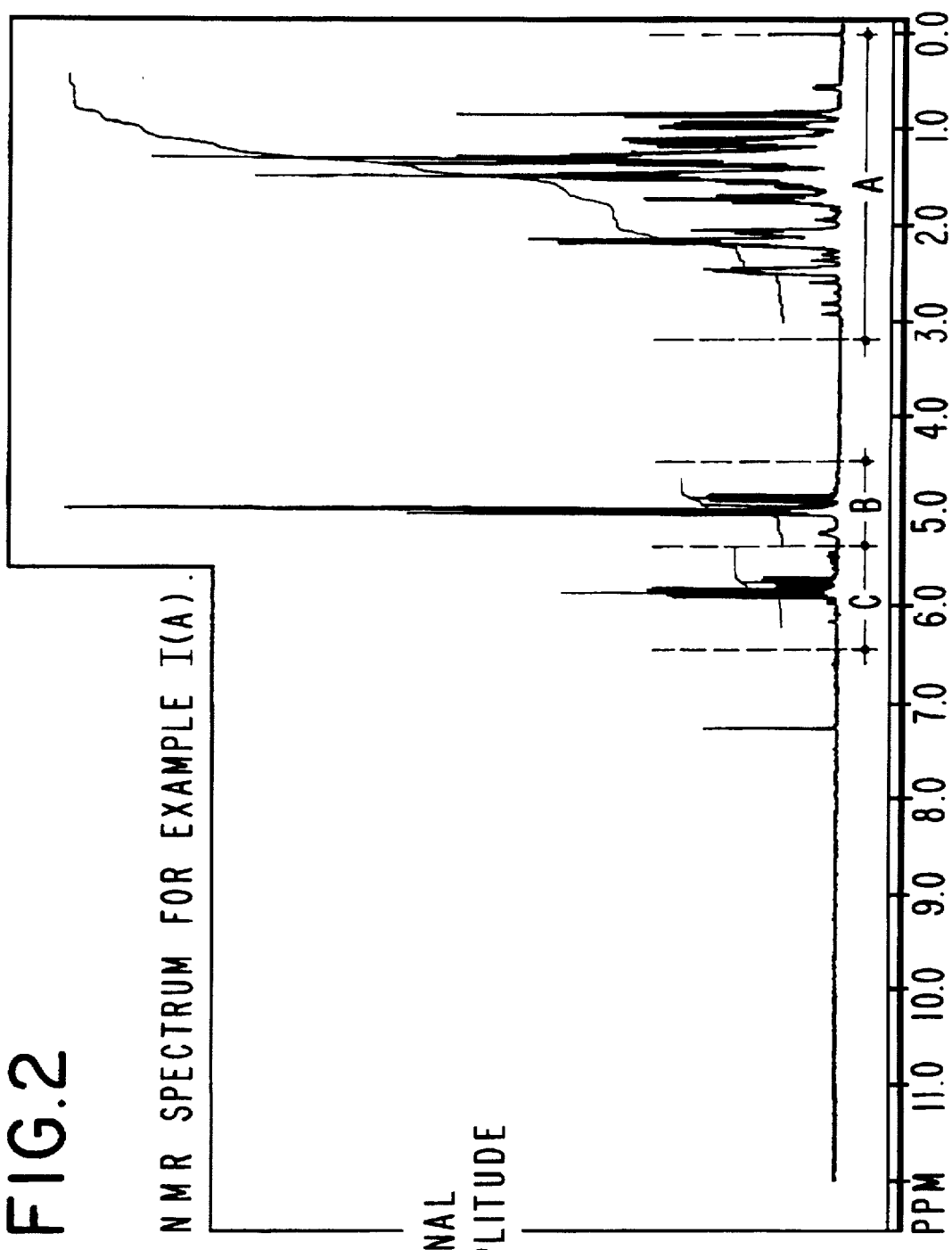

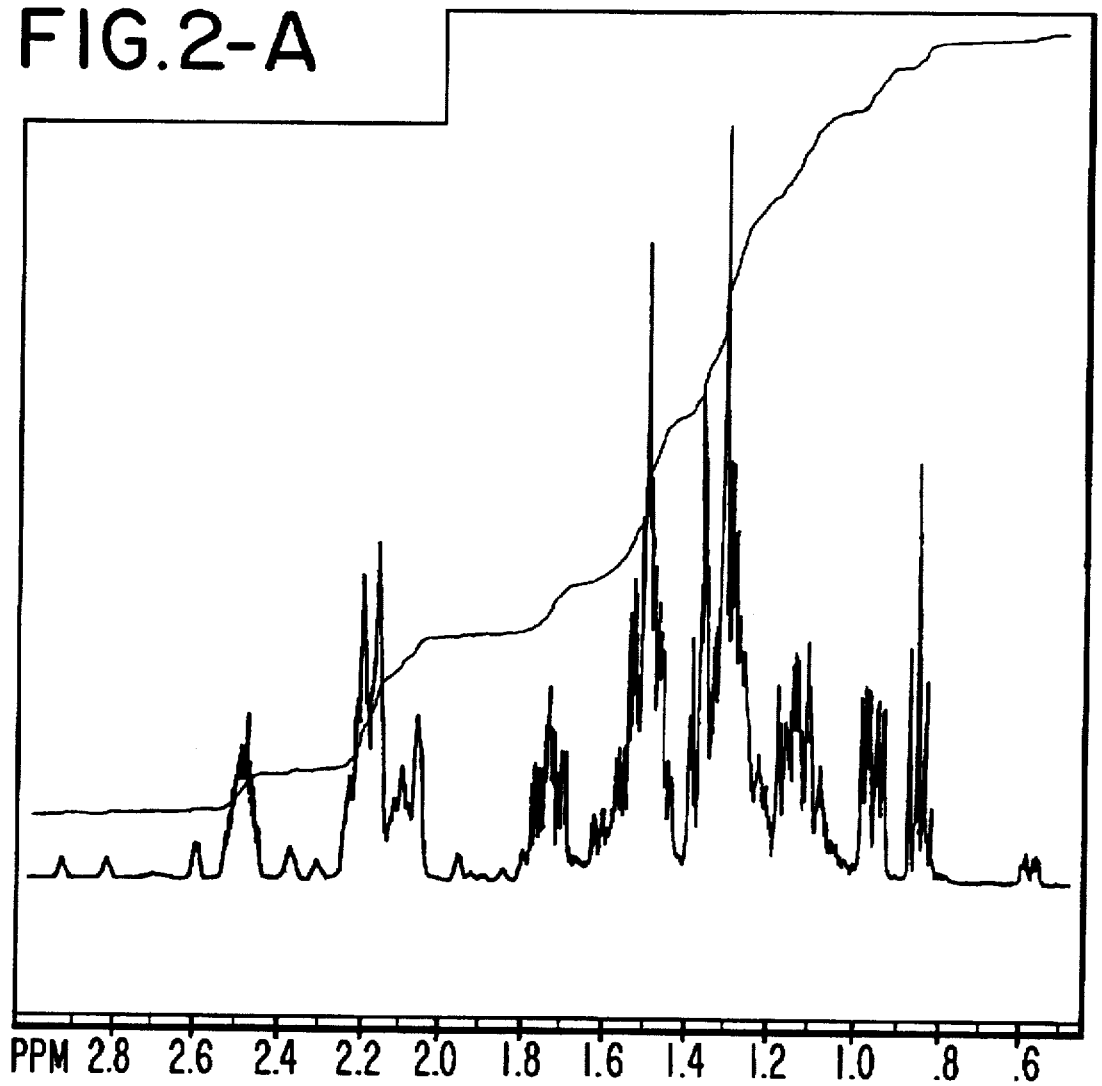
FIG.2-A

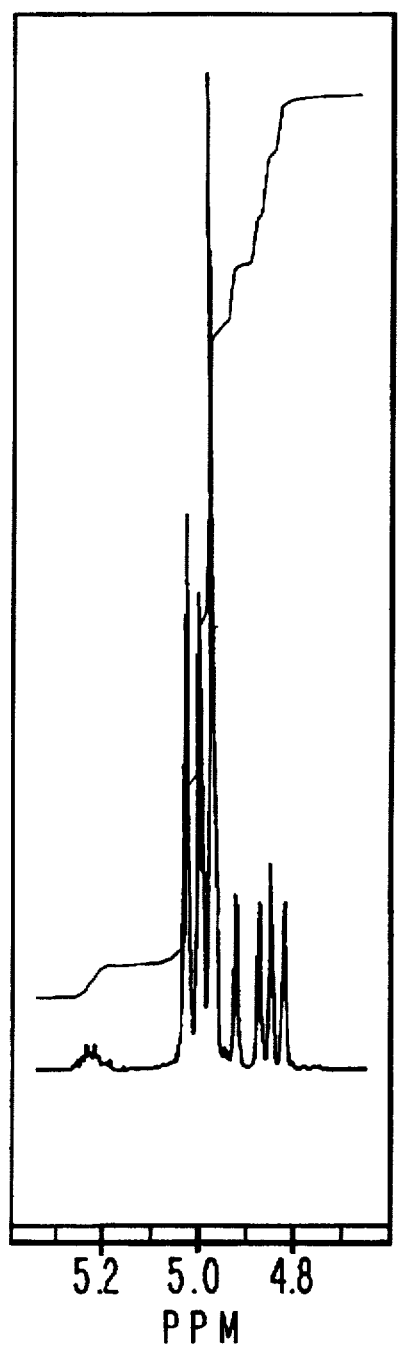
FIG.2-B

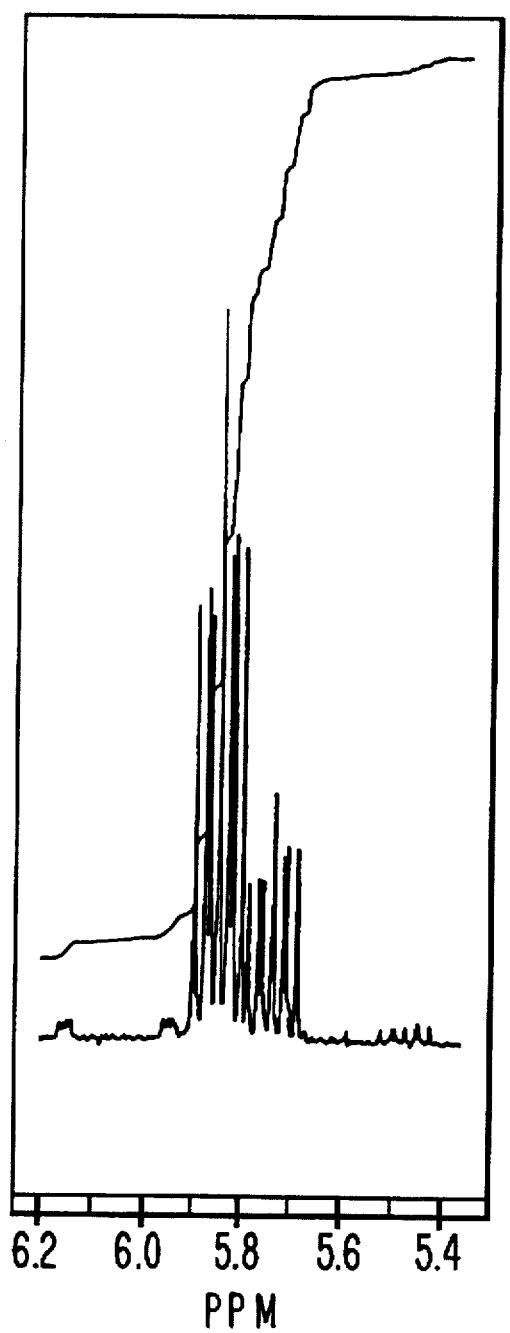
FIG.2-C

GLC PROFILE FOR EXAMPLE I(A).

NMR SPECTRUM FOR EXAMPLE I(A).

FIG. 4-A
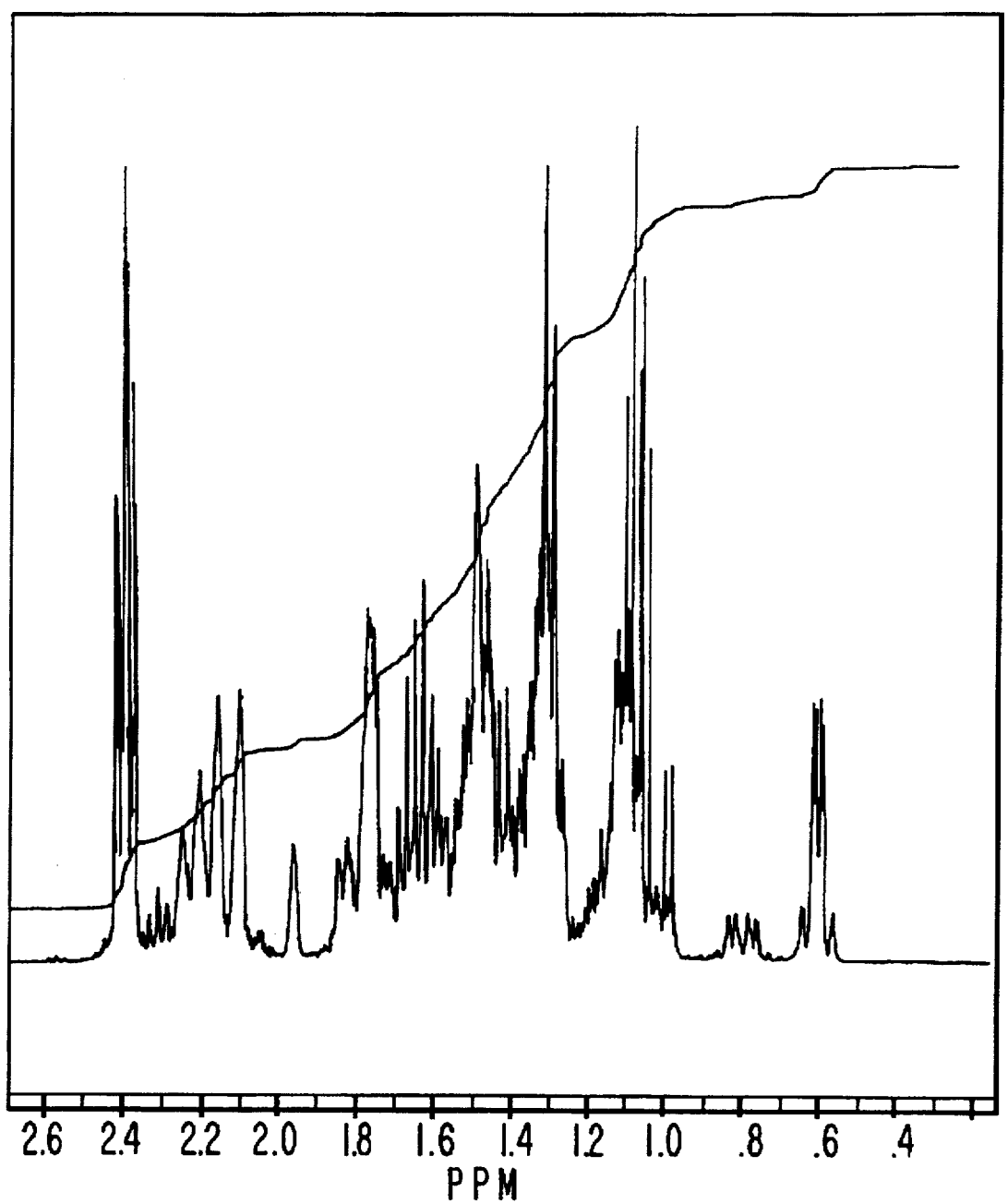

FIG.4-C
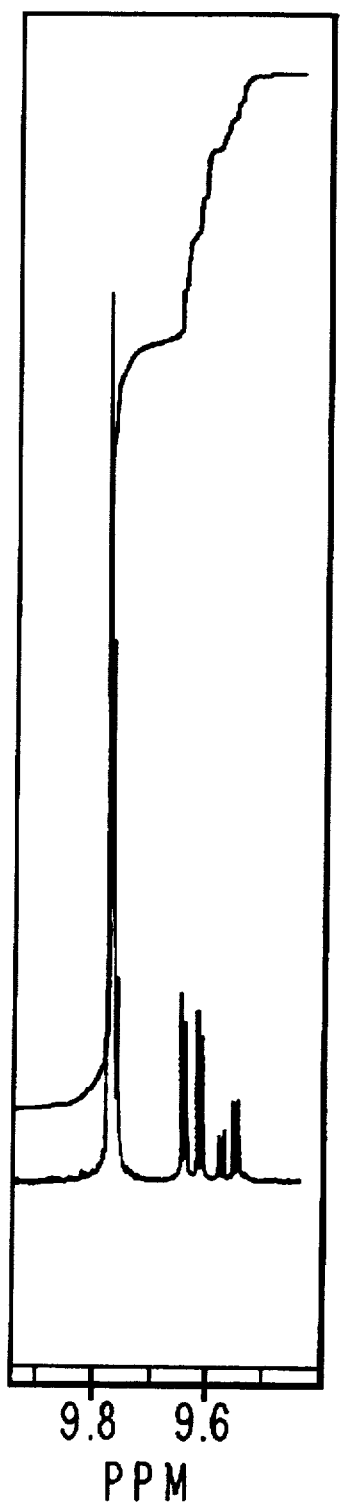
FIG.4-B
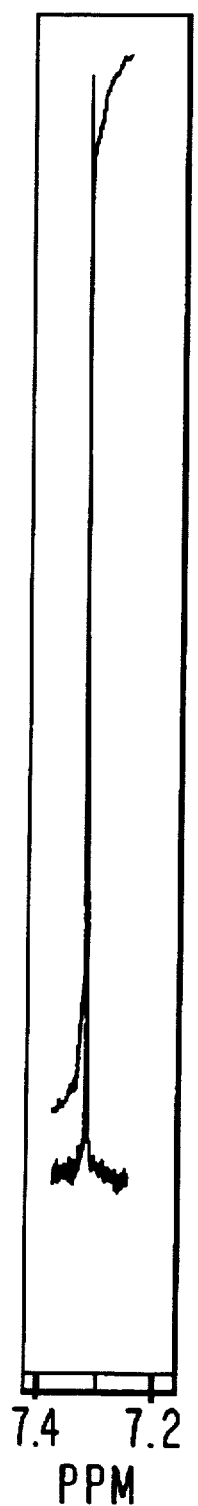

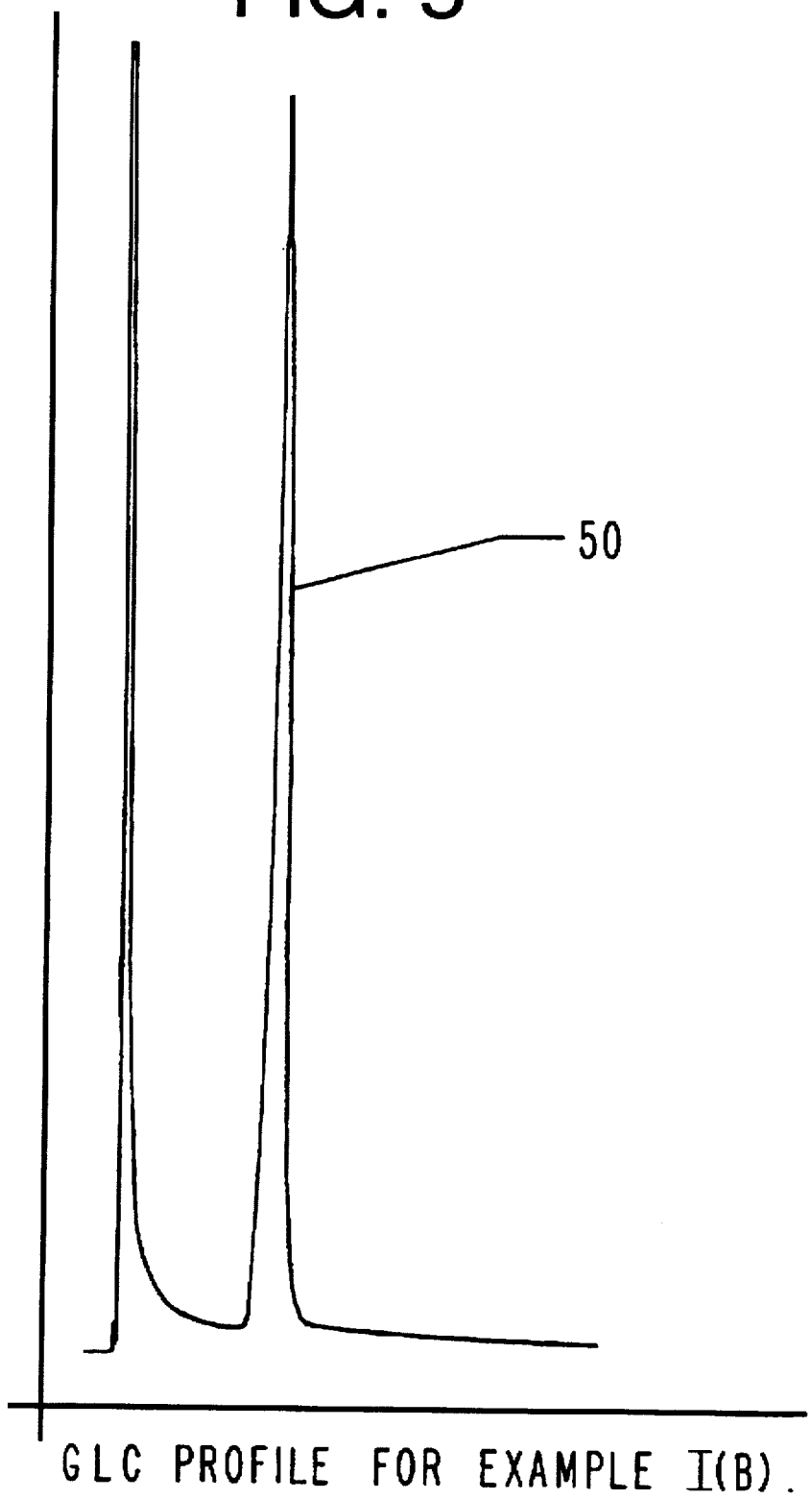

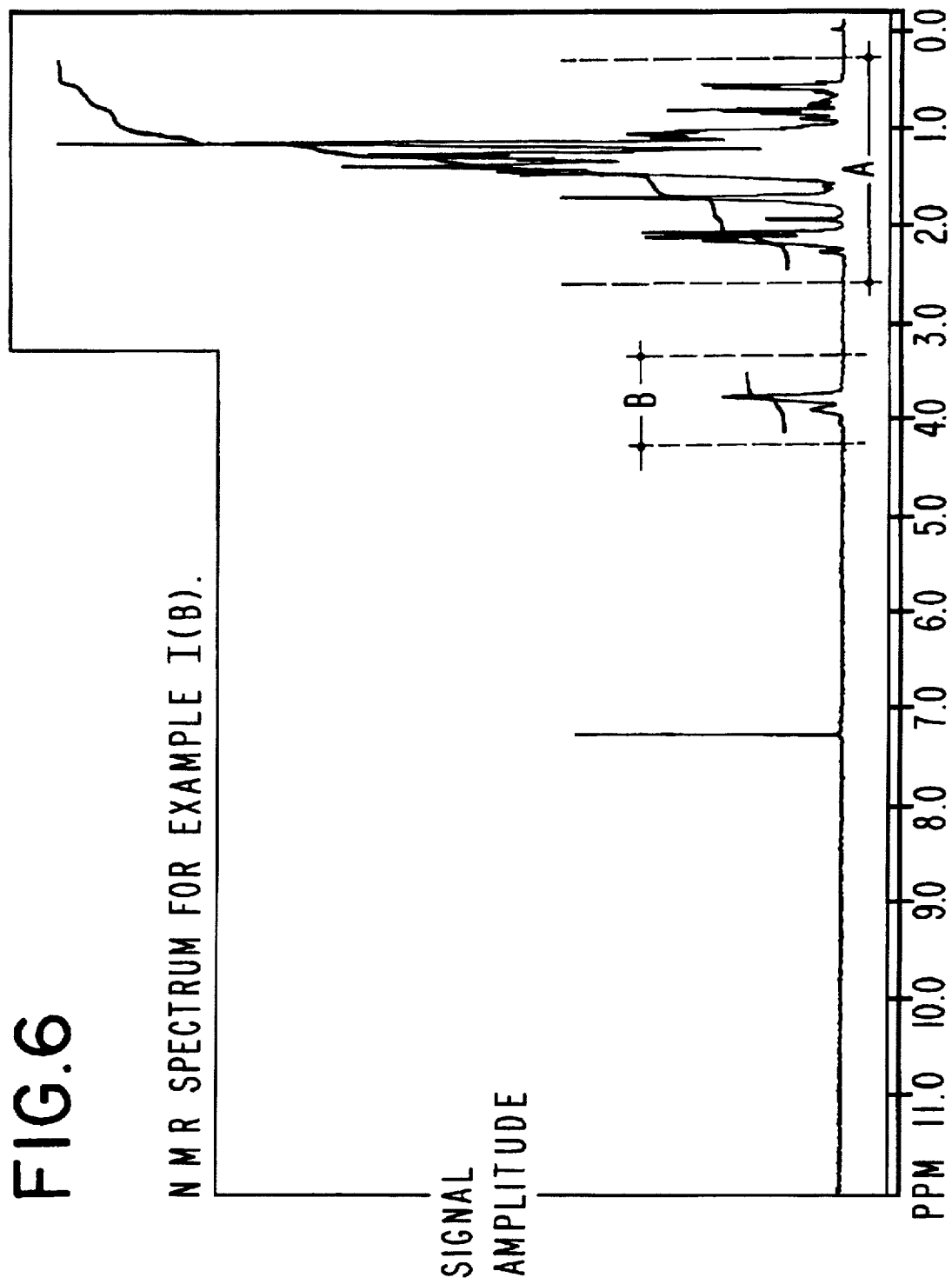

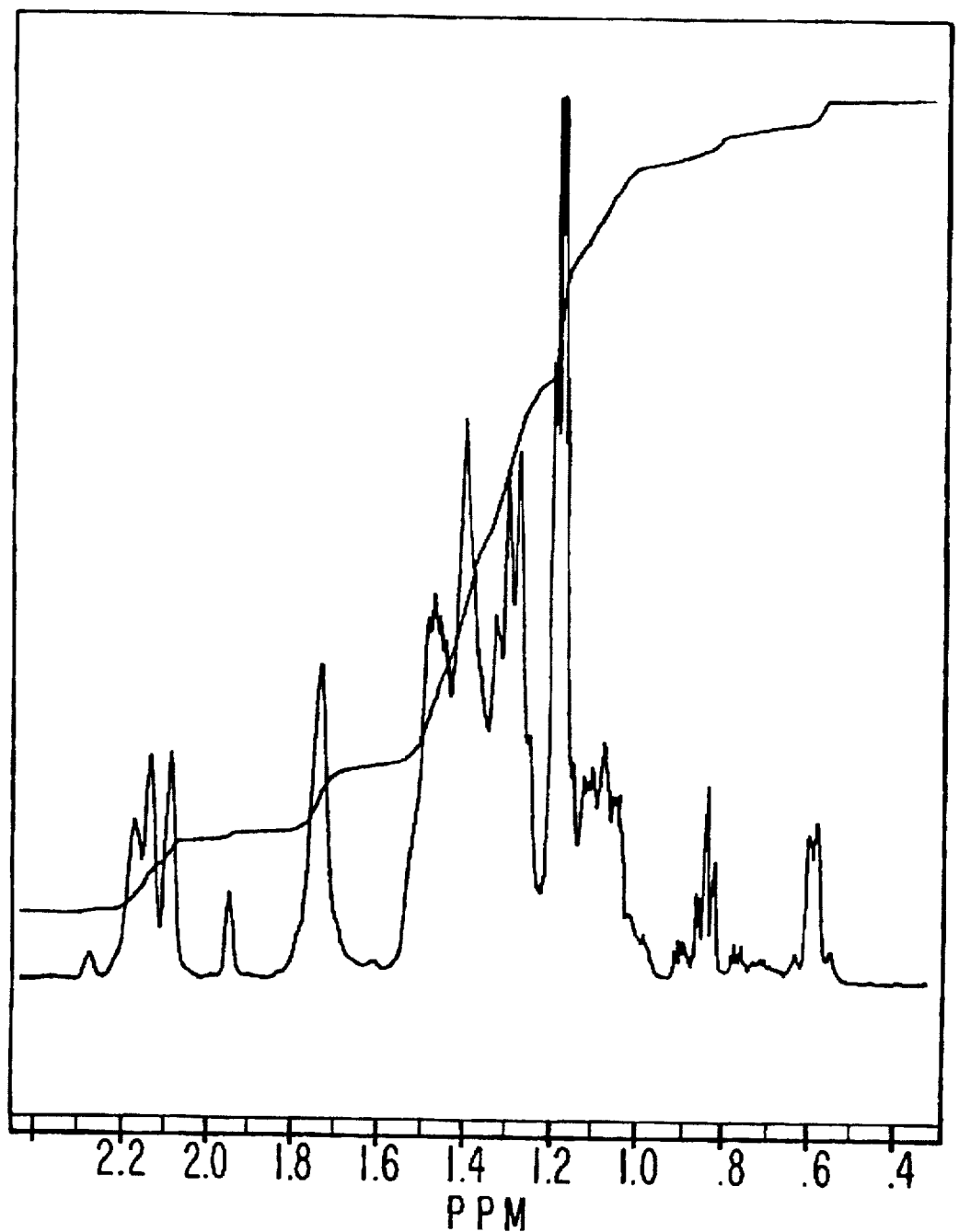
FIG.6-A

FIG.6-B
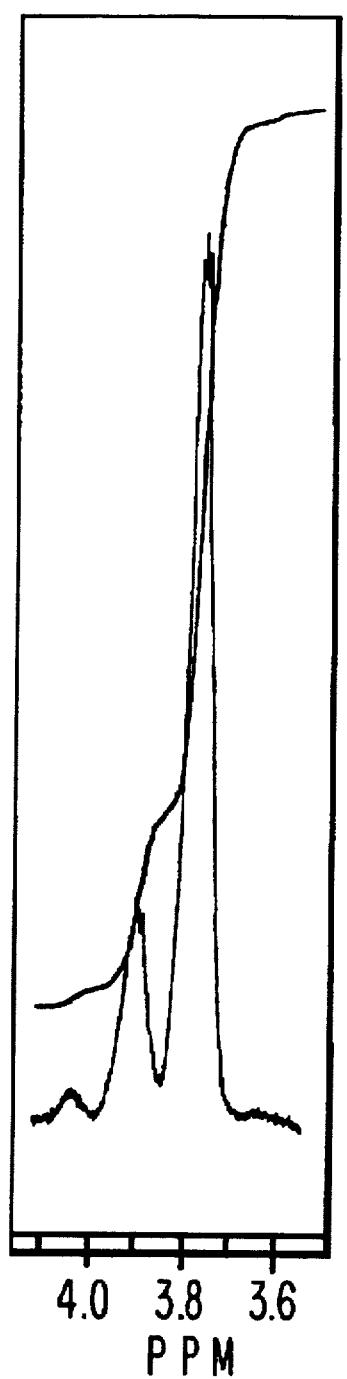

GLC PROFILE FOR EXAMPLE I(C).

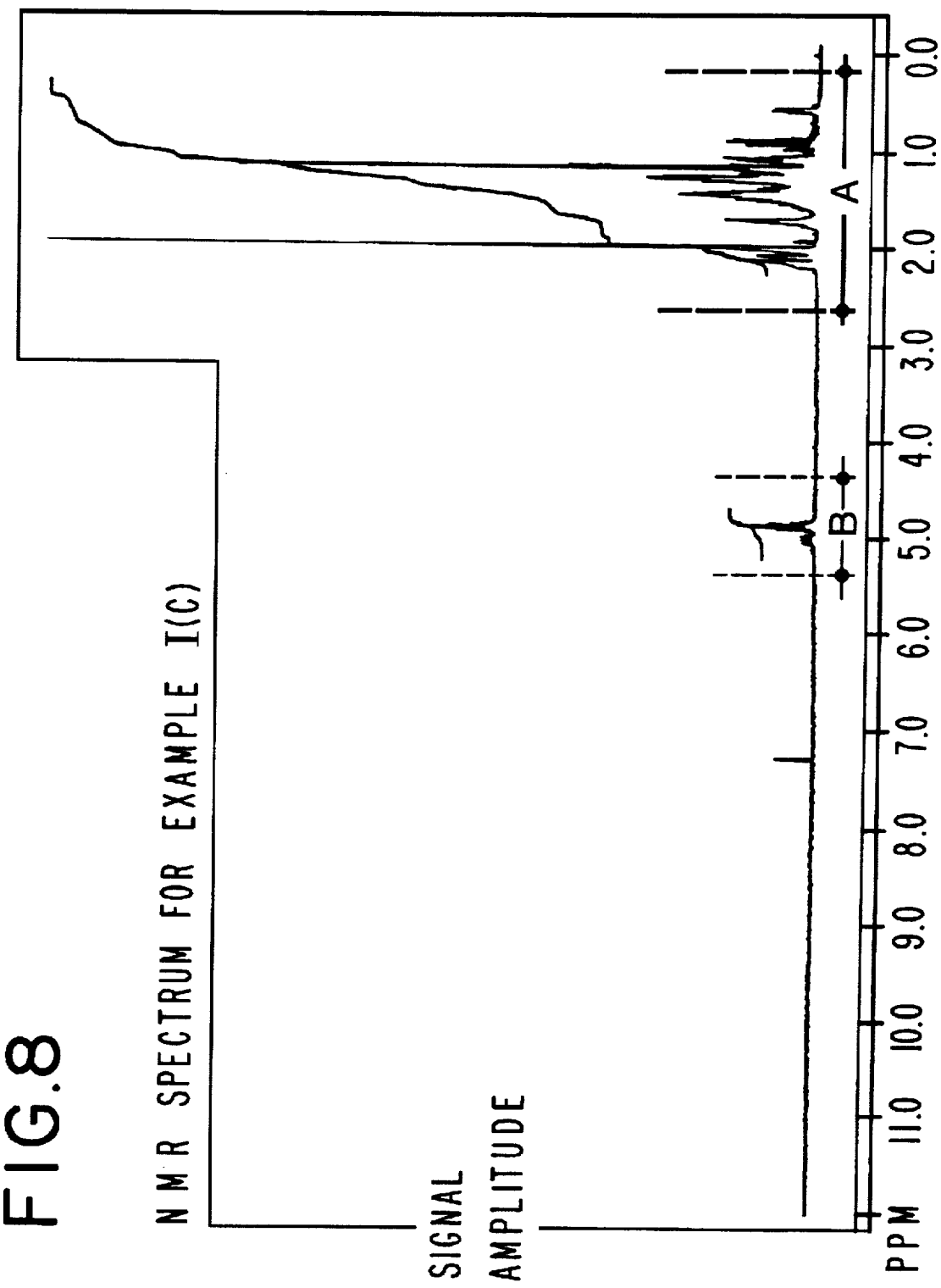

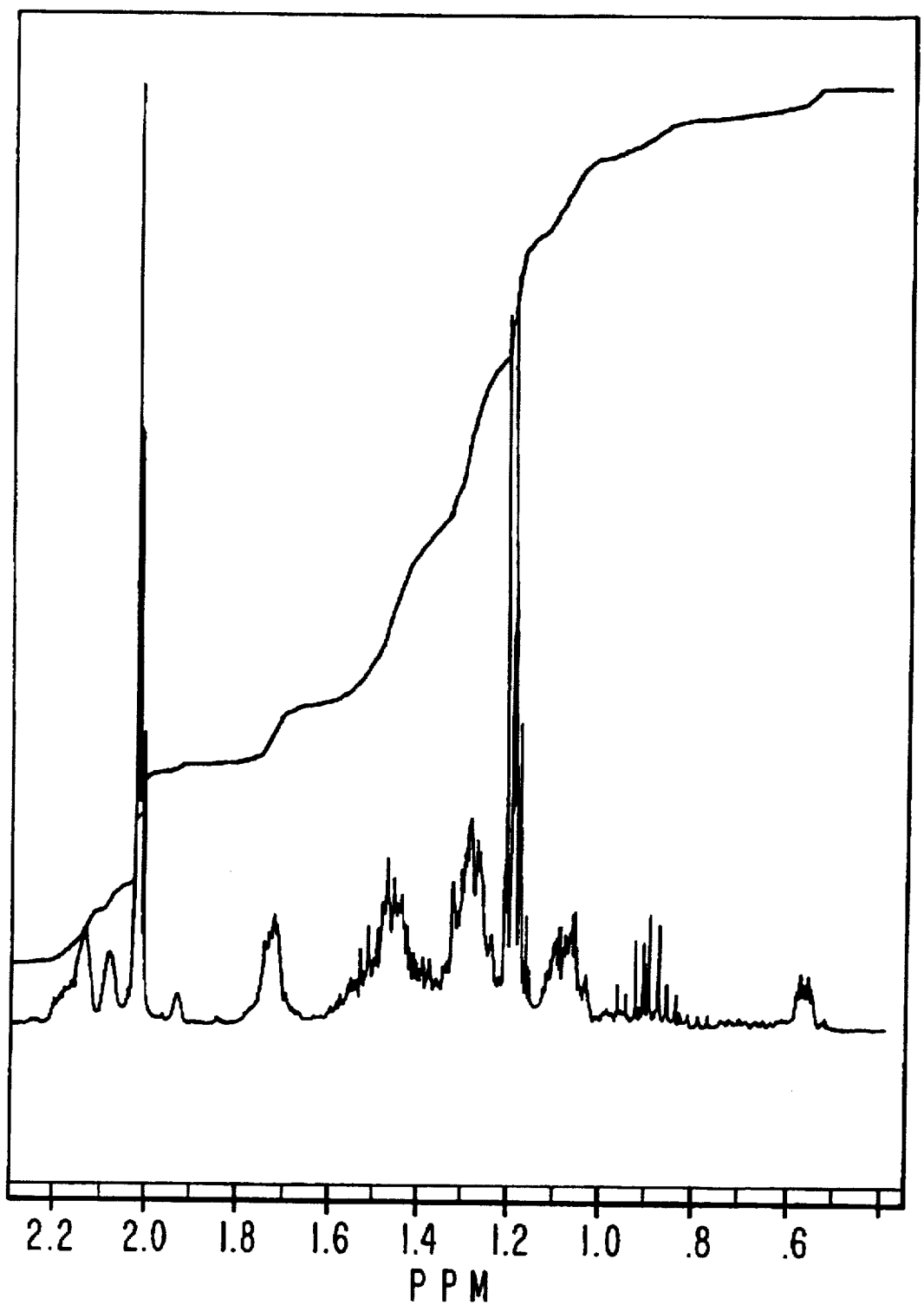
FIG. 8-A

FIG.8-B
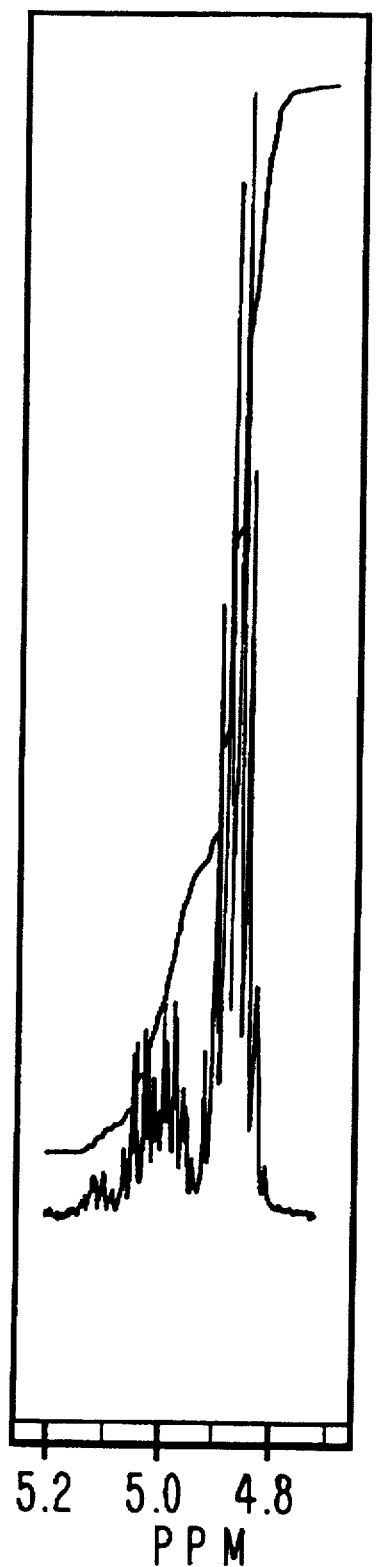

GLC PROFILE FOR EXAMPLE II(A). CRUDE.

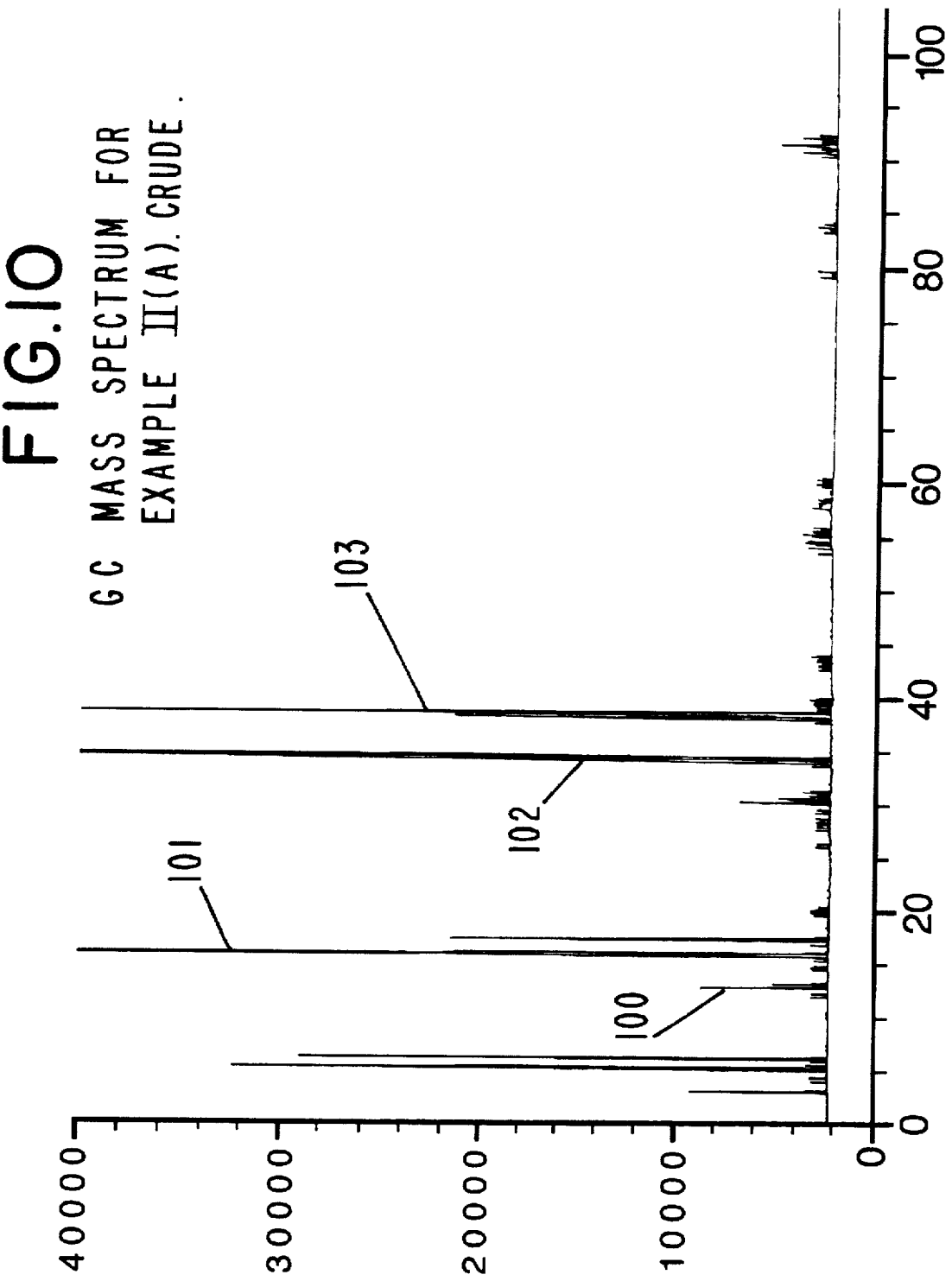
FIG. 10 GC MASS SPECTRUM FOR EXAMPLE II(A). CRUDE.

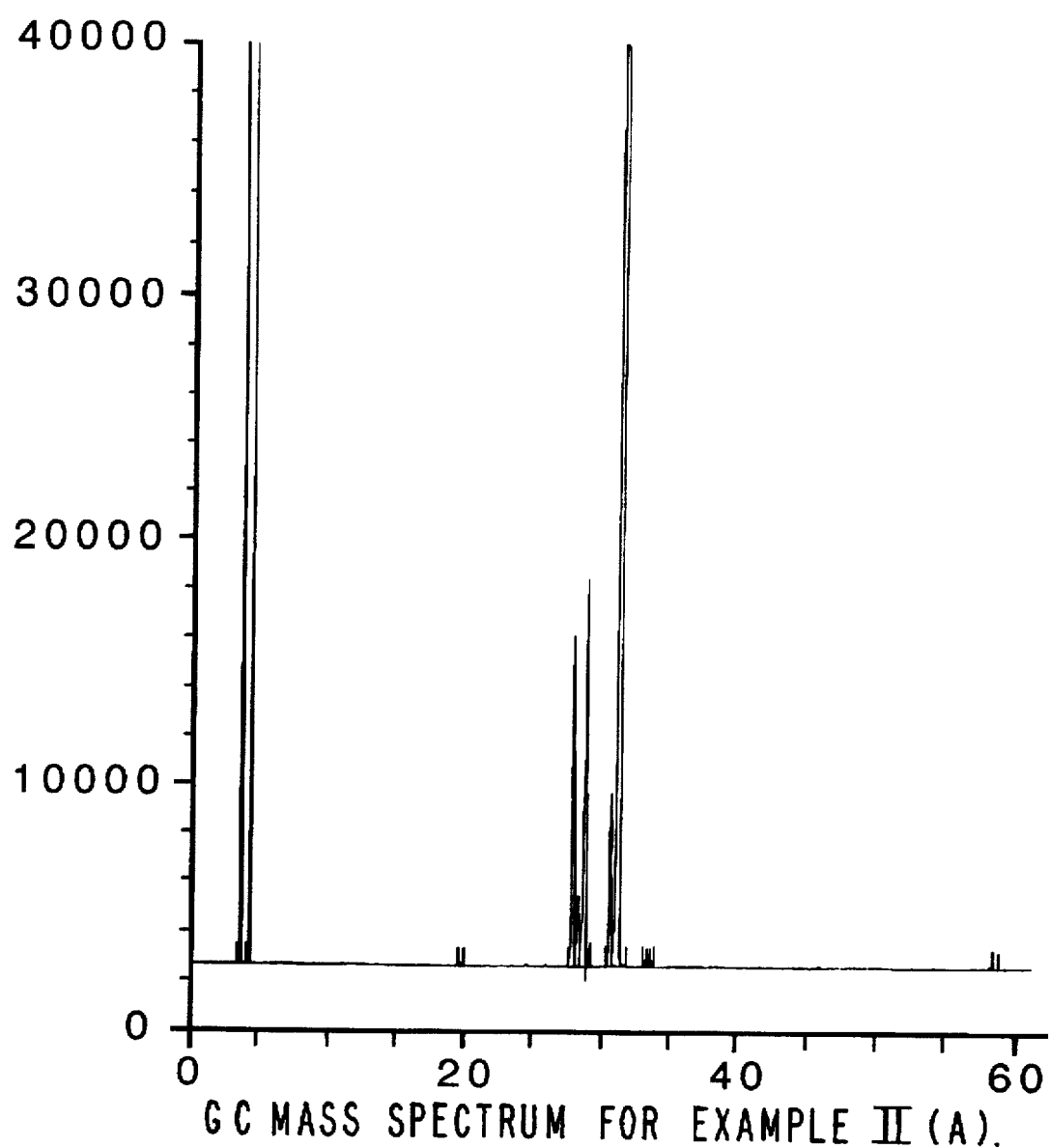
FIG.II-A
GC MASS SPECTRUM FOR EXAMPLE II (A).

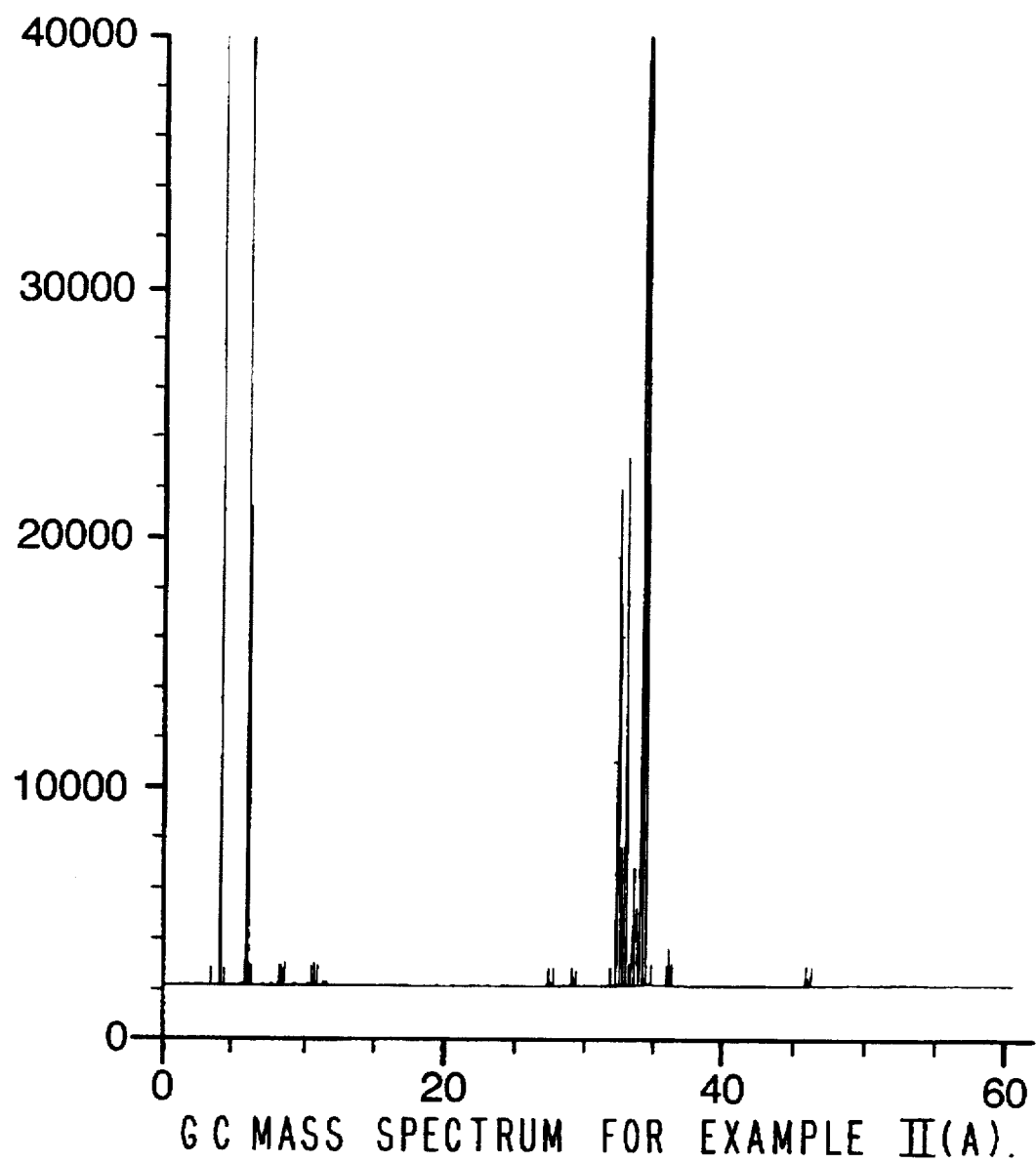
FIG.II-B
GC MASS SPECTRUM FOR EXAMPLE II(A).

MIDDLE DISTILLATION CUT
FIRST DISTILLATION FRACTION 5

GLC PROFILE FOR EXAMPLE II(A).

FIG.13-A
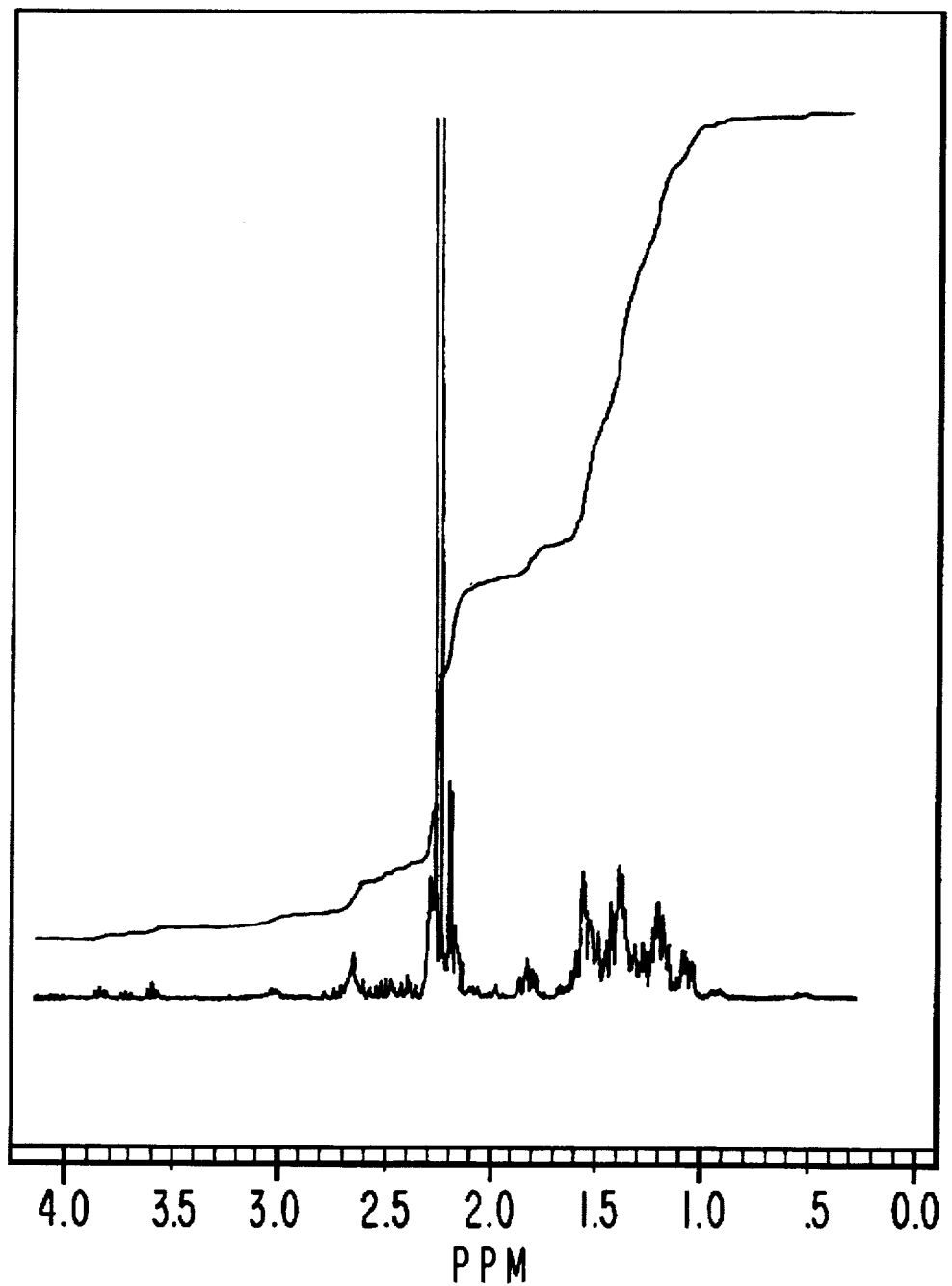

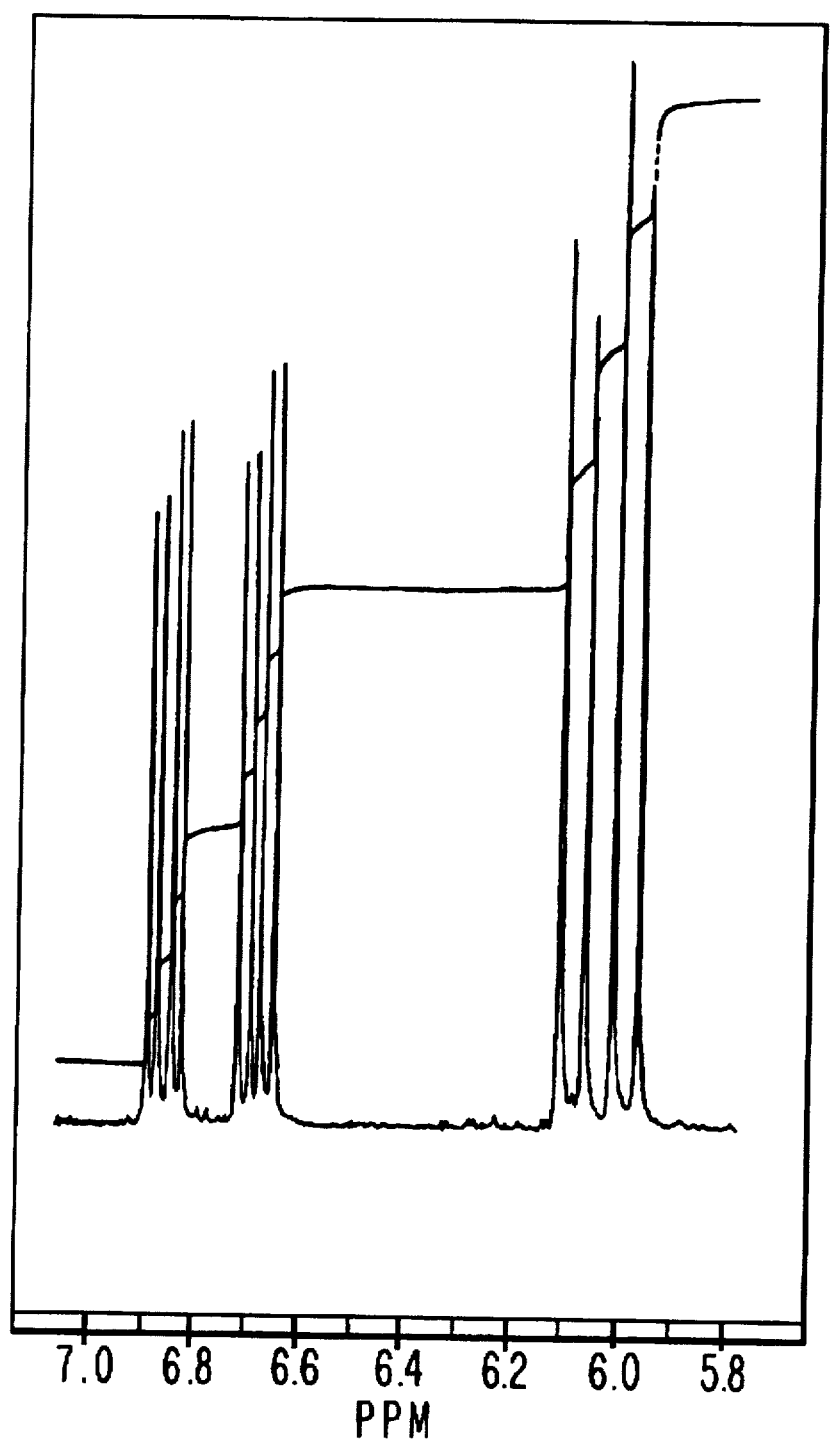
FIG.13-B

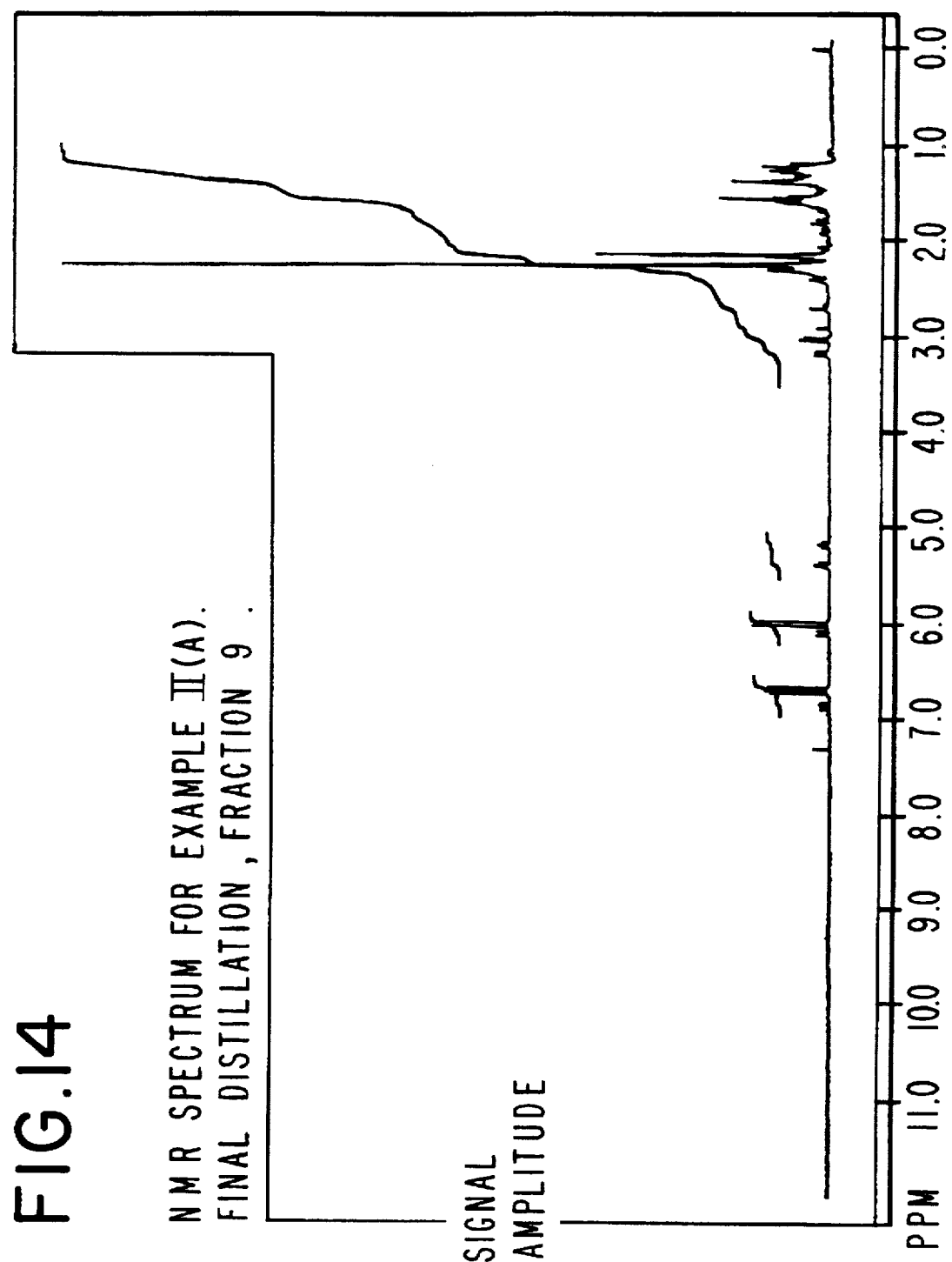
FIG.14 NMR SPECTRUM FOR EXAMPLE II(A). FINAL DISTILLATION, FRACTION 9.

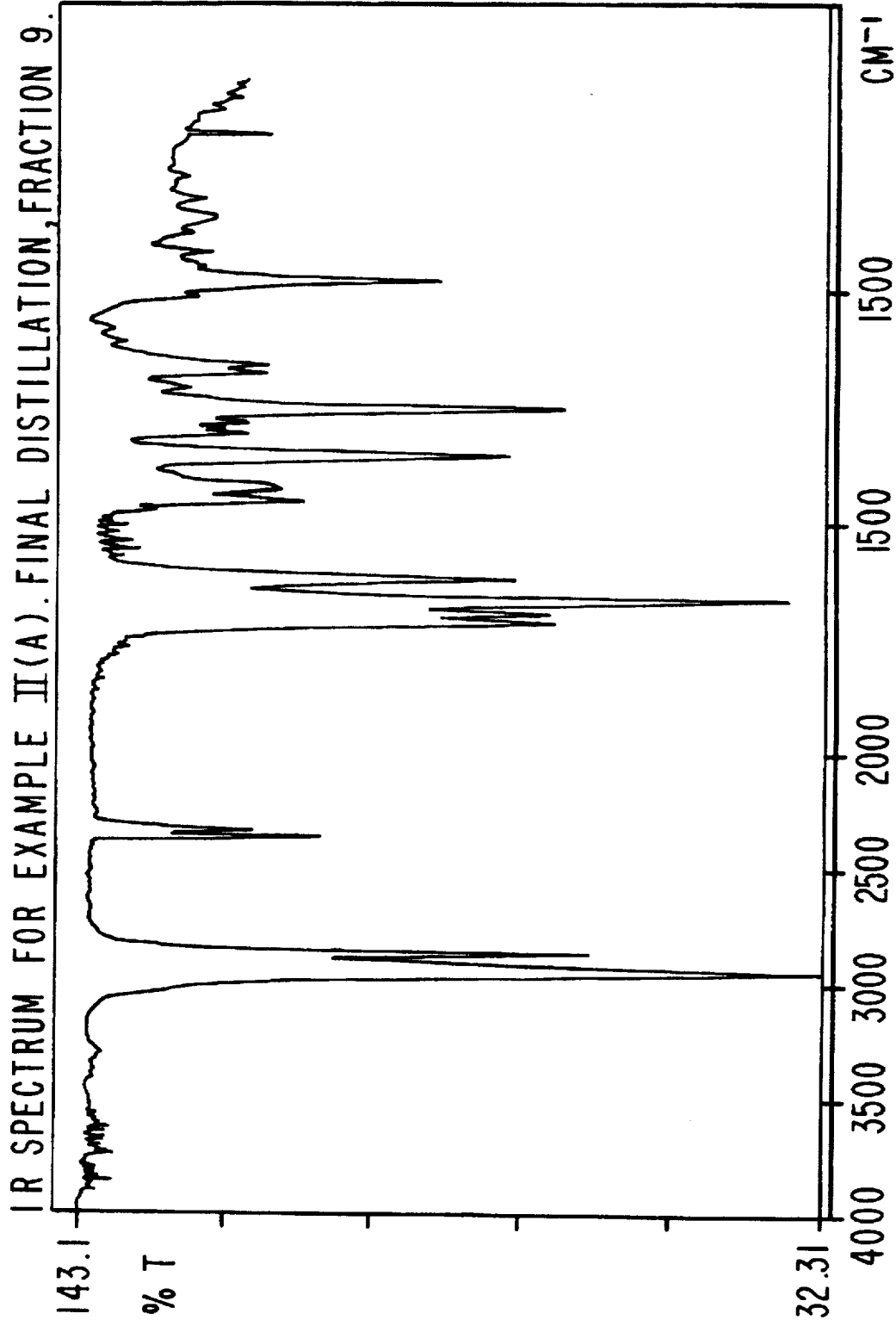

GLC PROFILE FOR EXAMPLE II(B).

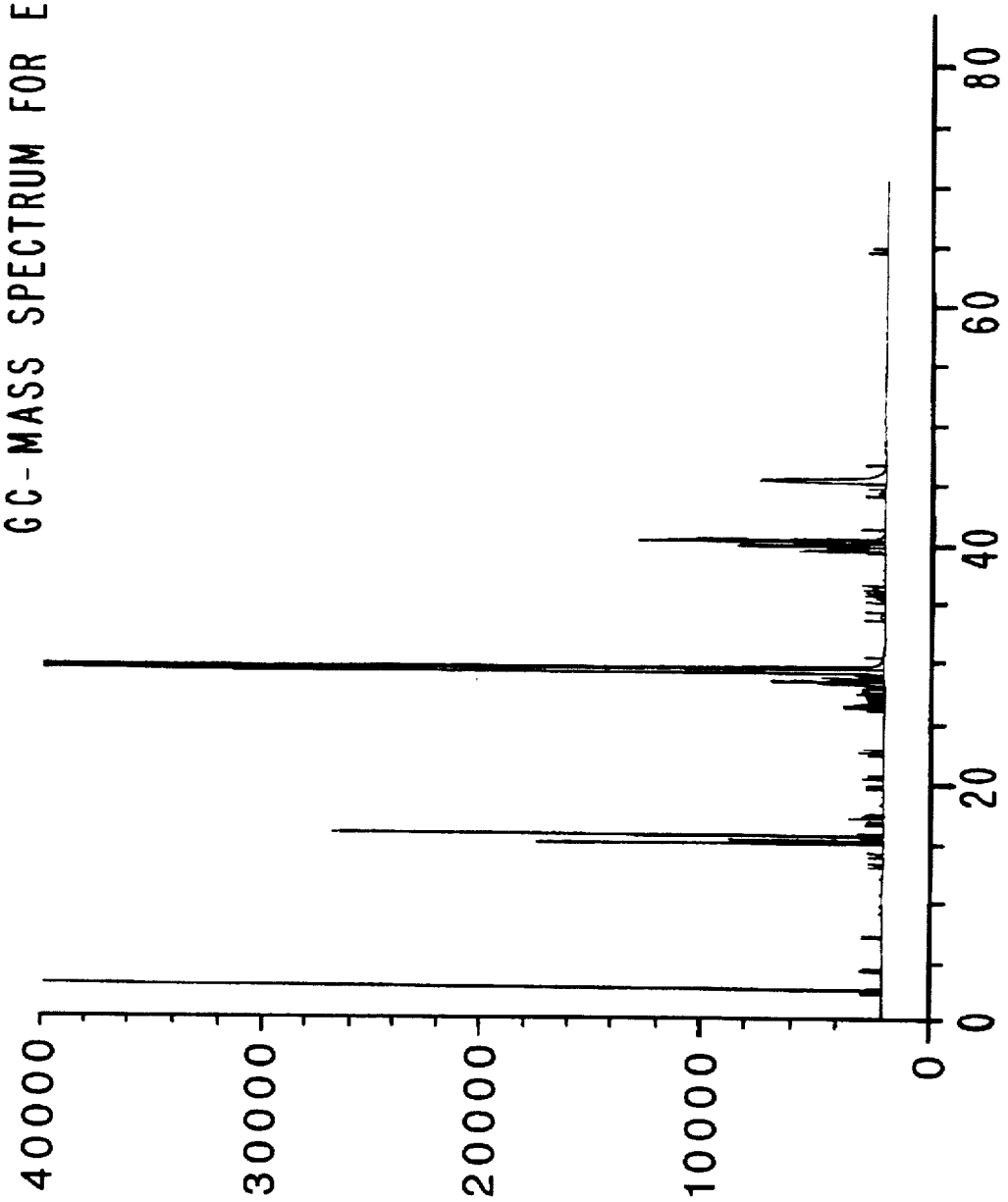
FIG. 17-A
GC-MASS SPECTRUM FOR EXAMPLE II(B).

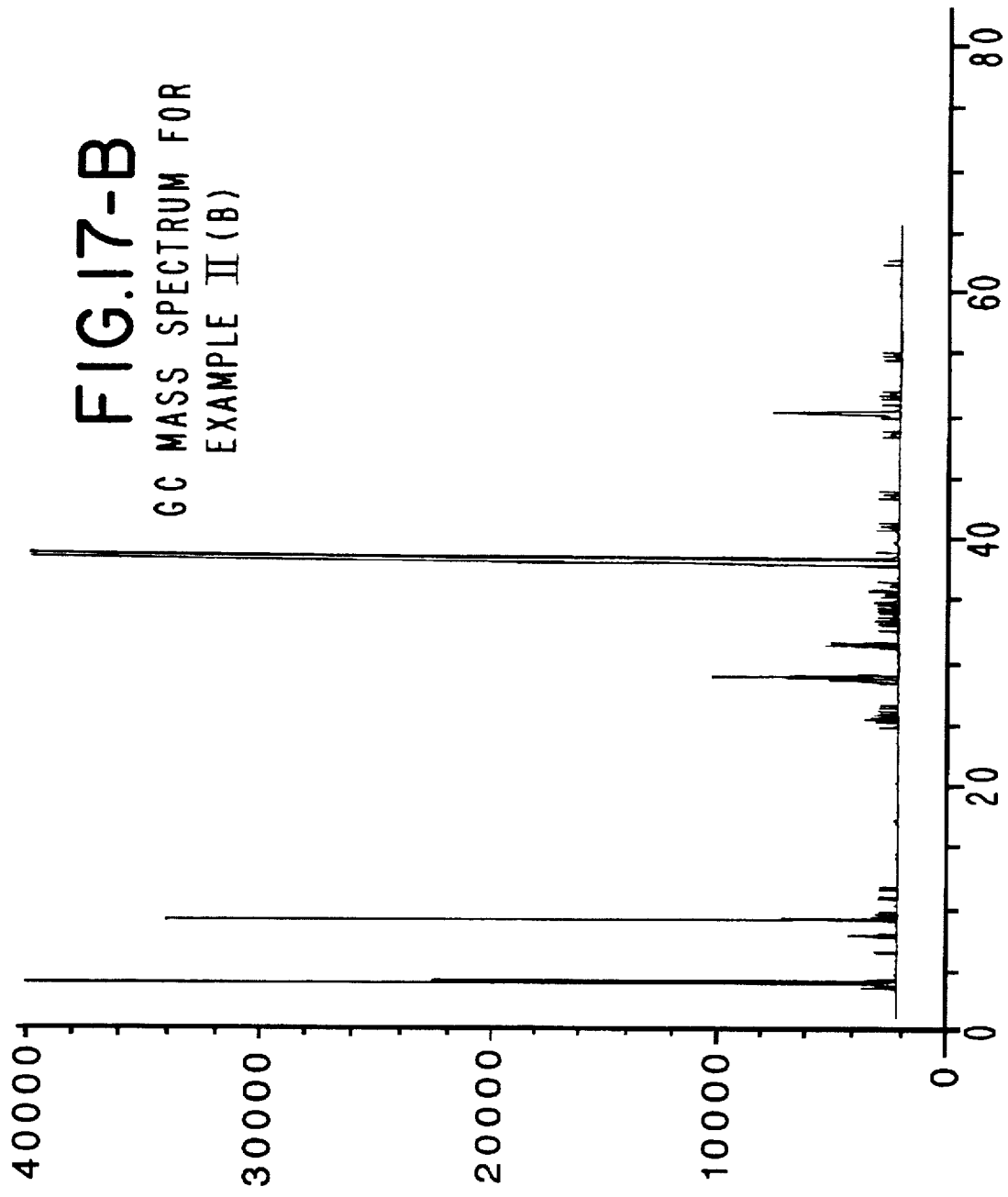
FIG.17-B GC MASS SPECTRUM FOR EXAMPLE II (B)

GLC PROFILE FOR EXAMPLE II(B).

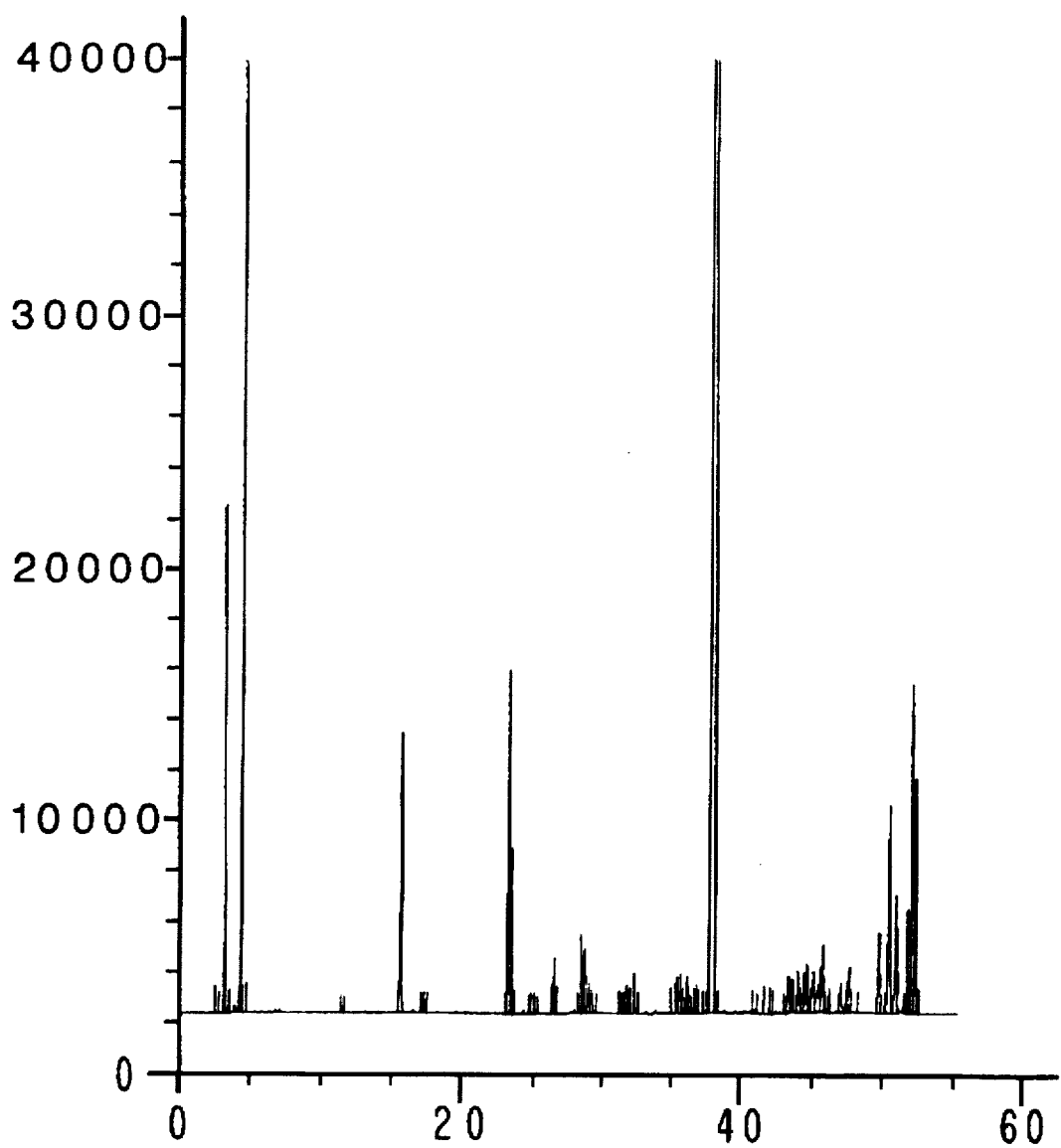
FIG.19-A
GC MASS SPECTRUM FOR EXAMPLE II(B).

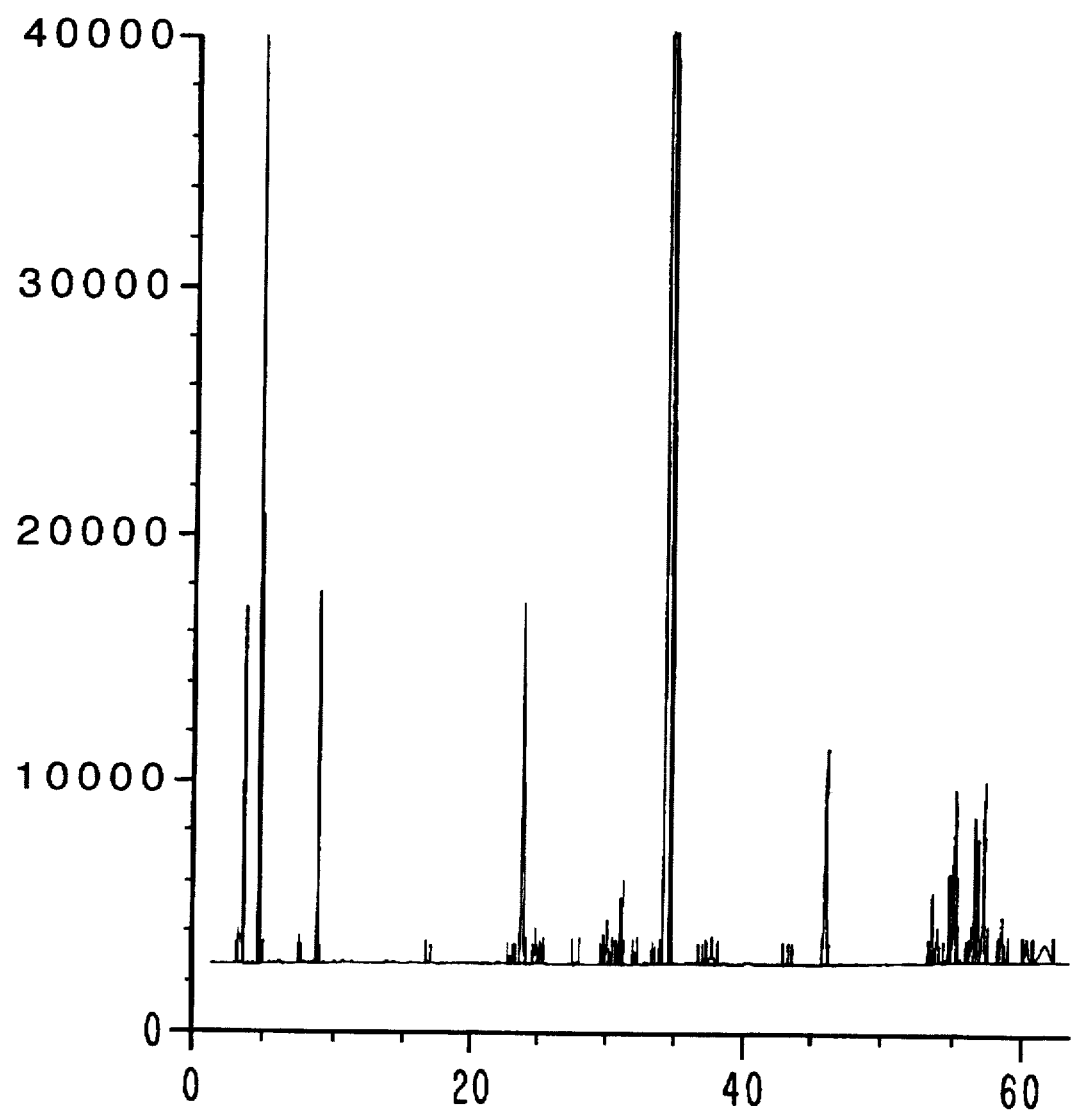
FIG. 19-B
GC MASS SPECTRUM FOR EXAMPLE II(B).

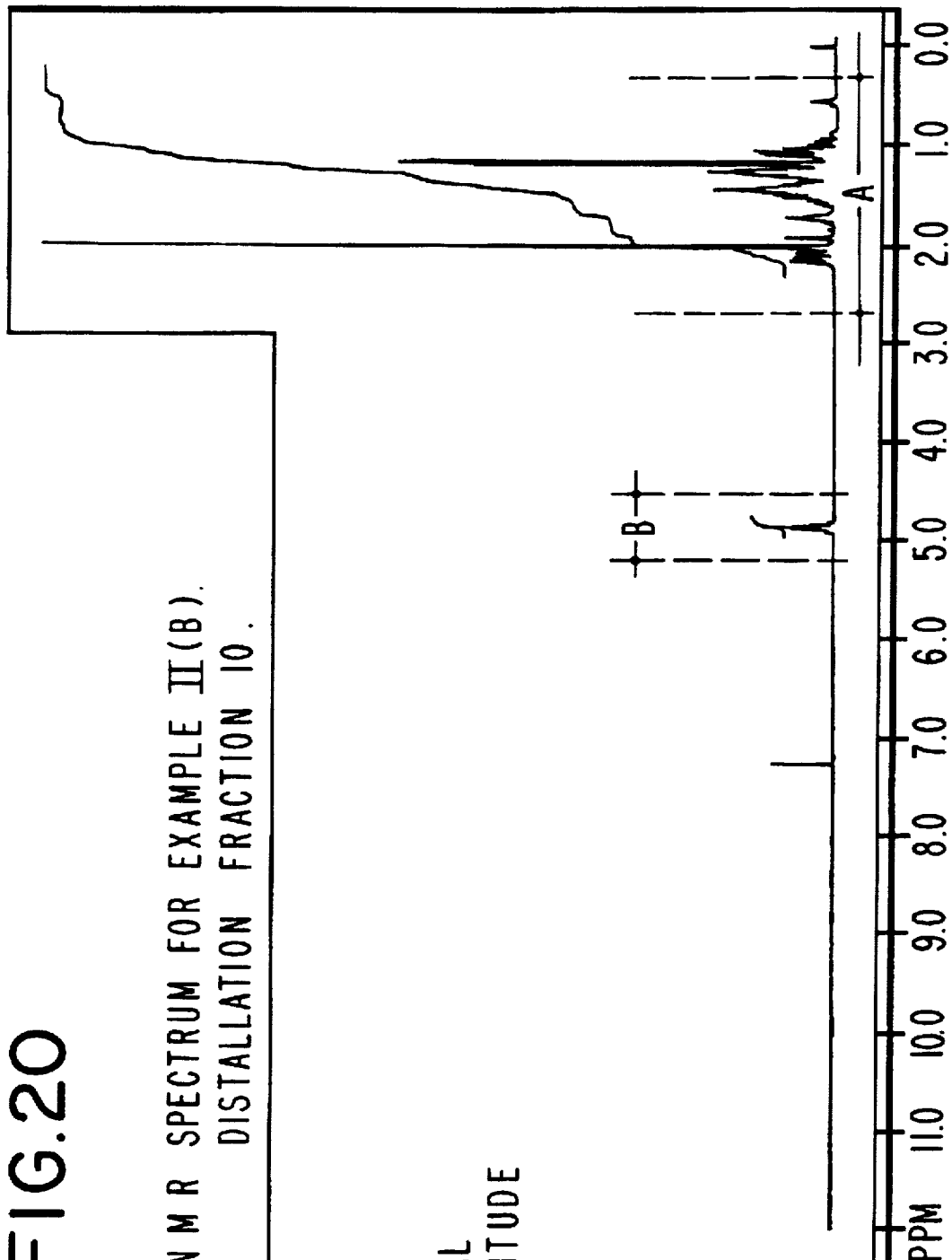
FIG. 20 NMR SPECTRUM FOR EXAMPLE II(B). DISTALLATION FRACTION 10.

FIG.20-A
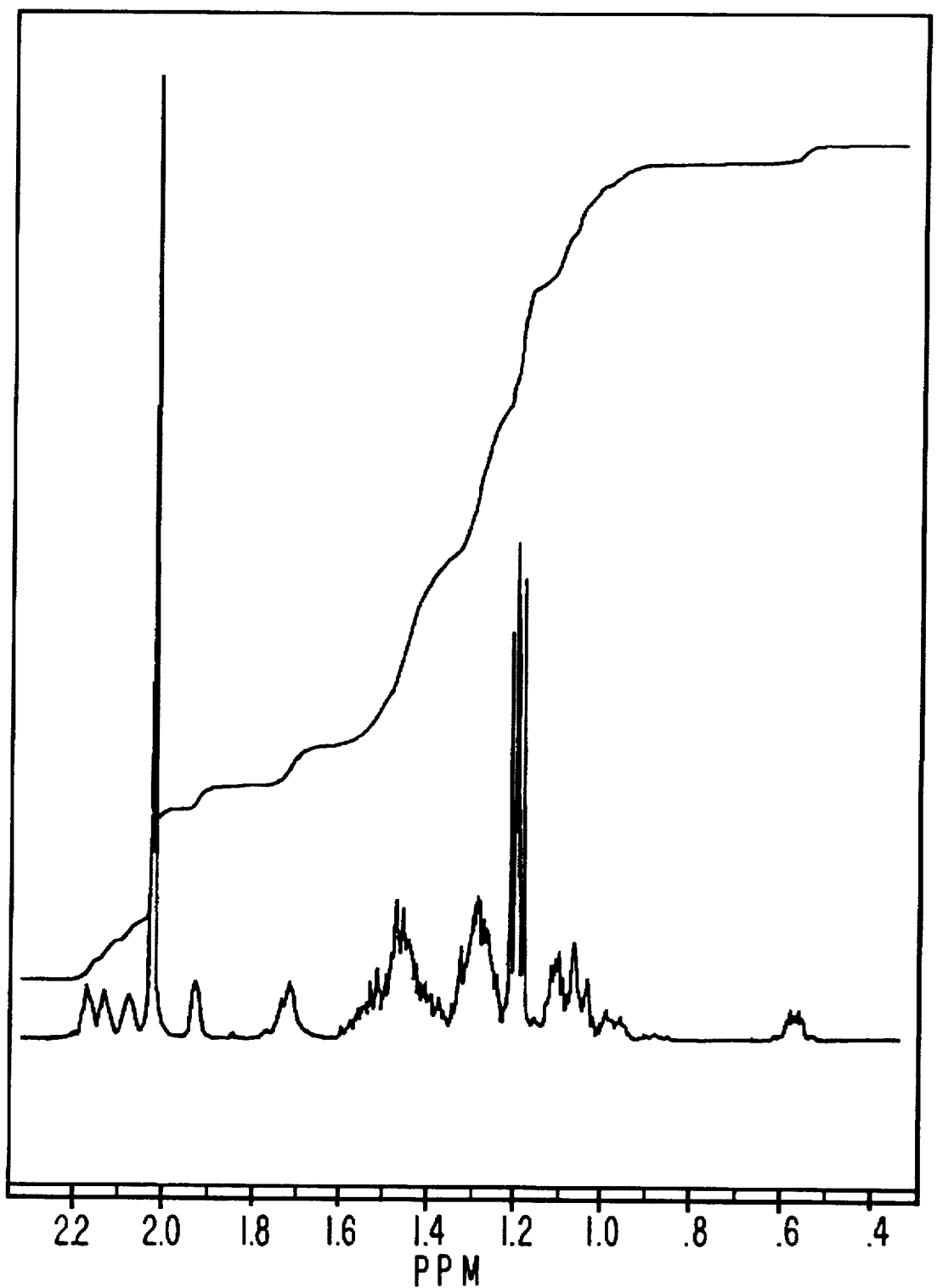

FIG.20-B
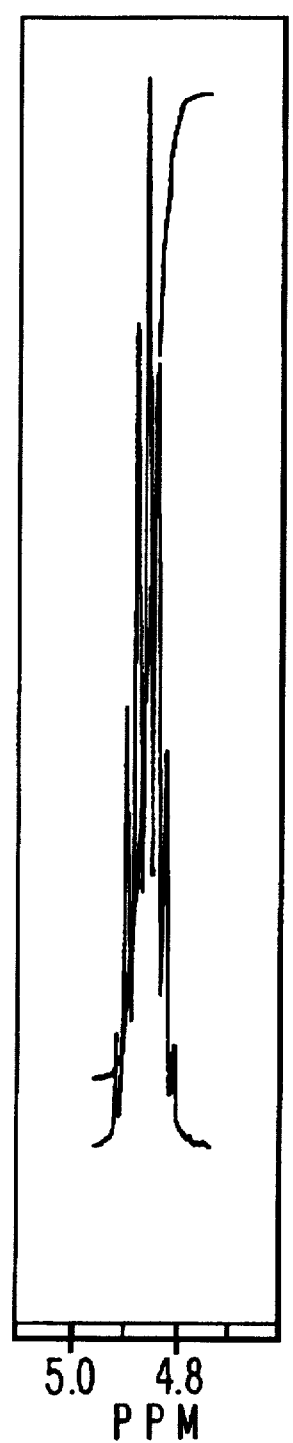

METHYL-SUBSTITUTED 1(2-NORBORNYL) ALKANOLS ACETATE ESTERS THEREOF AND PERFUMERY USES OF SAID ESTERS, AND PROCESS INTERMEDIATES FOR PRODUCING SAME

BACKGROUND OF THE INVENTION

Our invention relates to the prefumery uses of methyl-substituted 1(2-norbornyl) alkanol acetate esters defined according to the structures:

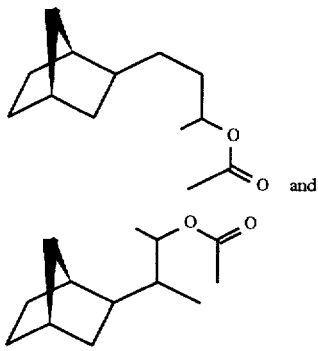

and intermediates for producing such esters including the alkanols defined according to the structures:

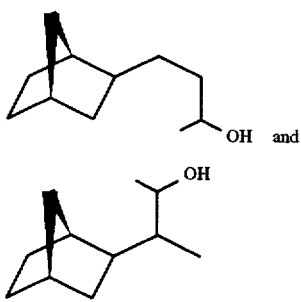

as well as organometallic compounds defined according to the structures:

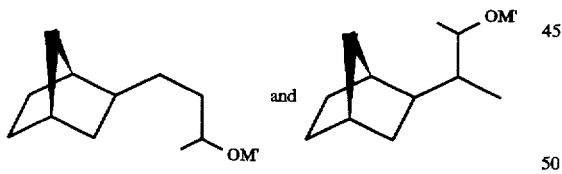

wherein M' is MgX or Li and wherein X is chloro, bromo or iodo.

Chemical compounds which can provide seashore, ozoney, fruity, dry orange peel, bergamot and fatty aromas with rose, fatty, buttery, seashore and dry orange peel topnotes are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the essential fragrance notes provided by natural essential oils or compositions thereof having the above properties. Unfortunately, many of these synthetic materials either have the desired nuances only to a relatively small degree or else contribute undesirable or unwanted odor to the compositions.

Methyl-substituted norbornyl esters are shown to be useful in the art of perfumery by Light, et al, U.S. Pat. No. 4,076,853 wherein such esters are defined according to the structure:

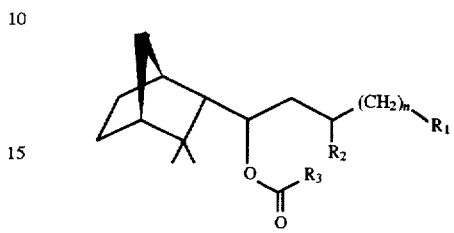

wherein $R_1$ represents hydrogen or lower alkyl; $R_2$ represents hydrogen or lower alkyl; $R_3$ represents hydrogen or lower alkyl; and n is zero or one. At columns 41 and 42, lines 1–5, Light, et al also discloses for use in perfumery the compound having the structure:

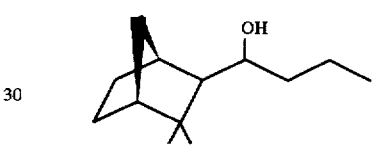

which is indicated to have a "camphoraceous, woody and green aroma with minty nuances". Schleppnik, I, U.S. Pat. No. 3,942,761 discloses the genus of compounds having the structure:

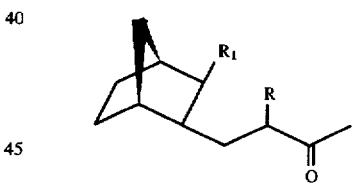

wherein R represents hydrogen or lower alkyl and $R_1$ represents hydrogen or methyl, for use in perfumery. Schleppnik, II, U.S. Pat. No. 3,803,244 discloses the compounds having the generic structure:

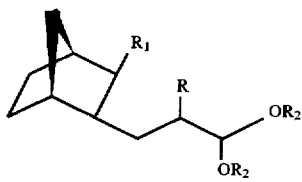

for use in perfumery wherein R and $R_2$ represent lower alkyl; and wherein $R_1$ represents hydrogen or methyl. Schleppnik, III, U.S. Pat. No. 3,780,109 discloses the genus of compounds having the structure:

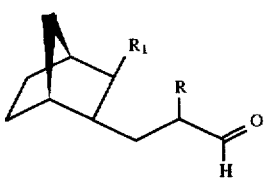

for use in perfumery wherein $R_1$ is hydrogen or methyl and R represents lower alkyl.

Schleppnik, IV, *Chemical Abstracts*, Volume 90:121081 (abstract of U.S. Pat. No. 4,128,509) discloses specifically the compound having the structure:

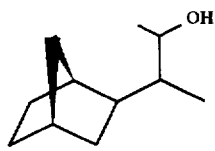

for use in perfumery. However, Schleppnik, IV, or any of the other references, do not infer mixtures of the compound having the structures:

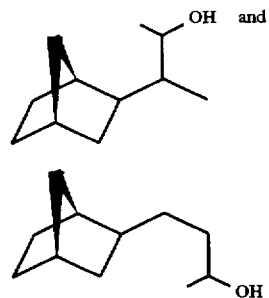

for use as intermediates in preparing esters defined according to the structures:

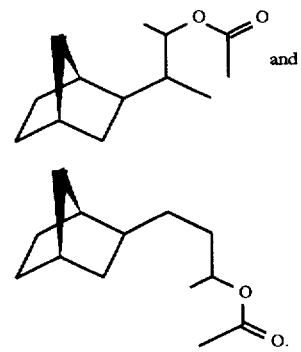

Furthermore, Schleppnik, IV does not disclose the alcohol defined according to the structure:

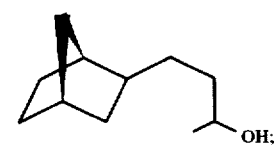

but only the alcohol having the structure:

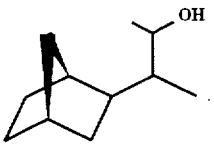

Arctander, *Perfume and Flavor Chemicals (Aroma Chemicals)*, Volume I, published in 1969, discloses at monograph 1029 the norbornyl ester having the structure:

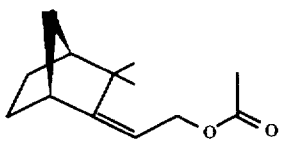

for use in perfumery. Arctander indicates:

"Mild and sweet-woody odor with a floral-piney undertone. The commercial products are probably not very well-defined single chemicals, and great variations in odor have been observed.

This ester has been developed in line with the research on Sandalwood type odors. The parent alcohol "Camphene carbinol" was once considered useful as a Sandalwood type material, but it has found more use as a sweetening and enriching ingredient in sophisticated Pine fragrances. The title ester finds limited use in perfume compositions of woody character, Fougeres, Pine fragrances, etc. and it blends very well with the Cyclohexanol derivatives, Ionones, iso-Bornylacetate, Nitromusks, etc."

None of the foregoing references, including the Schleppnik references I–IV, Arctander or the Light, et al reference, discloses or infers the existence of the compound having the structure:

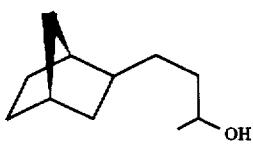

or the compound having the structure:

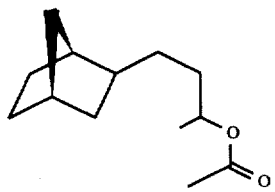

or the compound having the structure:

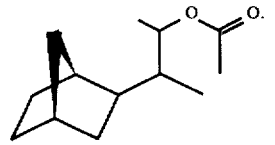

Furthermore, nothing in the prior art discloses for use in perfumery the compound having the structure:

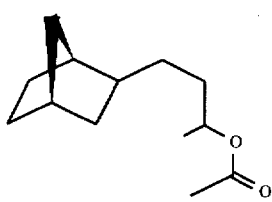

or the compound having the structure:

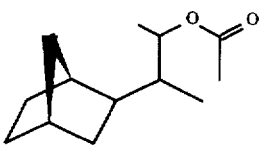

which have unobvious, unexpected and advantageous properties.

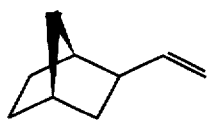

(conditions: SE-30 column programmed from 80°–220° C. at 6° C. per minute).

FIG. 2 is the NMR spectrum for the compound having the structure:

prepared according to Example I(A).

FIG. 2A is an enlargement of section "A" of the NMR spectrum of FIG. 2.

FIG. 2B is an enlargement of section "B" of the NMR spectrum of FIG. 2.

FIG. 2C is an enlargement of section "C" of the NMR spectrum of FIG. 2.

Figure 3:
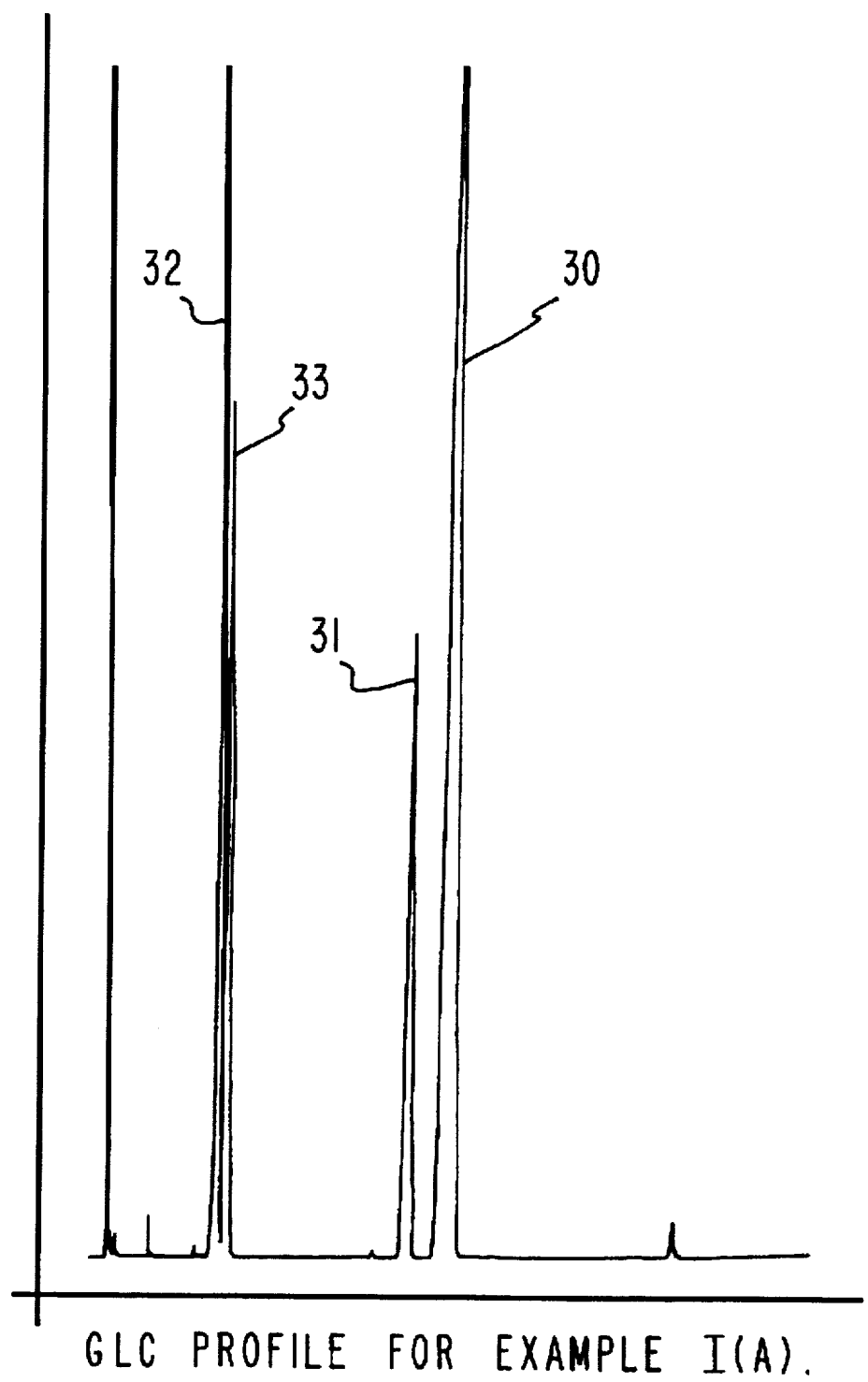

FIG. 3 is the GLC profile for the reaction product of Step 2 of Example I(A) containing the compounds having the structures:

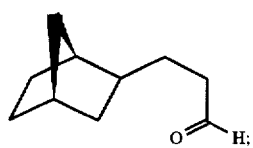

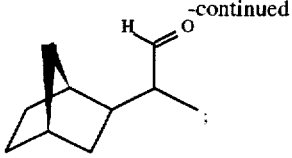

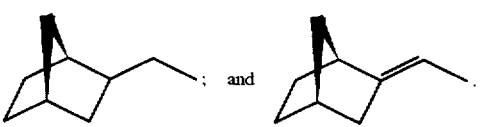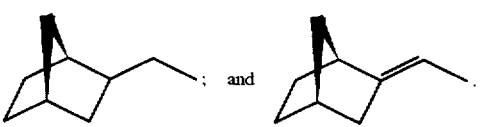

Figure 4:
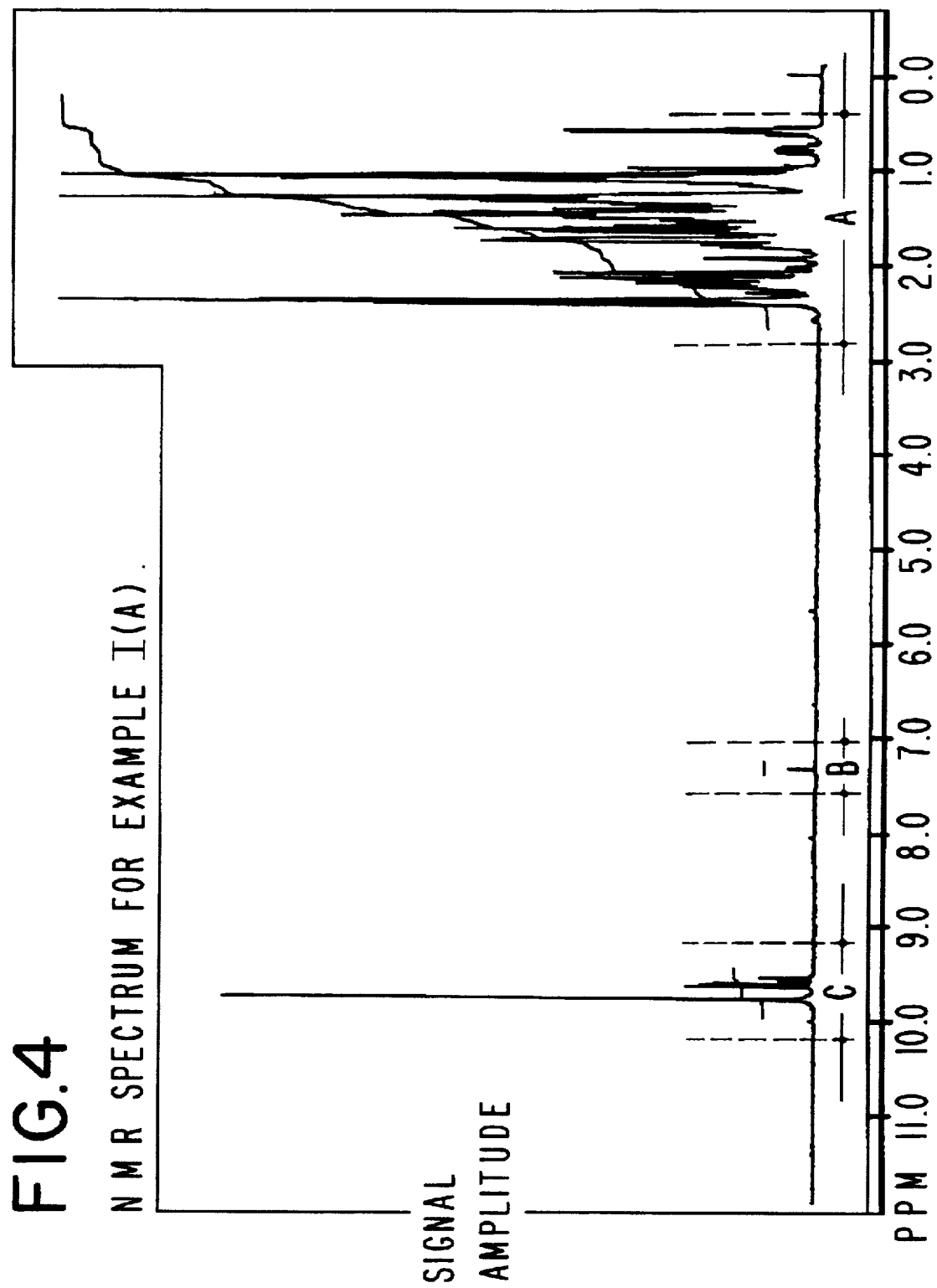

FIG. 4 is the NMR spectrum for the mixture of compounds having the structures:

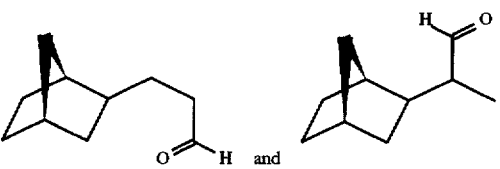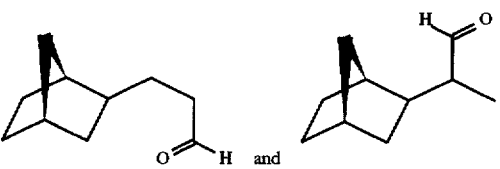

with the ratio of the compounds:

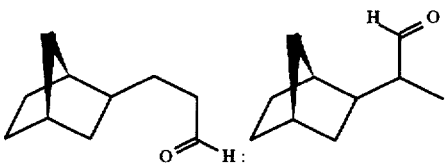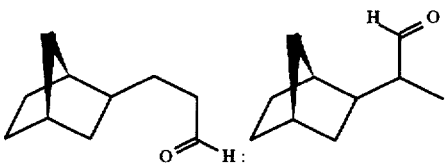

being 3:1.

FIG. 4A is an enlargement of section "A" of the NMR spectrum of FIG. 4.

FIG. 4B is an enlargement of section "B" of the NMR spectrum of FIG. 4.

FIG. 4C is an enlargement of section "C" of the NMR spectrum of FIG. 4.

FIG. 5 is the GLC profile for the reaction product of Example I(B) containing the compounds having the structures:

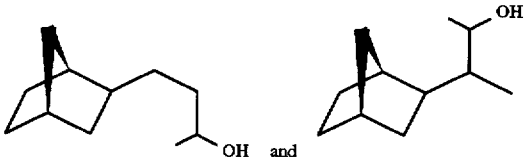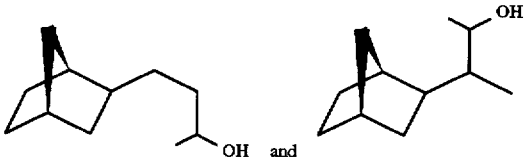

(conditions: SE-30 column programmed at 160° C. isothermal).

FIG. 6 is the NMR spectrum for the mixture of compounds having the structures:

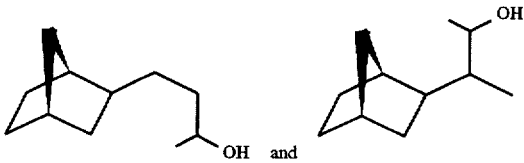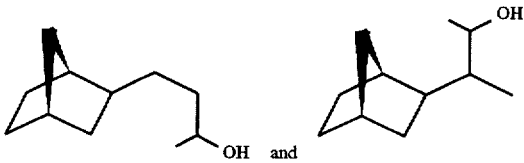

prepared according to Example I(B).

FIG. 6A is an enlargement of section "A" of the NMR spectrum of FIG. 6.

FIG. 6B is an enlargement of section "B" of the NMR spectrum of FIG. 6.

Figure 7:
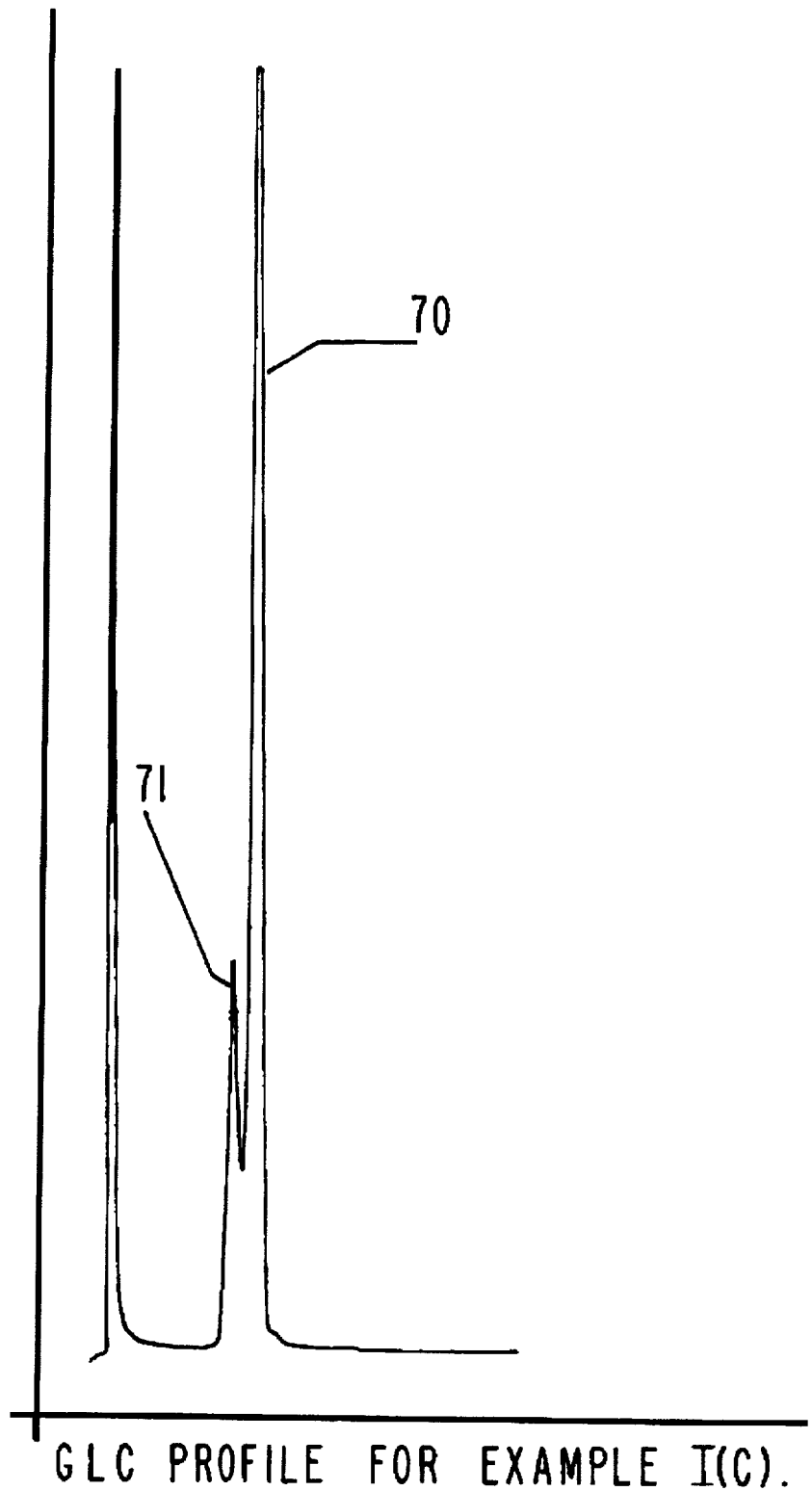

FIG. 7 is the GLC profile for the crude reaction product of Example I(C) containing the compounds having the structures:

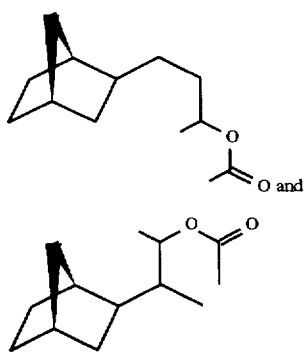

(conditions: SE-30 column programmed at 180° C. isothermal).

FIG. 8 is the NMR spectrum for the mixture of compounds having the structures:

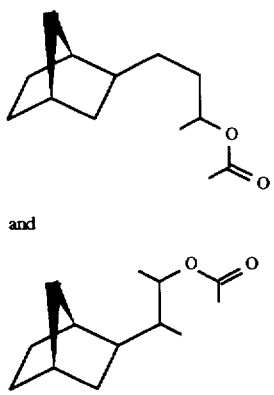

prepared according to Example I(C).

FIG. 8A is an enlargement of section "A" of the NMR spectrum of FIG. 8.

Figure 9:
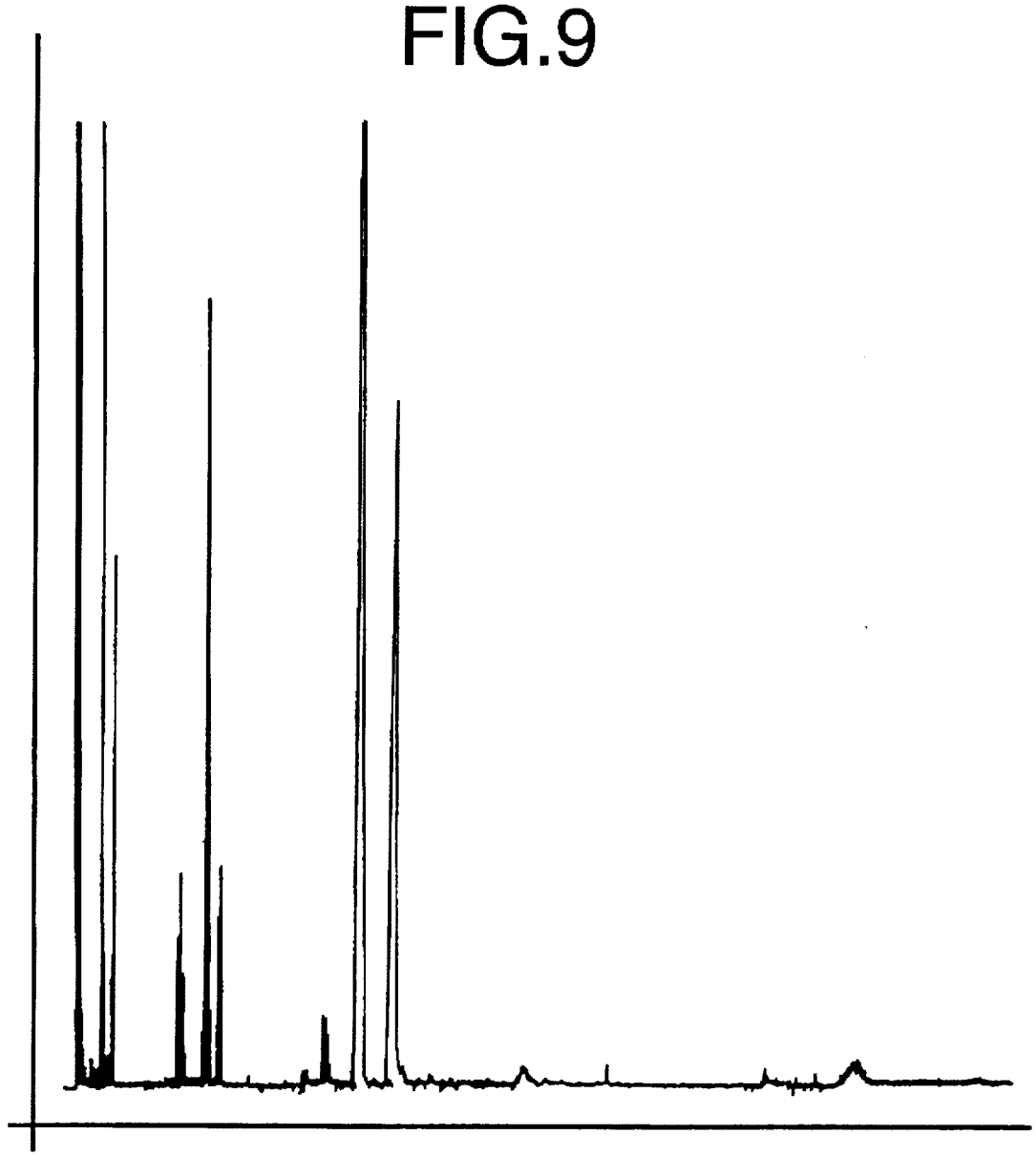

FIG. 9 is the GLC profile for the crude reaction product of Example II(A) containing the compounds having the structures:

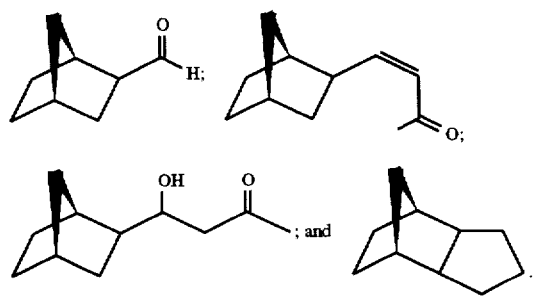

FIG. 10 is the GC mass spectrum for the crude reaction product of Example II(A) containing the compounds having the structures:

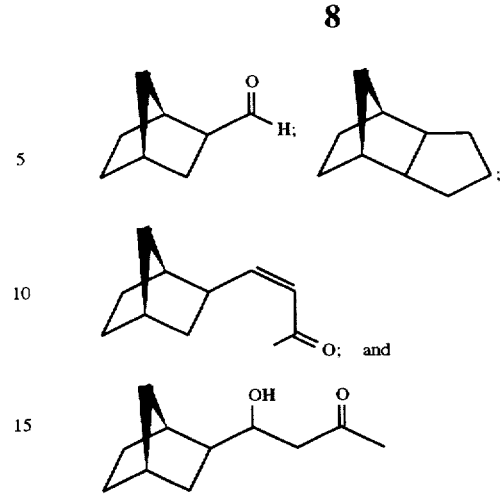

(conditions: 50 meter×0.32 mm methyl silicone bonded, fused silica OV-1 column programmed from 75° up to 225° C. at 2.0° C. per minute).

FIG. 11(A) is the GC mass spectrum for the mixture of compounds having the structures:

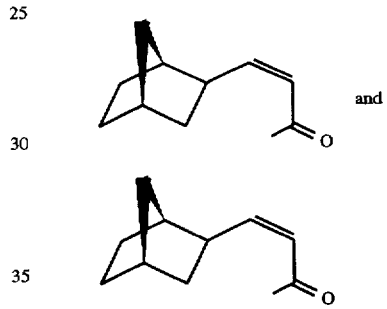

prepared according to Example II(A) (Carbowax column).

FIG. 11B is the GC mass spectrum for the mixture of compounds having the structures:

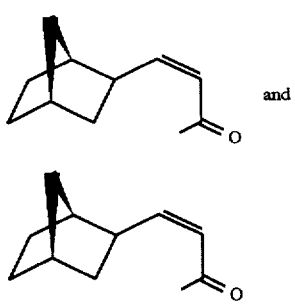

produced according to Example II(A) (OV-1 column).

Figure 12:
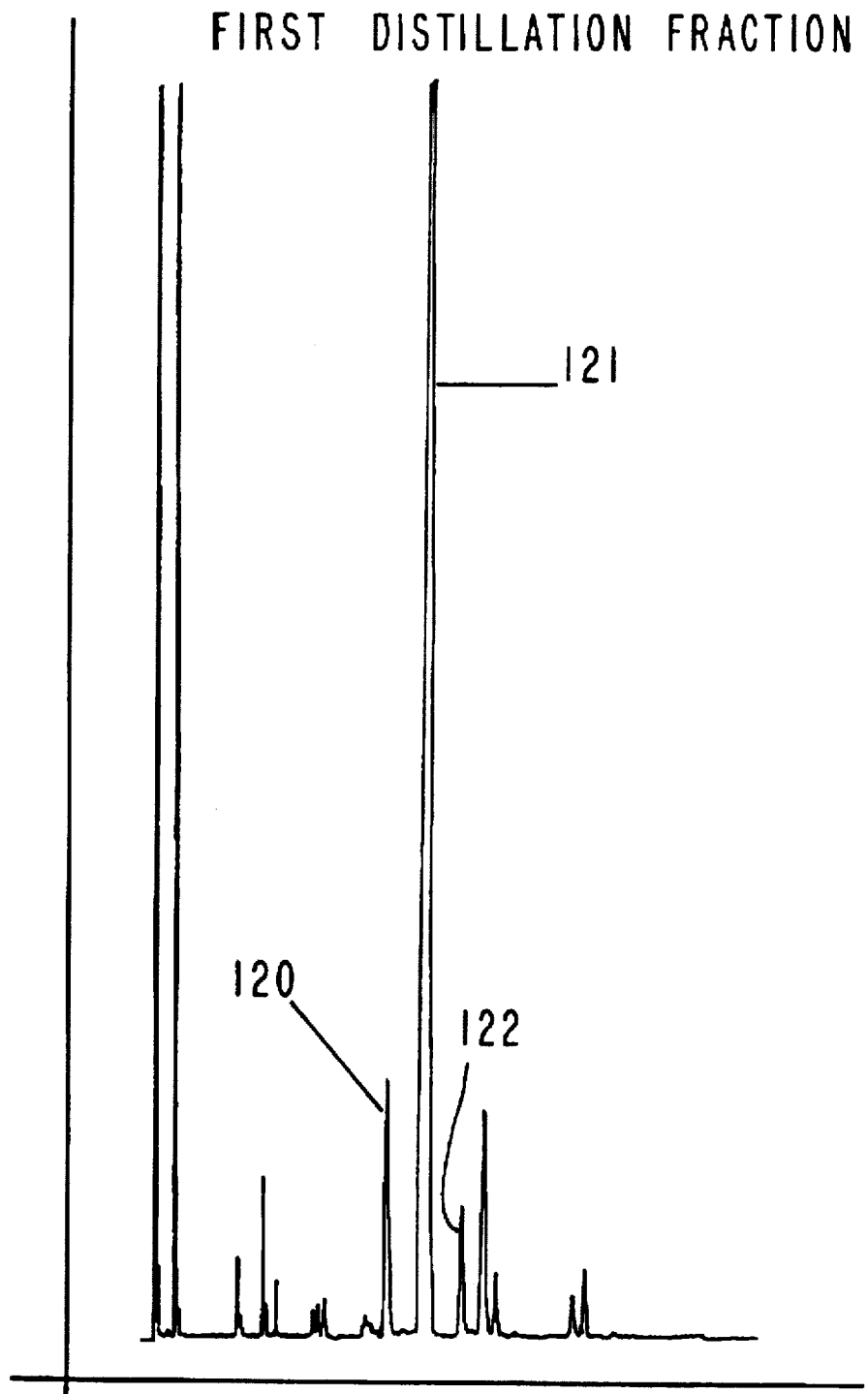

FIG. 12 is the GLC profile for the middle distillation cut (first distillation fraction 5) of the reaction product of Example II(A) containing the compounds having the structures:

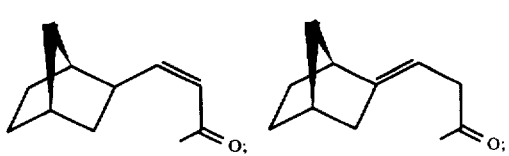

-continued

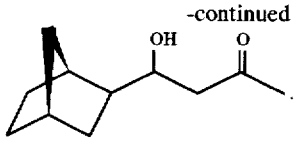

Figure 13:
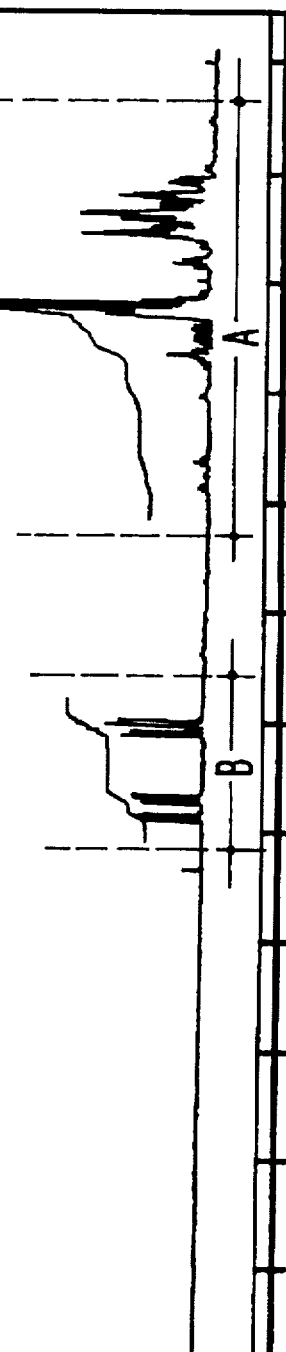

FIG. 13 is the NMR spectrum for the middle distillation cut (first distillation fraction 5) of the distillation of the reaction product of Example II(A) containing the compounds having the structures:

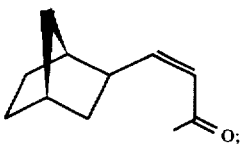
O;

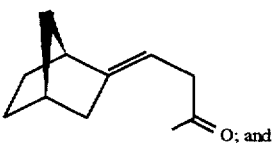
O; and

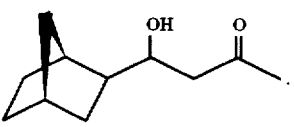

FIG. 13A is an enlargement of section "A" of the NMR spectrum of FIG. 13.

FIG. 13B is an enlargement of section "B" of the NMR spectrum of FIG. 13.

FIG. 14 is the NMR spectrum for the final distillation (fraction 9) of the reaction product of Example II(A) containing the compounds having the structures:

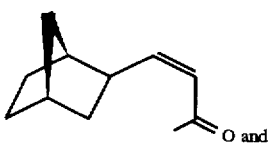
O and

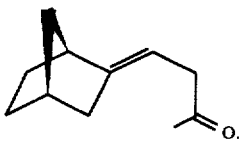
O.

FIG. 15 is the infrared spectrum for the final distillation (fraction 9) of the reaction product of Example II(A) containing the compounds having the structures:

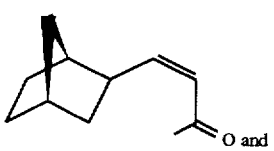
O and

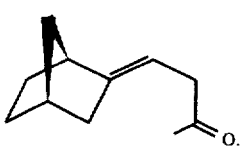
O.

Figure 16:
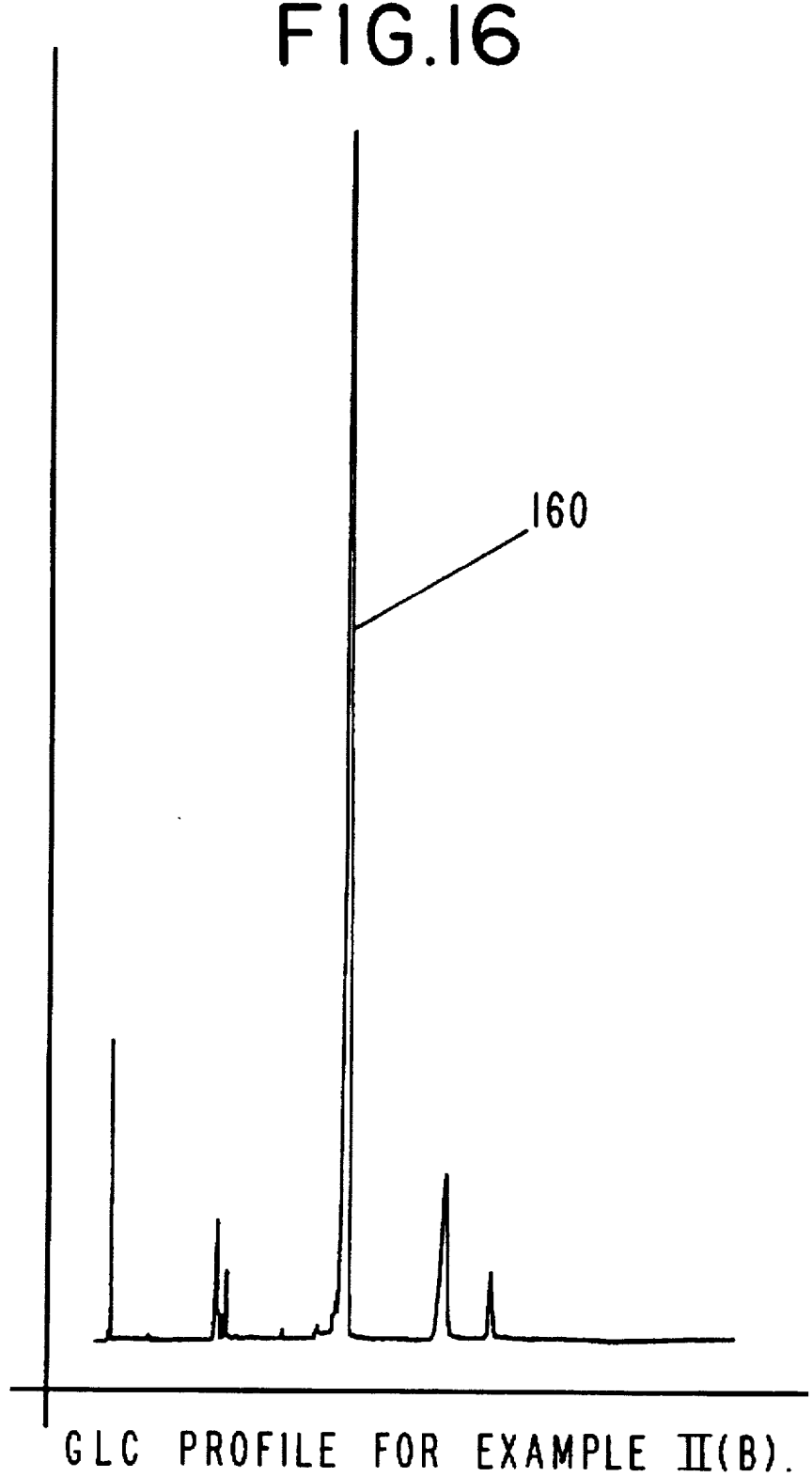

FIG. 16 is the GLC profile for the reaction product of Example II(B) containing the compound having the structure:

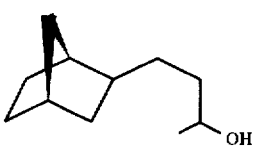

(conditions: SE-30 column programmed from 100°–220° C. at 8° C. per minute).

FIG. 17A is the GC mass spectrum for the reaction product of Example II(B) containing the compound having the structure:

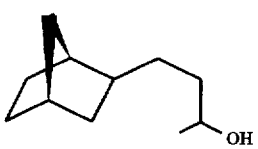

(conditions: 50 meter×0.32 mm methyl silicone, bonded, fused silica (OV-1) column programmed from 75° up to 225° C. at 2.0° C. per minute).

FIG. 17B is the GC mass spectrum for the mixture of compounds having the structures:

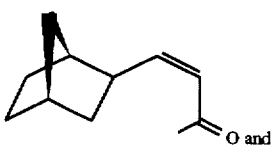
O and

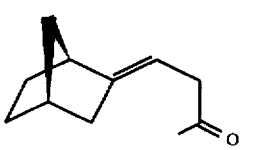
O prepared according to Example II(B) (conditions: 50 meter× 0.32 mm nonbonded, fused silica Carbowax 20M column programmed from 75° up to 225° C. at 2.0° C. per minute).

Figure 18:
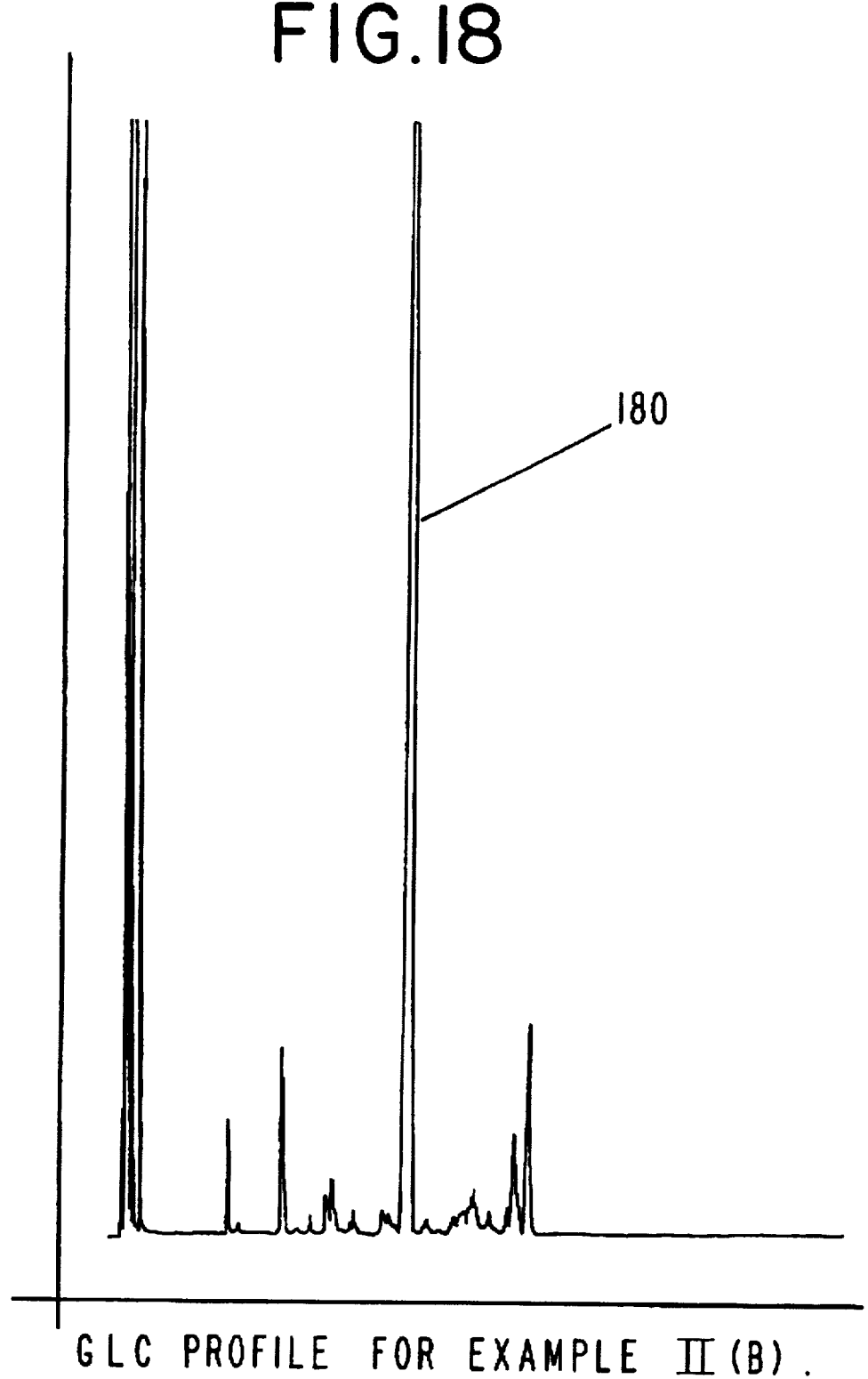

FIG. 18 is the GLC profile for the reaction product of Step 2 of Example II(B) containing the compound having the structure:

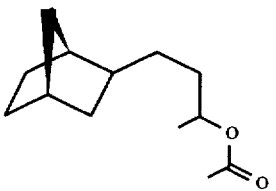

(conditions: SE-30 column programmed from 100°–220° C. at 8° C. per minute).

FIG. 19A is the GC mass spectrum for the compound having the structure:

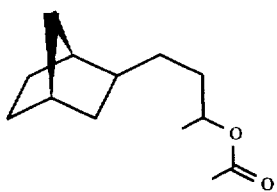

prepared according to Example II(B) (conditions: methyl silicone 50 meter×0.32 mm bonded, fused silica (OV-1) column programmed from 75°–225° C. at 2.0° C. per minute).

FIG. 19B is the GC mass spectrum for the compound having the structure:

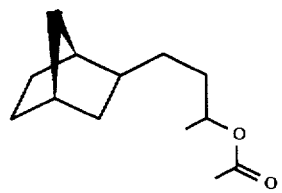

prepared according to Example II(B) (conditions: Carbowax 20M, 50 meter×0.32 mm nonbonded, fused silica column programmed from 75°–225° C. at 2.0° C. per minute).

FIG. 20 is the NMR spectrum for distillation fraction 10 of the distillation of the reaction product of Example II(B) containing the compound having the structure:

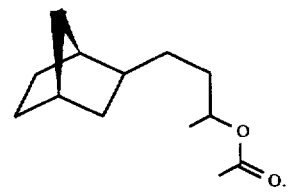

FIG. 20A is an enlargement of section "A" of the NMR spectrum of FIG. 20.

FIG. 20B is an enlargement of section "B" of the NMR spectrum of FIG. 20.

Figure 21:
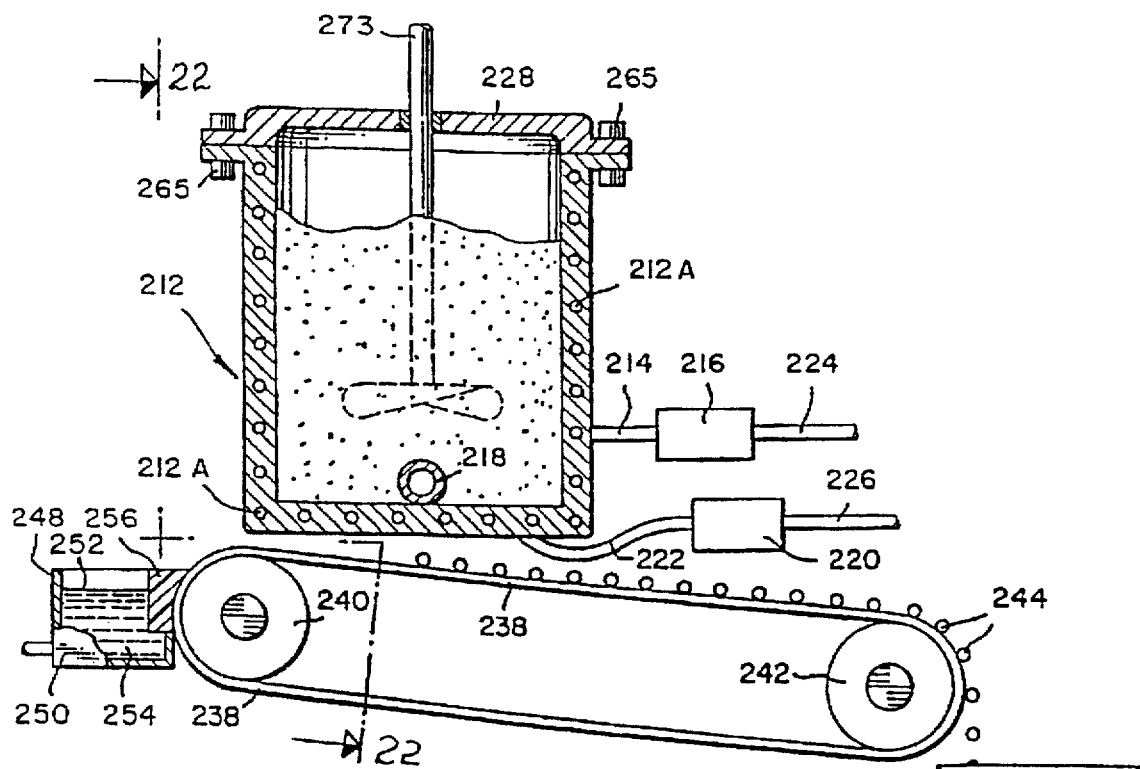

FIG. 21 is a cutaway side elevation view of apparatus used in producing polymeric fragrances containing at least one of the methyl-substituted 1(2-norbornyl) alkanol acetate esters of our invention.

Figure 22:
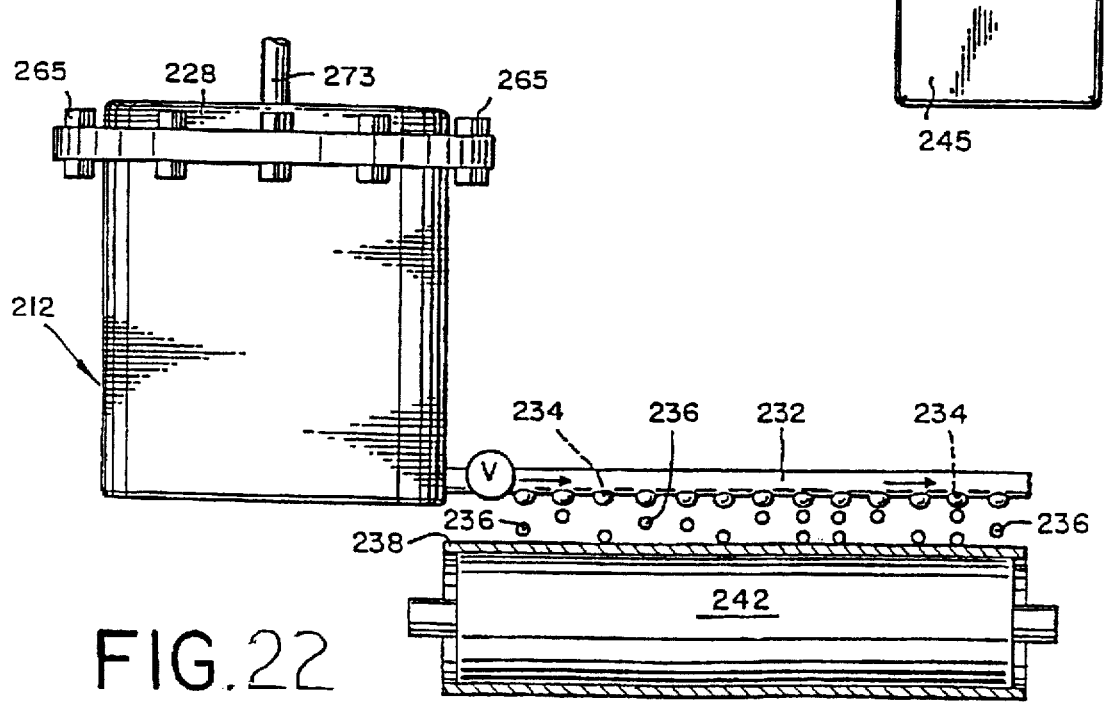

FIG. 22 is the front elevation view of the apparatus of FIG. 21 looking in the direction of the arrows along lines 22—22 of FIG. 21.

DETAILED DESCRIPTION OF THE DRAWINGS

Figure 1:
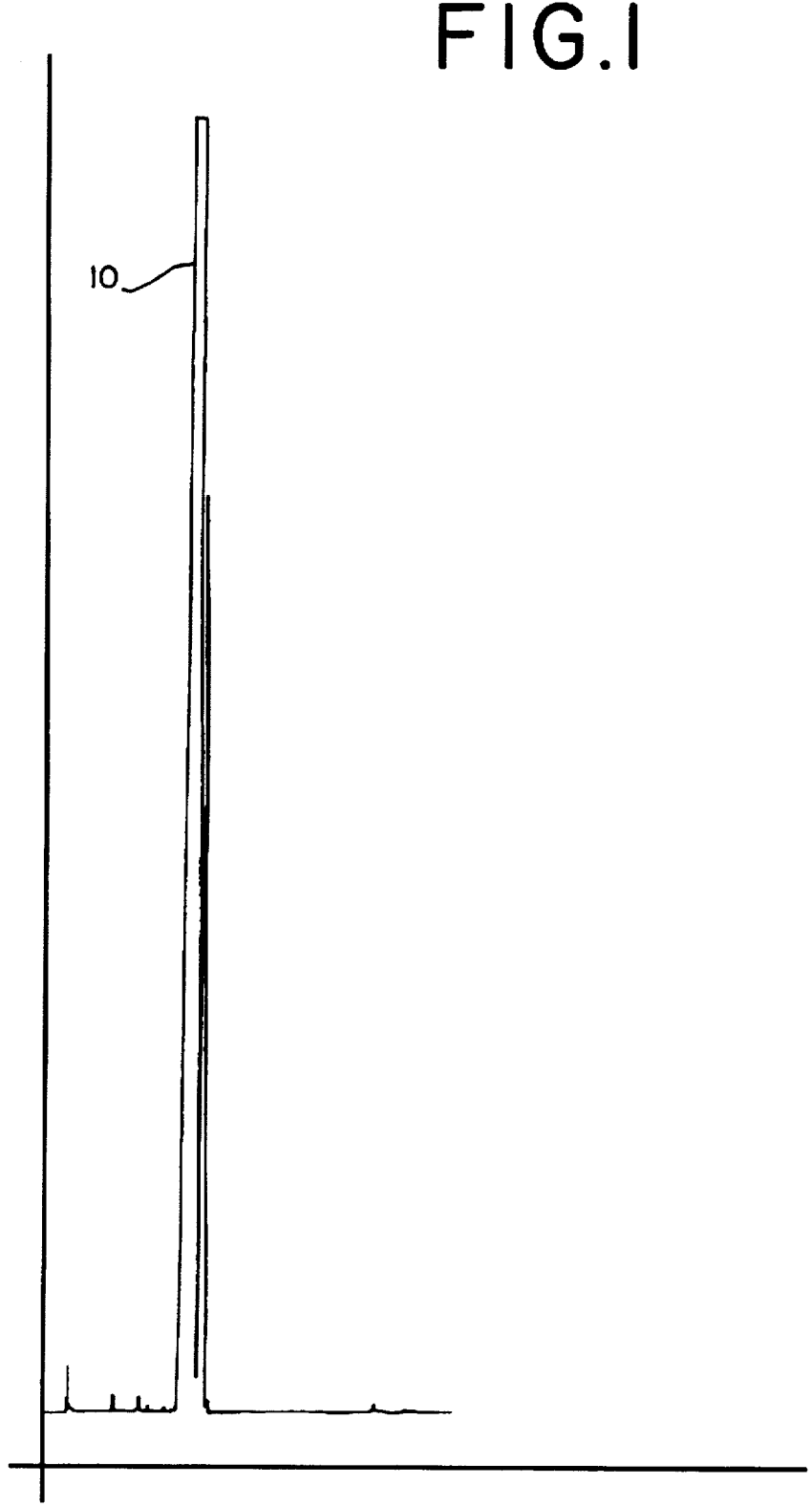
FIG. 1 is the GLC profile for the reaction product of Example I(A) containing the compound having the structure.

FIG. 1 is the GLC profile of the reaction product of Example I(A). The peak indicated by reference numeral 10 is the peak for the compound having the structure:

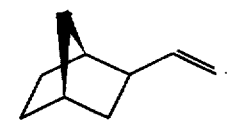

FIG. 3 is the GLC profile for the reaction product of Example I(A), Step 2. The peak indicated by reference numeral 30 is the peak for the compound having the structure:

The peak indicated by reference numeral 31 is the peak for the compound having the structure:

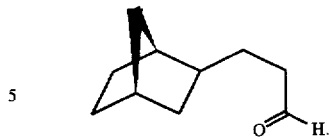

The peaks indicated by reference numerala 32 and 33 are for the compounds having the structures:

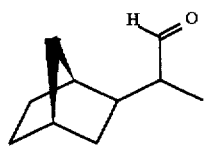

FIG. 5 is the GLC profile for the reaciton product of Example I(B). The peak indicated by reference numeral 50 is the peak for the mixture of compounds having the structures:

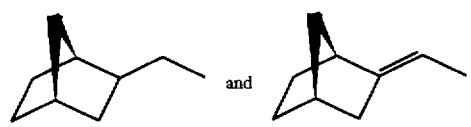

FIG. 7 is the GLC profile for the reaction product of Example I(C). The peak indicated by reference numeral 70 is the peak for the compound having the structure:

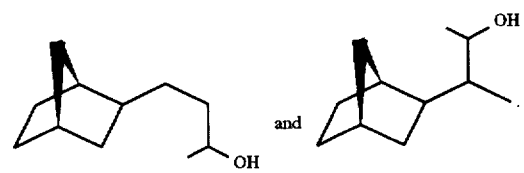

The peak indicated by reference numeral 71 is the peak for the compound having the structure:

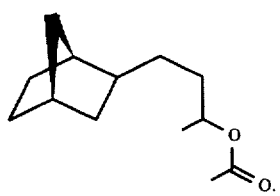

FIG. 10 is the GC mass spectrum for the crude reaction product of Example II(A). The peak indicated by reference numeral 100 is the peak for the compound having the structure:

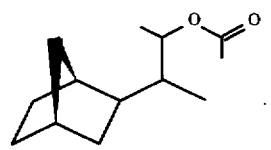

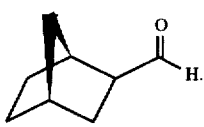

The peak indicated by reference numeral 101 is the peak for the compound having the structure:

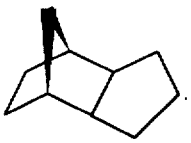

The peak indicated by reference numeral 102 is the peak for the compound having the structure:

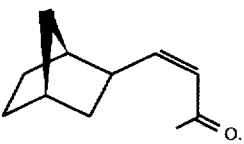

The peak indicated by reference numeral 103 is the peak for the compound having the structure:

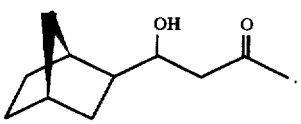

FIG. 12 is the GLC profile for the middle distillation cut (first distillation fraction, fraction 5) for the distillation of the reaction product of Example II(A). The peak indicated by reference numeral 120 is the peak for the compound having the structure:

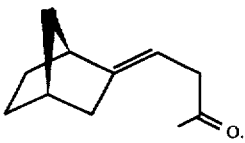

The peak indicated by reference numeral 121 is the peak for the compound having the structure:

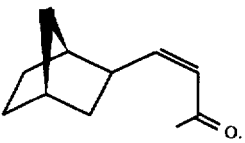

The peak indicated by reference numeral 122 is the peak for the compound having the structure:

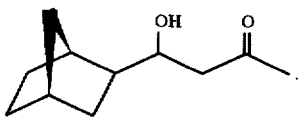

FIG. 16 is the GLC profile for the reaction product of Example II(B), Step 1. The peak indicated by reference numeral 160 is the peak for the compound having the structure:

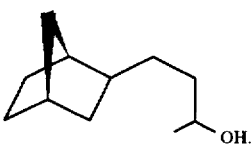

FIG. 18 is the GLC profile for the reaction product of Example II(B) Step 2. The peak indicated by reference numeral 180 is the peak for the compound having the structure:

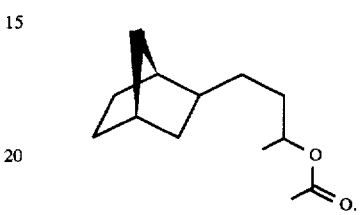

Referring to FIGS. 21 and 22, in particular, the apparatus used in producing polymeric fragrances containing at least one of the methyl-substituted 1(2-norbornyl) alkanol acetate esters of our invention comprises a device for forming scented polyolefin (for example) pellets which comprises a vat or container 212 into which a mixture of polyolefins such as polyethylene and an aromatic substance or scented material is placed (e.g., at least one of the methyl-substituted 1(2-norbornyl) alkanol acetate esters of our invention). The container is closed by an airtight lid 228 and clamped to the container by bolts 265. A stirrer 273 traverses the lid or cover 228 in an airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through a control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (e.g., at least one of the methyl-substituted 1(2-norbornyl) alkanol acetate esters of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (e.g., at least one of the methyl-substituted 1(2-norbornyl) alkanol acetate esters of our invention) is added to the polyolefin.

After the scent imparting material (e.g., a composition containing at least one of the methyl-substituted 1(2- norbornyl) alkanol acetate esters of our invention) is added to the container 212; the mixture is stirred for a few minutes, for example, 5–15 minutes; and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter, the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., at least one of the methyl-substituted 1(2-norbornyl) alkanol acetate esters of our invention) will continuously drop through orifices 234 downwardly from conduit 232. During this time, the temperature of the polymer (e.g., polyethylene or polyolefin) and scent imparting material (e.g., at least one of the methyl-substituted 1(2-norbornyl) alkanol acetate esters of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., at least one of the methyl-substituted 1(2-norbornyl) alkanol acetate esters of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 245 and utilized in processes as illustrated, infra.

A feature of this aspect of the process of our invention is the provision for moistening of the conveyor belt 238 to insure rapid formation of the solid polymeric (e.g., polyolefin) scented pellets 244 without sticking to material which will normally stick to a melted plastic. A moistening means 248 insures a sufficiently cold temperature of the belt surface for adequate formation of the pellets 244. The adequate mositening means comprises a container 250 which is continuously fed with water 254 to maintain a level for moistening a sponge element 256 which bears against the exterior of the belt 238.

THE INVENTION

We have determined that certain methyl-substituted 1(2-norbornyl) alkanol acetate esters defined according to the structures:

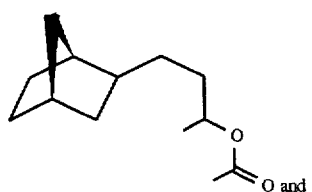

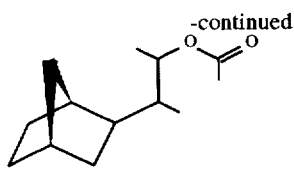

are capable of imparting a variety of fragrances to various consumable materials and are also capable of augmenting or enhancing a variety of fragrances of various consumable materials. Preferably, our invention is directed to:

(i) solely to the compound having the structure:

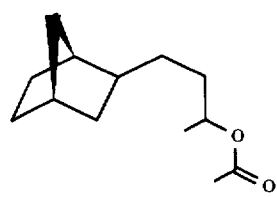

and its use in perfumery;

(ii) to the mixture of compounds having the structures:

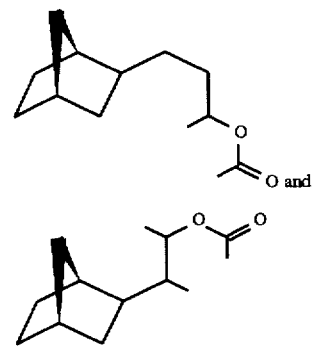

and the use of such mixture in perfumery;

(iii) the compounds having the structures:

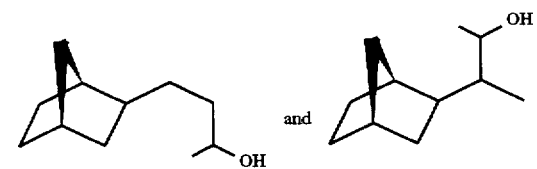

as intermediates for preparing the ester of (i) and (ii); and (iv) the chemical intermediates defined according to the structures:

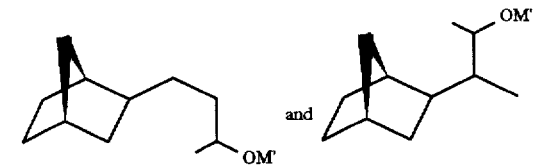

where M' represents MgX or Li and wherein X represents chloro, bromo or iodo.

Specifically, the genus having the structure:

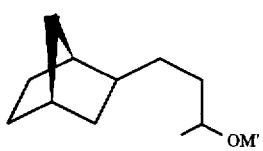

is intended to include the compound having the structure:

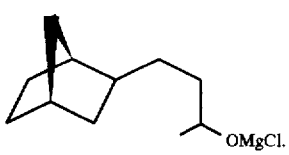

The genus having the structure:

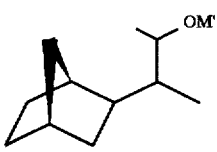

is intended to include the compound having the structure:

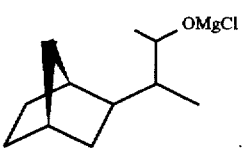

Our invention also includes the alkali metal salts defined according to the structure:

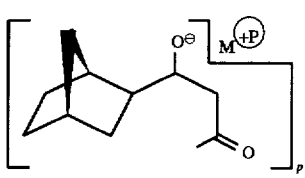

and also shown by the structure:

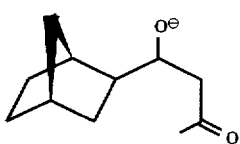

wherein M represents alkali metal, such as sodium or potassium or alkaline earth metal, such as barium; and P is the valence of M, for example, 2, in the case of M being barium.

It is contemplated that our invention also covers the stereoisomers of the compound having the structure:

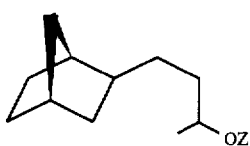

or mixtures of the compounds having the structures:

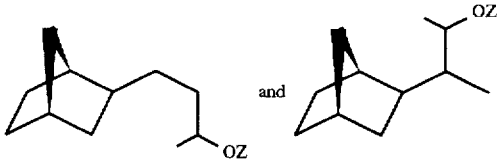

wherein Z is hydrogen or acetyl, to wit: the configurations having the structures:

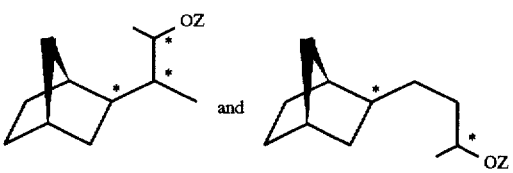

wherein the asterisks (*) are indicative of asymmetric carbon atoms. Thus, for example, it is contemplated that our invention covers the particular stereoisomer, to wit:

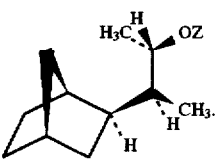

Briefly, our invention contemplates augmenting or enhancing the fragrances of consumable materials, such as perfumes, perfumed articles (e.g., solid or liquid anionic, cationic, nonionic or zwitterionic detergents, dryer-added fabric softeners and cosmetics) and colognes by adding thereto a small but effective amount of at least one of the methyl-substituted 1(2-norbornyl) alkanol acetate esters defined according to the structures:

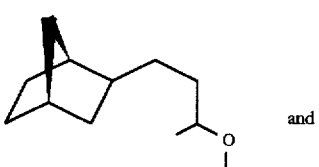

including but not limited to the single material having the structure:

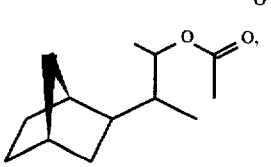

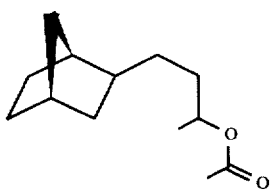

and mixtures of compounds having the structures:

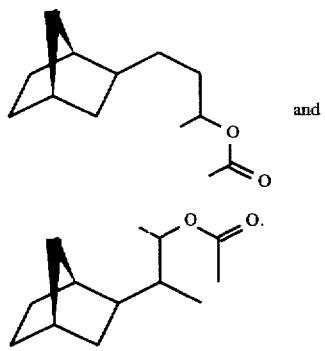

The methyl-substituted 1(2-norbornyl) alkanol acetate esters of our invention augment or enhance or impart seashore, ozoney, fruity, dry orange peel, bergamot and fatty aromas with rose, fatty, buttery, seashore and dry orange peel topnotes to perfumes, perfumed articles such as anionic, nonionic, cationic or zwitterionic detergents, dryer-added fabric softener articles, hair preparations and colognes.

The methyl-substituted 1(2-norbornyl) alkanol acetate esters of our invention can be produced using two routes. A first route will prepare a mixture of the compounds having the structures:

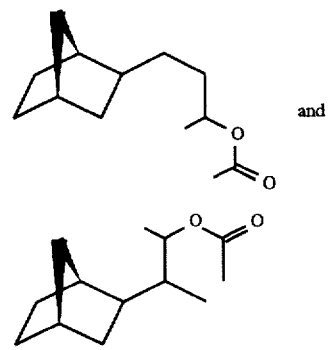

and the second route will only produce the compound having the structure:

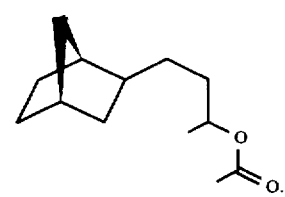

With respect to the route producing the mixture of compounds having the structures:

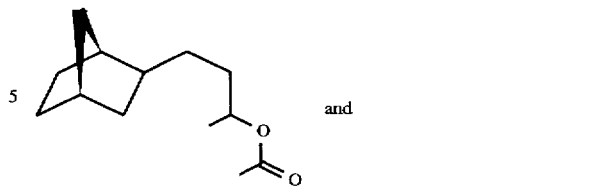

vinyl norbornene having the structure:

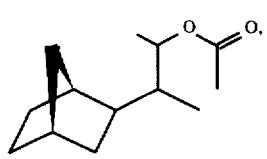

is used as a starting material. It is hydrogenated using a standard hydrogenation catalyst such as palladium on carbon or Raney nickel at a temperature in the range of from about 25° up to about 40° C. and at a pressure of less than about 50 pounds per square inch gauge according to the reaction:

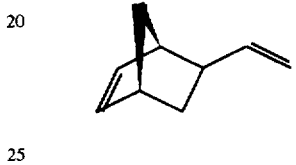

The resulting product having the structure:

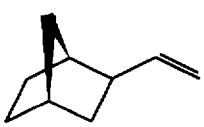

is then reacted with a mixture of carbon monoxide and hydrogen (via an "oxo" reaction) using a standard "oxo" reaction catalyst known to those skilled in the art, such as:

[RuCl₃·PCl₃].

The "oxo" reaction is carried out at a temperature in the range of 110°–120° C. and a pressure in the range of from about 500 up to about 700 psig. The reaction is shown thusly:

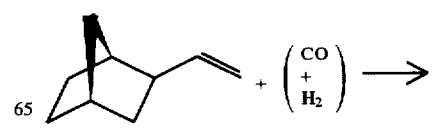

-continued

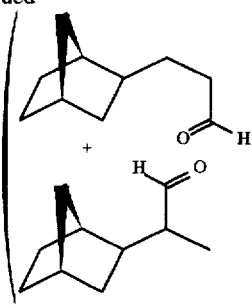

wherein in the resulting mixture, the ratio of the compound having the structure:

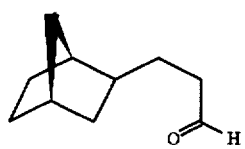

to the compound having the structure:

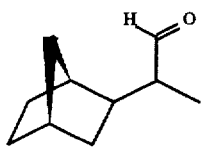

is about 85:15.

The resulting mixture of compounds having the structures:

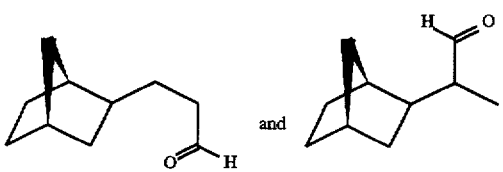

is then reacted via a Grignard reaction with the compound:

CH₃—M' which represents either methyl lithium or a methyl magnesium halide such as methyl magnesium chloride, methyl magnesium bromide or methyl magnesium iodide. The reaction is carried out under standard Grignard reaction conditions using a solvent such as diethyl ether, tetrahydrofuran or a mixture of tetrahydrofuran and toluene. The reaction is carried out at a temperature in the range of from about 30° up to 40° C., whereupon the organometallic compound mixture is formed which is a mixture of compounds having the structures:

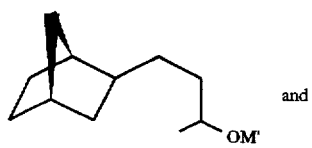

-continued

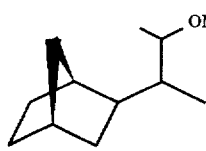

wherein M' represents Li or MgX and wherein X is chloro, bromo or iodo. The resulting mixture of compounds having the structures:

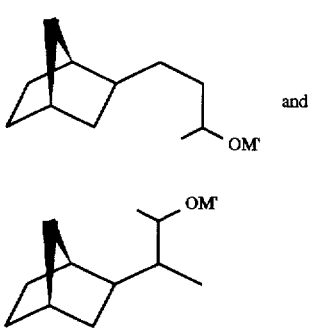

is then hydrolyzed in aqueous acid such as aqueous hydrochloric acid or aqueous acetic acid. The reaction sequence including the oxo reaction and subsequent Grignard reaction and hydrolysis reactions is set forth as follows:

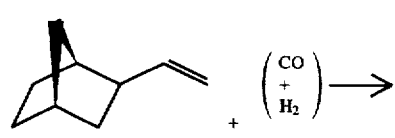

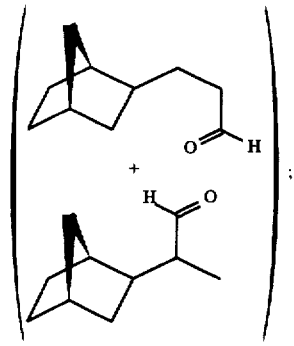

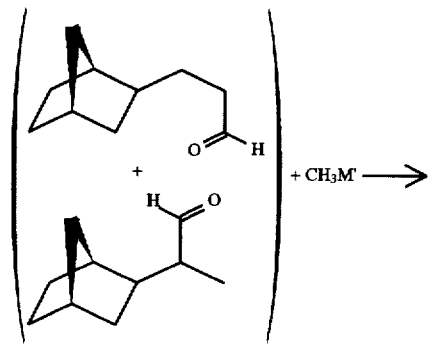

23
-continued
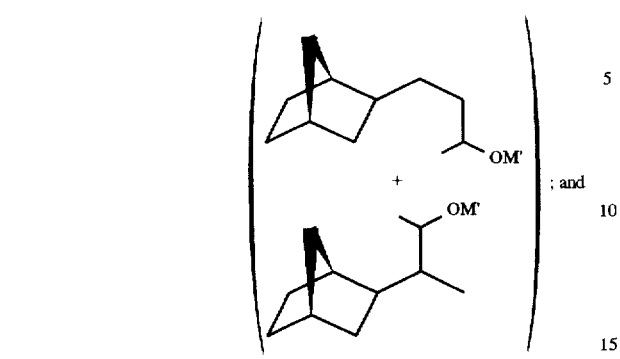; and
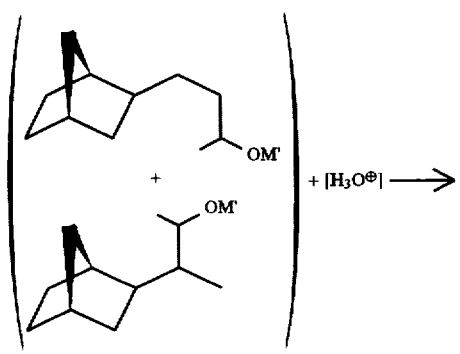 + [H₃O⁺] →
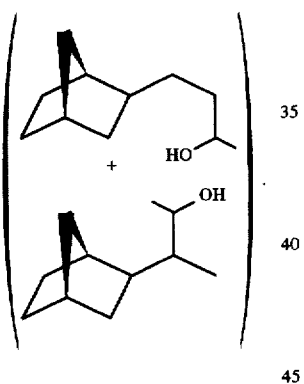
When using a methyl magnesium halide Grignard reagent, the Grignard reaction and subsequent hydrolyses are as follows:
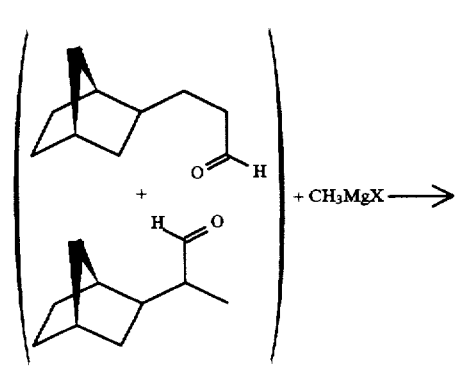 + CH₃MgX →
24
-continued
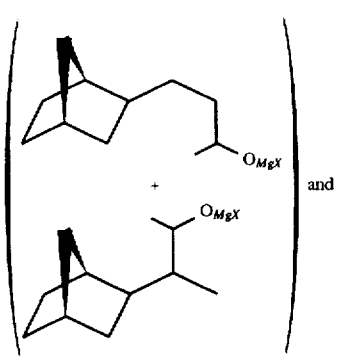 and
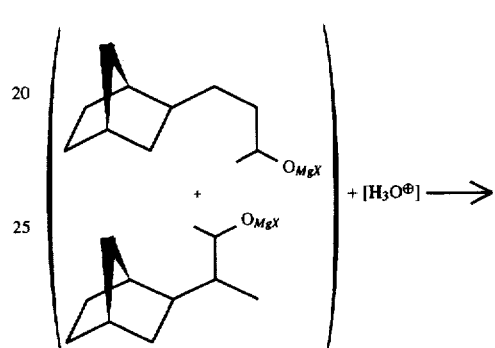 + [H₃O⁺] →
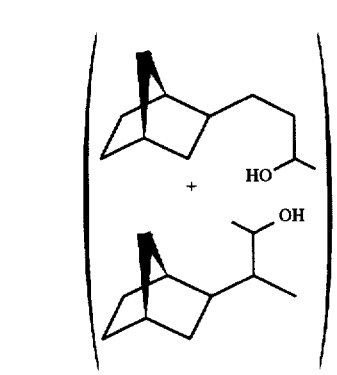
or, more specifically:
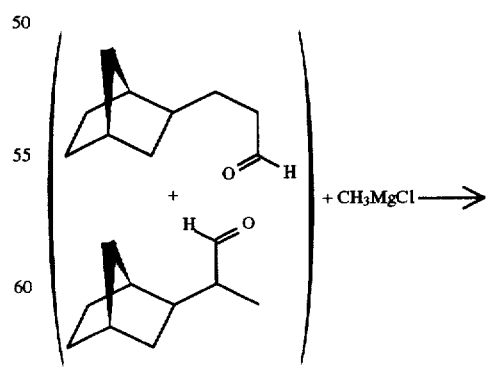 + CH₃MgCl →

25
-continued

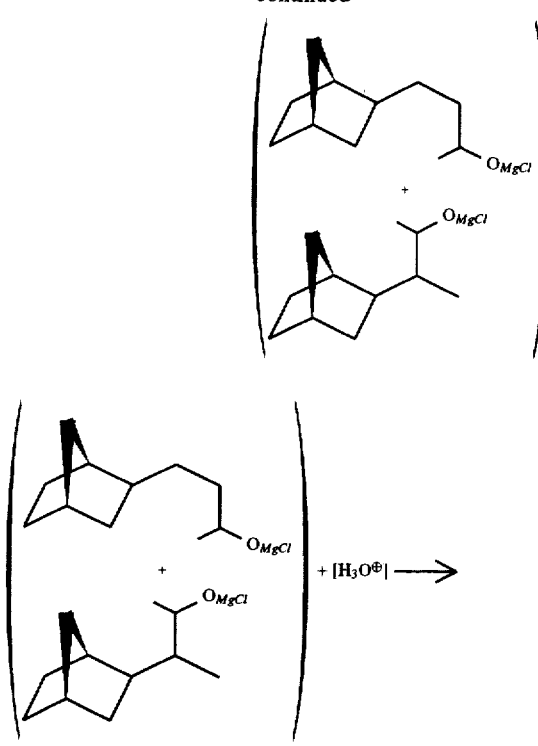

When using methyl lithium rather than a methyl magnesium halide, the reaction sequence is as follows:

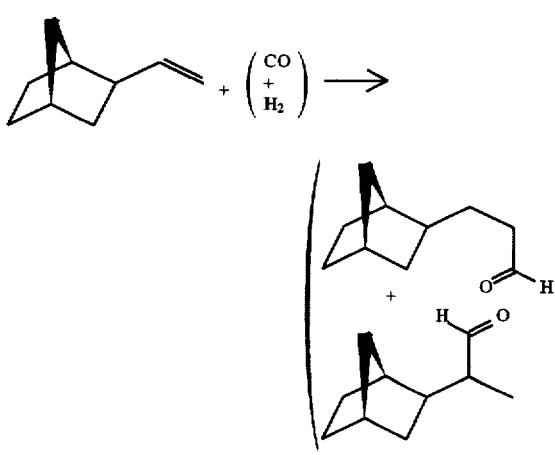

26
-continued

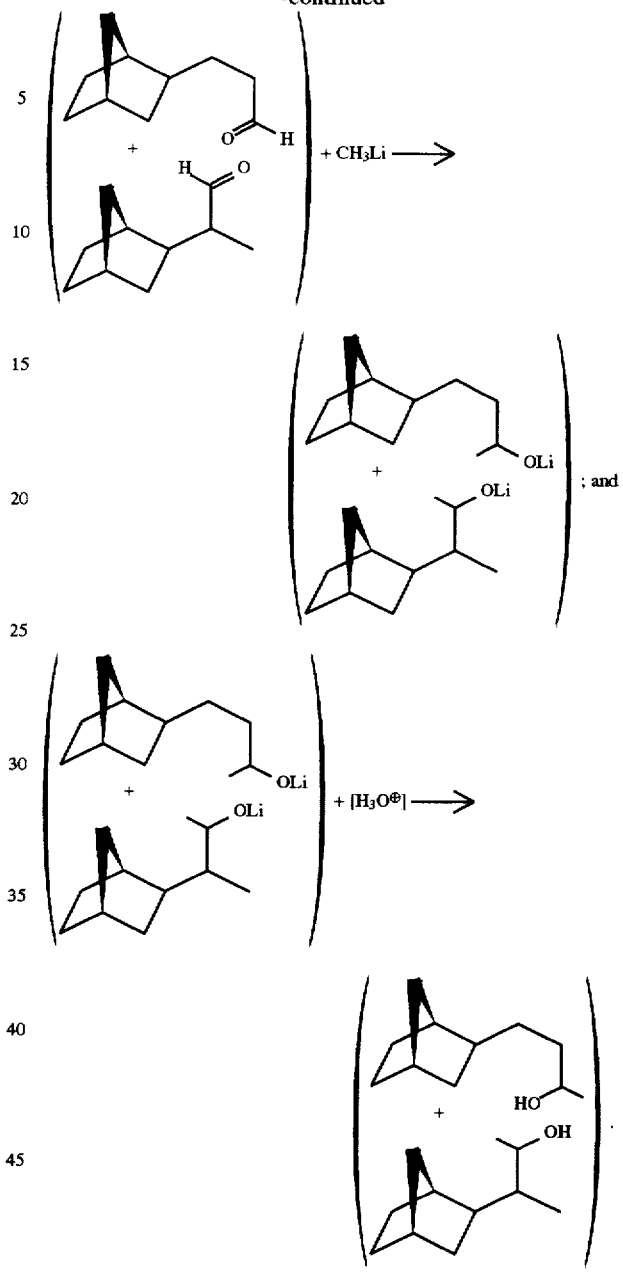

The resulting mixture of compounds having the structures:

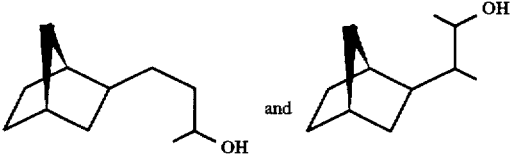

is then acetylated using standard acetylation reagents such as acetic anhydride or acetic acid in the presence of an acid catalyst. The treatment with the acetic anhydride or acetic acid is carried out under reflux conditions in the presence of a nonreactive solvent such as toluene. The mole ratio of acetylation reagent:alcohol reagent (mixture of compounds having the structures:

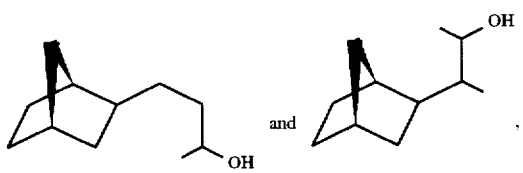 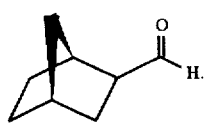

is about 1.2:1 (mole ratio). The time of reaction is between about 1 hour and about 5 hours. This acetylation reaction is shown thusly:

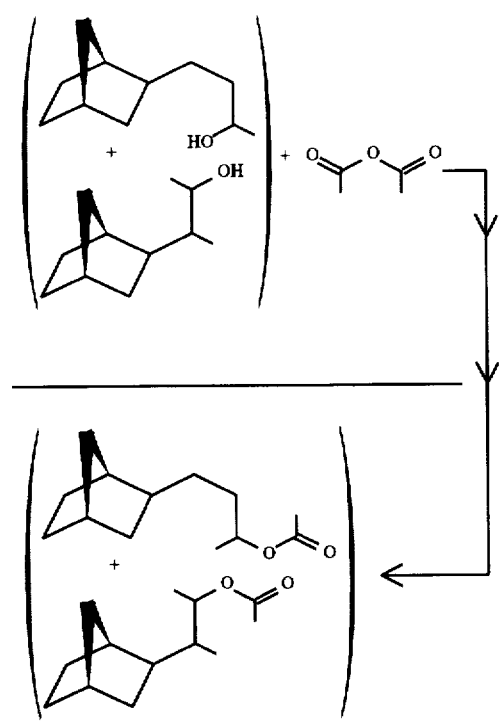

At the end of the reaction, the reaction mass is "worked up" by means of neutralization of the excess acetylating reagent using, for example, dilute aqueous sodium bicarbonate solution. The resulting product is fractionally distilled yielding product distilling at a vapor temperature of about 115° C. and a pressure of about 1.5 mm/Hg.

The second reaction sequence gives rise to the preparation of, solely, the compound having the structure:

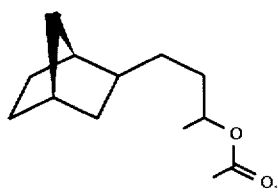

In this second reaction sequence, the starting material is the compound having the structure:

This compound is reacted with acetone under "aldol condensation" conditions according to the reaction:

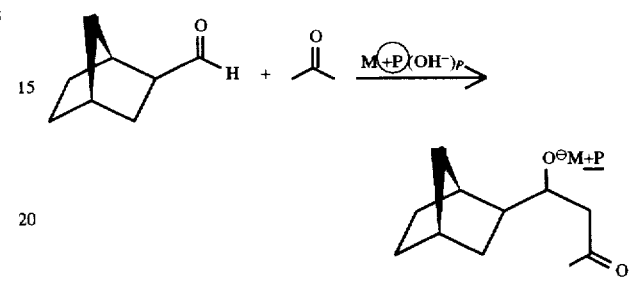

or according to the reaction:

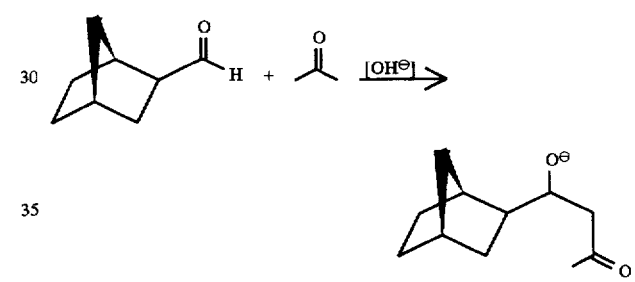

wherein M represents alkali metal or alkaline earth metal and P is the valence of the element indicated by M. Thus, for example, a useful base is barium hydroxide or barium oxide; however, sodium hydroxide and potassium hydroxide can also be used in order to catalyze the aldol condensation. The resulting salts shown by the structures:

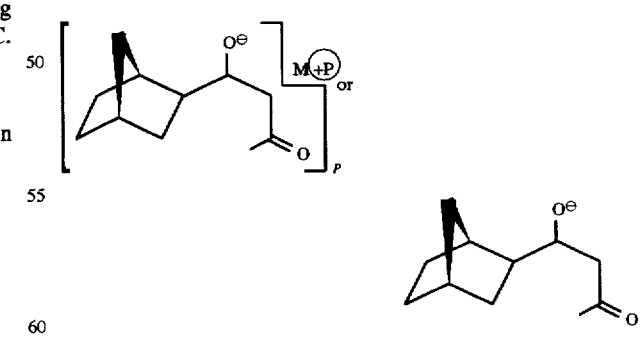

are novel materials. The resulting salts are then hydrolyzed in the presence of acid (and simultaneously dehydrated) to yield the mixture of ketones defined according to the structures:

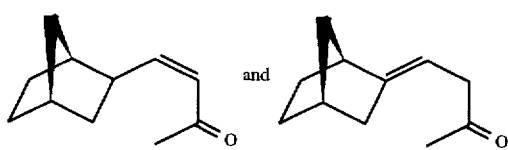

according to the reaction:

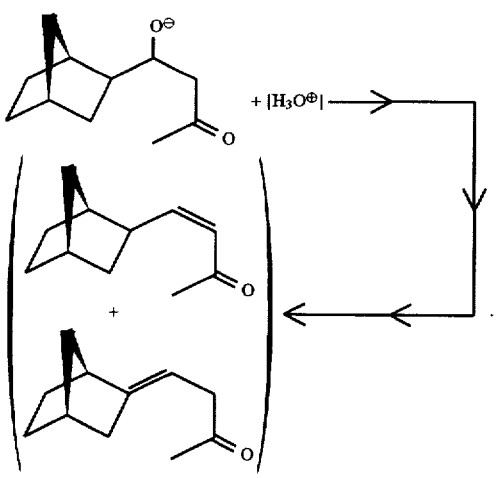

The reaction is carried out under reflux conditions for a period of between about 4 and about 10 hours. The weight ratio of base catalyst to reaction mass is between about 1:100 and about 1:300. The base, such as barium hydroxide, is used in the presence of water and the concentration of base in water is about 20–30 grams per liter. The resulting product containing the compounds having the structures:

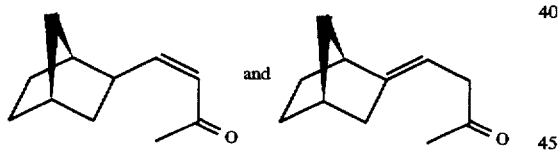

contains about 30% of the compound having the structure:

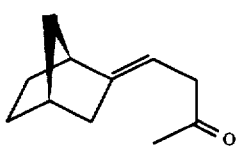

and about 70% of the compound having the structure:

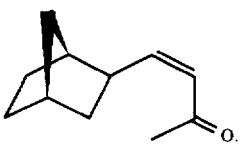

The resulting mixture of compounds shown thusly:

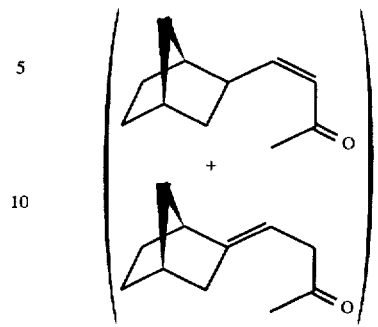

is then hydrogenated using a Raney nickel catalyst or copper chromite catalyst according to the reaction:

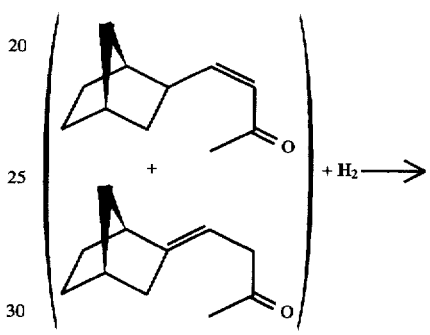

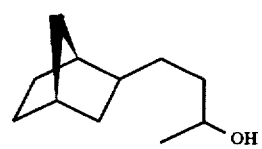

in order to yield the substantially pure alcohol having the structure:

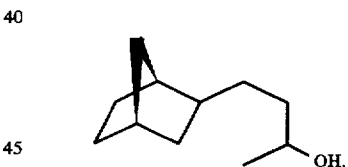

The hydrogenation reaction is carried out in the presence of an inert solvent such as isopropyl alcohol at a temperature of approximately 150° C. and at a pressure of approximately 500 psig. In place of isopropyl alcohol or in addition thereto, it is preferable to include toluene as a solvent. The weight ratio of copper chromite catalyst:mixture of compounds having the structures:

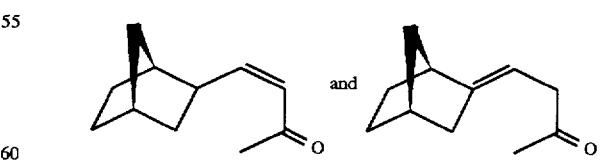

in this hydrogenation reaction may vary from about 1:100 up to about 2:100. The weight ratio of catalysts such as copper chromite catalyst:solvent (such as isopropyl alcohol) may vary from about 1:9 up to about 1:12.

At the end of the hydrogenation reaction, the reaction mass is "worked up" by means of appropriate washing and distillation. The resulting distillate is then reacted with an appropriate acetylation reagent, such as acetic anhydride or acetic acid in the presence of an acid catalyst, according to the reaction:

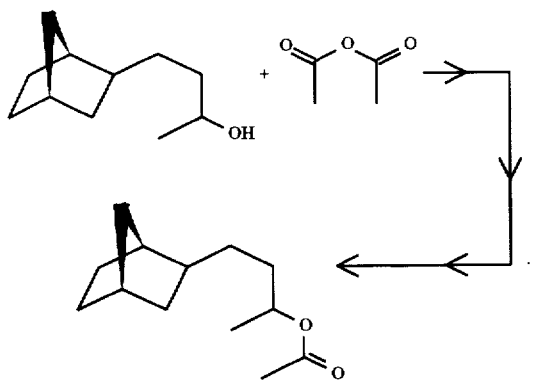

The resulting product is then "worked up" (whereby the excess acetylation reagent is neutralized with, for example, a dilute aqueous sodium carbonate solution) and is then fractionally distilled at a vapor temperature of about 100° C. and at a pressure of 0.8 mm/Hg.

Examples of the methyl-substituted 1(2-norbornyl) alkanol acetate esters of our invention and their organoleptic characteristics are as follows in Table I:

TABLE I

| Structure of Compound or Compounds | Fragrance Characteristic |
|---|---|
| The mixture of compounds having the structures: (structure shown) and (structure shown) prepared according to Example I(C), final distillation fraction 8. | A seashore, fruity, dry orange peel, bergamot, fatty aroma with rose, fatty, buttery, seashore and dry orange peel topnotes. |
| (structure shown) prepared according to Example II(B), bulked distillation fractions 2–10. | A seashore, ozoney aroma. |

Thus, the methyl-substituted 1(2-norbornyl) alkanol acetate esters of our invention can be used to contribute seashore, ozoney, fruity, dry orange peel, bergamot and fatty aromas with rose, fatty, buttery, seashore and dry orange peel topnotes to perfumes, perfumed articles and colognes.

As olfactory agents, the methyl-substituted 1(2-norbornyl) alkanol acetate esters of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils, esters other than the esters of our invention and frequently hydrocarbons which are admixed so that the combined odors of the individual components produce a pleasant or desired fragrance. Such perfume compositions usually contain: (a) the main note or the "bouquet" or foundation stone of the compositions; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of at least one of the methyl-substituted 1(2-norbornyl) alkanol acetate esters of our invention which will be effective in perfume compositions depends on many factors, including the other ingredients, their amounts and the effects which are desired. It has been found that perfume compositions containing as little as 0.5% of at least one of the methyl-substituted 1(2-norbornyl) alkanol acetate esters of our invention, or even less, can be used to impart interesting, long lasting and substantive seashore, ozoney, fruity, dry orange peel, bergamot and fatty aromas with rose, fatty, buttery, seashore and dry orange peel topnotes to soaps, liquid and solid anionic, nonionic, cationic or zwitterionic detergents, cosmetics, powders, liquid and solid fabric softeners, optical brightener compositions and other products. The amount employed can range up to 50% or higher and will depend on considerations of cost, nature of the end product, and the effect desired on the finished product and the particular fragrance sought.

The methyl-substituted 1(2-norbornyl) alkanol acetate esters of our invention can be used alone or in a perfume composition as an olfactory component in detergents and soaps; space odorants and deodorants; perfumes; colognes; toilet waters; bath salts; hair preparations such as lacquers, brilliantines, pomades and shampoos; cosmetic preparations such as creams, deodorants, hand lotions and sun screens; powders such as talcs, dusting powders, face powder and the like. When used as an olfactory component of a perfumed article, as little as 0.01% of one or more of the methyl-substituted 1(2-norbornyl) alkanol acetate esters of our invention will suffice to impart an interesting, long lasting and substantive seashore, ozoney, fruity, dry orange peel, bergamot and fatty aroma with rose, fatty, buttery, seashore and dry orange peel topnotes. Generally no more than 0.5% is required. Thus, the percentage in perfumed articles of the methyl-substituted 1(2-norbornyl) alkanol acetate esters of our invention ranges from 0.01% up to about 0.5% based on the weight of the perfumed article.

In addition, the perfume compositions of our invention can contain a vehicle or carrier for one or more of the methyl-substituted 1(2-norbornyl) alkanol acetate esters of our invention, taken alone or taken together with other ingredients. The vehicle can be a liquid such as an alcohol such as ethanol, a glycol such as propylene glycol or the like. The carrier can be an absorbent solid such as a gum or components for encapsulating the composition such as gelatin which can be used to form a capsule wall surrounding the perfume oil by means of coacervation.

It will thus be apparent that one or more of the methyl-substituted 1(2-norbornyl) alkanol acetate esters of our invention can be utilized to alter, modify, augment or enhance sensory properties, particularly organoleptic properties such as fragrances of a wide variety of consumable materials.

The following Examples serve to illustrate our invention, and this invention is to be considered restricted thereto only as indicated in the appended claims.

All parts and percentages given herein are by weight unless otherwise specified.

EXAMPLE I

Preparation of Mixture of α,β-Dimethyl-2-Norbornane Ethanol Acetate Ester and α-Methyl-2-Norbornyl Propanol Acetate Ester

EXAMPLE I(A)

Reactions:

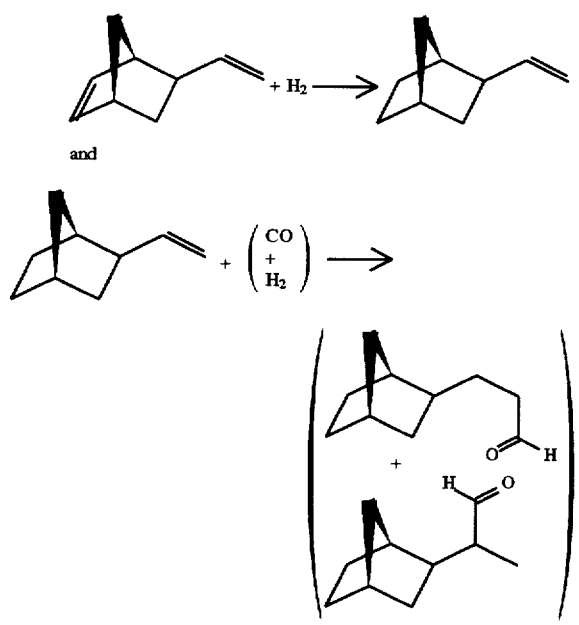

Into a 3 liter autoclave are placed 1,700 grams of vinyl norbornene having the structure:

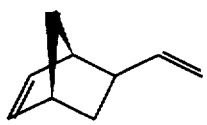

and 600 grams of a 5% palladium-on-carbon catalyst. The autoclave is equipped with a hydrogen feedline. The autoclave is sealed and pressurized with hydrogen to 100 psig. The hydrogenation is continued for a period of 2 hours while maintaining the temperature in the autoclave at 20°–25° C.

The autoclave is then depressurized and opened and the contents are filtered. The resulting product having the structure:

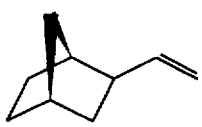

(weight: 1,582 grams) is then admixed with an oxo catalyst having the formula:

[RuCl₃·PCl₃]

(160 grams). The resulting mixture is then placed into a 3 liter autoclave equipped with carbon monoxide and hydrogen feedlines. Molar equivalent amounts of carbon monoxide and hydrogen are fed into the autoclave pressurizing the autoclave to 450 psig. The autoclave is maintained at a pressure of 450 psig and a temperature in the range of 75°–80° C. for a period of 5 hours.

At the end of the 5 hour period, the autoclave is cooled and opened and the product is filtered yielding 1,539 grams of product. The resulting product is fractionally distilled yielding the following fractions:

| Fraction Number | Vapor Temperature (°C.) | Liquid Temperature (°C.) | Vacuum mm/Hg Pressure | Reflux Ratio R/D | Weight of Fraction (grams) |
|---|---|---|---|---|---|
| 1 | 23/33 | 23/95 | 120/70 | 100 | 150 |
| 2 | 63 | 90 | 25 | 100 | 78 |
| 3 | 67 | 98 | 21 | 100 | 153 |
| 4 | 76 | 102 | 16 | 100 | 86.5 |
| 5 | 99 | 135 | 5 | 100 | 397 |
| 6 | 96 | 160 | 11 | 100 | 56 |

The resulting product contains the compounds having the structures:

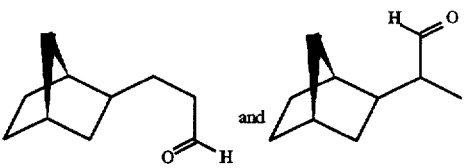

with the weight ratio of the compound having the structure:

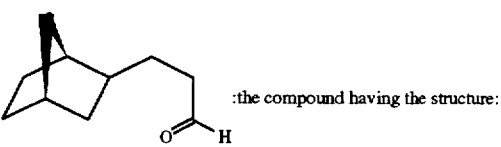

:the compound having the structure:

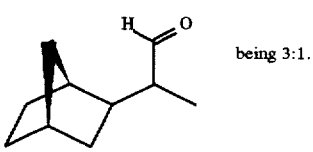

being 3:1.

EXAMPLE I(B)

Reaction:

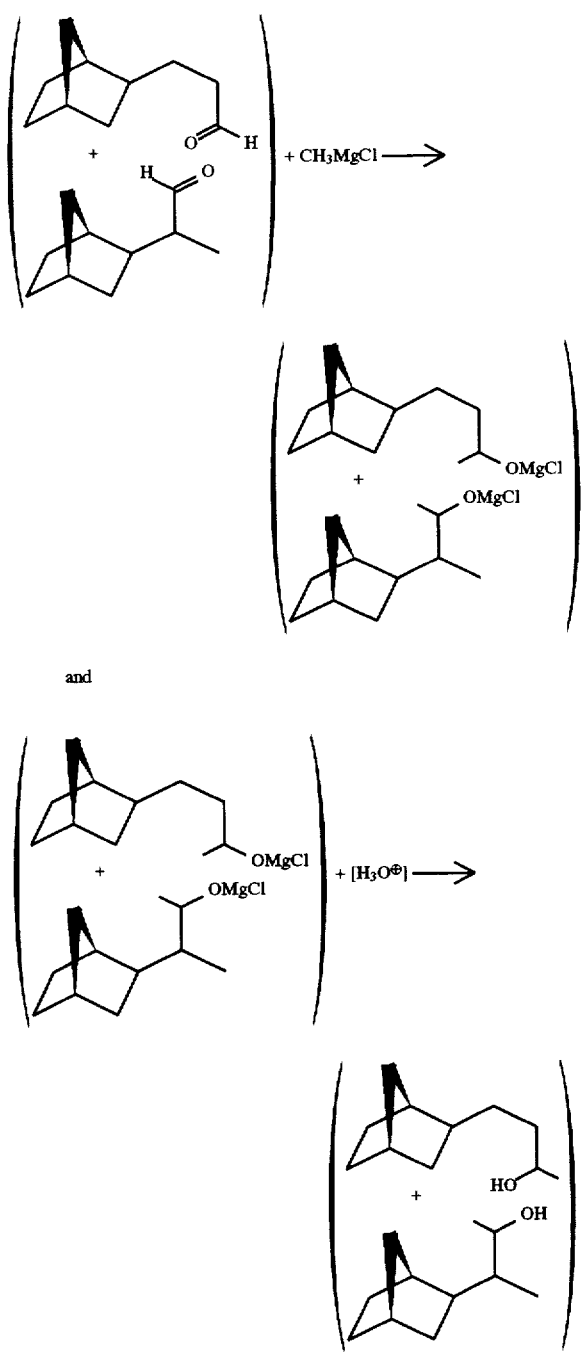

Into a 3 liter reaction vessel equipped with stirrer, thermometer, reflux condenser and heating mantle, are placed a solution of 800 ml of 3M methyl magnesium chloride (2.4 moles of methyl magnesium chloride). Over a period of 2 hours while maintaining the reaction mass at a temperature of 30°–40° C., 330 grams (2.2 moles) of the mixture of compounds having the structures:

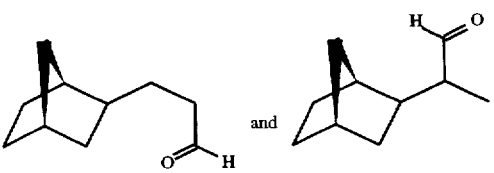

prepared according to Example I(A) are added to the reaction mass with stirring. Over a period of 2 hours, the reaction mass is permitted to "exotherm" at 30°–40° C.

The reaction mass, at this point, now contains the compounds having the structures:

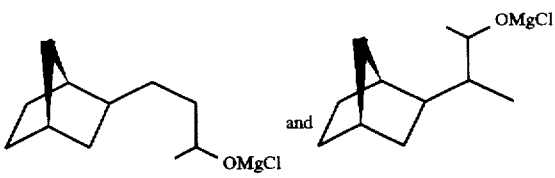

The reaction mass is now quenched into 180 grams of acid in 800 grams of ice.

The reaction mass now exists two phases: an organic phase and an aqueous phase. The organic phase is separated from the aqueous phase and the organic phase is washed with an equal volume of 10% aqueous sodium carbonate solution. 300 Ml toluene is added to the resulting mixture. The resulting organic phase is then fractionally distilled yielding the following fractions:

| Fraction Number | Vapor Temperature (°C.) | Liquid Temperature (°C.) | Vacuum mm/Hg Pressure | Reflux Ratio R/D | Weight of Fraction (grams) |
|---|---|---|---|---|---|
| 1 | 23/34 | 23/110 | 150/40 | 100 | 287 |
| 2 | 105 | 116 | 4 | 4:1 | 28 |
| 3 | 105 | 116 | 3 | 4:1 | 26 |
| 4 | 106 | 116 | 3 | 4:1 | 32 |
| 5 | 105 | 117 | 3 | 4:1 | 22 |
| 6 | 106 | 116 | 3 | 4:1 | 28 |
| 7 | 107 | 118 | 3 | 4:1 | 21 |
| 8 | 107 | 119 | 3 | 4:1 | 23 |
| 9 | 105 | 118 | 2 | 4:1 | 32 |
| 10 | 103 | 122 | 2 | 4:1 | 24 |
| 11 | 102 | 133 | 1 | 4:1 | 24 |
| 12 | 97 | 167 | 1 | 4:1 | 19 |

Fractions 2–9 are then bulked for subsequent reaction in Example I(C). The resulting product is a mixture of compounds having the structures:

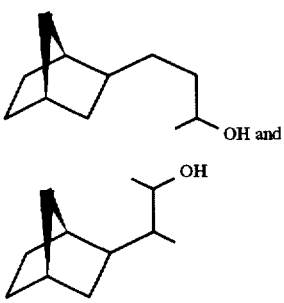

with the mole ratio of the compound having the structure:

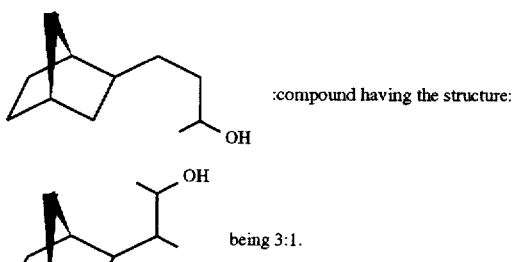

:compound having the structure:

being 3:1.

EXAMPLE I(C)

Reaction:

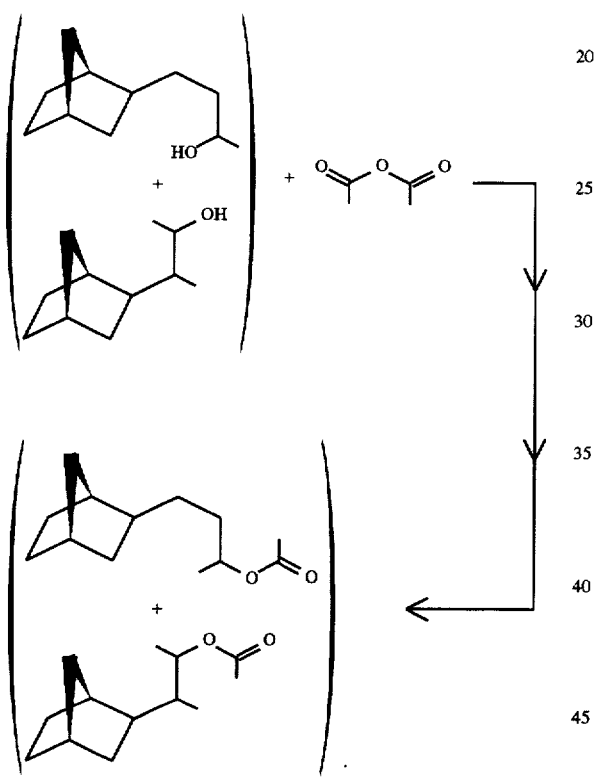

Into a 1 liter reaction vessel equipped with stirrer, thermometer, heating mantle and reflux condenser are placed the following materials:

(i) 220 grams of bulked distillation fractions 2–9 of Example I(B) containing the compounds having the structures:

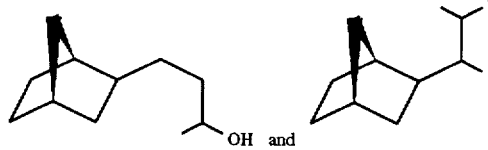

(1.3 moles);
(ii) 168 grams of acetic anhydride (1.65 moles); and
(iii) 100 ml anhydrous toluene.

The resulting mixture is refluxed to 136° C. and maintained at reflux for a period of 1 hour.

At the end of the 1 hour period, the reaction mass is quenched with 300 ml water. The resulting product contains two phases: an organic phase and an aqueous phase. The organic phase is then washed with 1 liter of a 5% aqueous sodium carbonate solution (pH=8.5).

The resulting product is then fractionally distilled yielding the following fractions:

| Fraction Number | Vapor Temperature (°C.) | Liquid Temperature (°C.) | Vacuum mm/Hg Pressure | Reflux Ratio R/D | Weight of Fraction (grams) |
|---|---|---|---|---|---|
| 1 | 23 | 23 | 120 | 100 | 90 |
| 2 | 114 | 119 | 1 | 4:1 | 23 |
| 3 | 45 | 119 | 1.5 | 4:1 | 27 |
| 4 | 45 | 119 | 1.5 | 4:1 | 28 |
| 5 | 115 | 119 | 1.5 | 4:1 | 31 |
| 6 | 115 | 119 | 1.5 | 4:1 | 29 |
| 7 | 115 | 121 | 1.5 | 4:1 | 27 |
| 8 | 115 | 120 | 1.5 | 4:1 | 27 |
| 9 | 115 | 120 | 1.5 | 4:1 | 30 |
| 10 | 118 | 124 | 1.5 | 4:1 | 26 |
| 11 | 118 | 145 | 1.5 | 4:1 | 28 |
| 12 | 111 | 200 | 1.0 | 4:1 | 17 |

Fractions 2–10 are bulked. Fraction 8 containing the compounds having the structures:

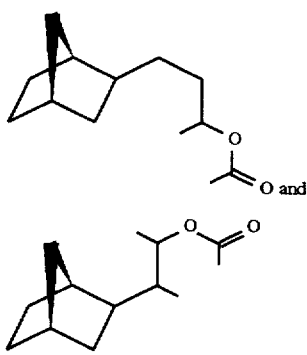

has an intense and substantive seashore, fruity, dry orange peel, bergamot and fatty aroma with rose, fatty, buttery, seashore and dry orange peel topnotes.

EXAMPLE II

Preparation of α-Methyl-2-Norbornyl Propanol Acetate Ester

EXAMPLE II(A)

Reactions:

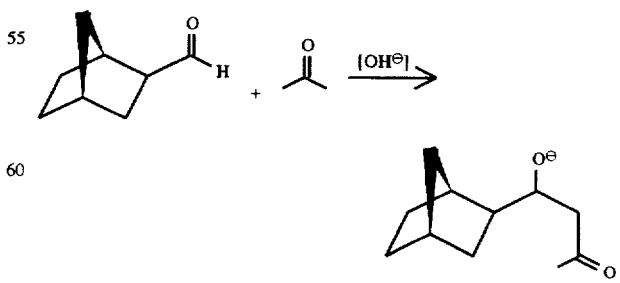

and

-continued

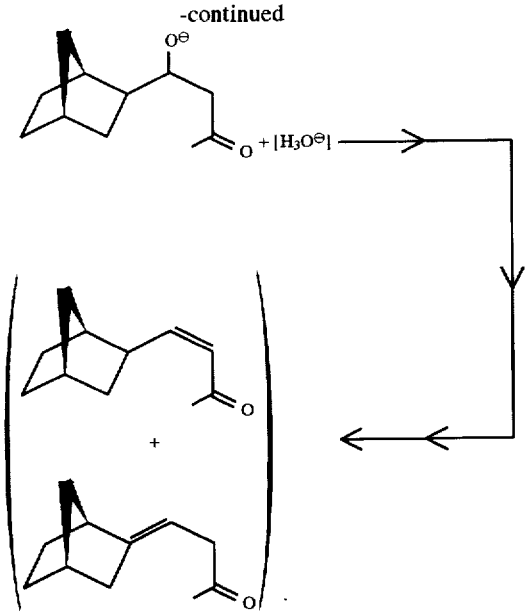

Into a 3 liter reaction vessel equipped with reflux condenser, thermometer, heating mantle and addition funnel are placed the following materials:

(i) 1,950 grams acetone;
(ii) 440 ml water; and
(iii) 10 grams barium hydroxide.

The resulting mixture is heated to reflux. Over a period of 2 hours, 826 grams (5.0 moles) of the compound having the structure:

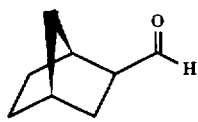

is added to the reaction mass. The reaction mass is continued to be refluxed for a period of 5 hours.

At the end of the reaction, the excess acetone is distilled from the reaction mass. The resulting product has the structure:

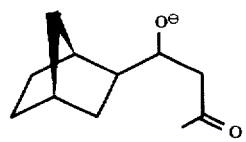

(which can also be shown as the structure:

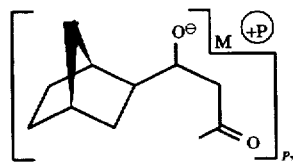

wherein M is Ba and P is the number "2").

The resulting product is then admixed with an equal volume of 20% hydrochloric acid. The resulting product now exists in two phases: an organic phase and an aqueous phase. The organic phase is separated from the aqueous phase. The organic phase is washed, consecutively, with:

(i) an equal volume of water; and (ii) an equal volume of 5% aqueous sodium bicarbonate.

The resulting product is then fractionally distilled yielding the following fractions:

| Fraction Number | Vapor Temperature (°C.) | Liquid Temperature (°C.) | Vacuum mm/Hg Pressure | Weight of Fraction (grams) |
|---|---|---|---|---|
| 1 | 23/44 | 23/90 | 150/25 | 208 |
| 2 | 48 | 95 | 1.0 | 57 |
| 3 | 48 | 105 | 1.0 | 44 |
| 4 | 109 | 122 | 0.8 | 342 |
| 5 | 110 | 125 | 0.7 | 72 |
| 6 | 45 | 185 | 0.7 | 341 |

Fraction 5 (the middle fraction) is redistilled to yield 12 fractions. Fractions 2–9 thereof contain 30% by weight of the compound having the stucture:

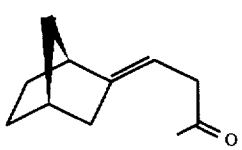

and 70% by weight of the compound having the structure:

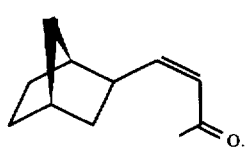

Fractions 2–9 distill at 110° C. vapor temperature and 0.7 mm/Hg pressure.

EXAMPLE II(B)

Reactions:

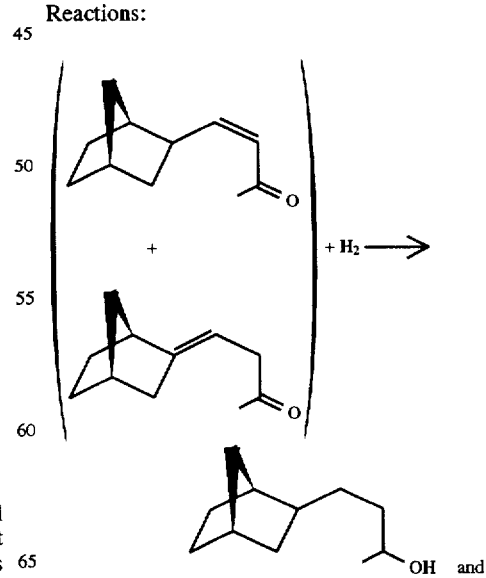

-continued

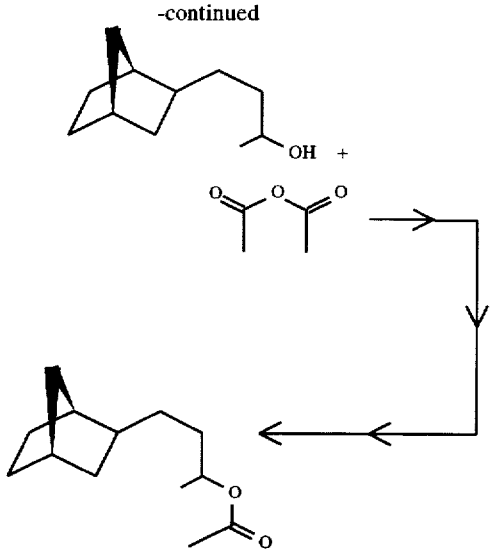

Into a 1 liter autoclave equipped with hydrogen feedline are placed:

(i) 400 grams of the mixture of compounds having the structures:

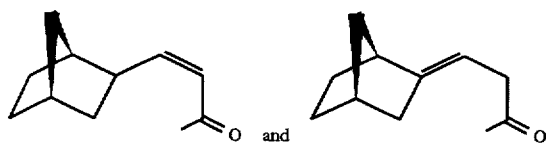

prepared according to Example II(A);

(ii) 60 grams of anhydrous isopropyl alcohol; and (iii) 5.0 grams copper chromite catalyst.

The autoclave is pressurized to 500 psig with hydrogen and maintained at a temperature of 150° C. for a period of 4 hours. At the end of the 4 hour period, the autoclave is cooled to room temperature and opened and 5.0 grams of Raney nickel is added thereto. The autoclave is then closed and repressurized with hydrogen to 500 psig and maintained at 500 psig at a temperature of 150° C. for 5 hours.

At the end of the additional 5 hour period, the autoclave is cooled and opened. The resulting product is filtered. The resulting filtrate weighing 390 grams is then admixed with 300 grams of acetic anhydride and 150 ml toluene. The resulting mixture is then placed into a reaction vessel equipped with stirrer, thermometer, reflux condenser and heating mantle. The resulting mixture is heated to reflux (132° C.) and maintained at reflux for a period of 1 hour. At the end of the 1 hour period, the reaction mass is cooled and quenched with 500 ml water.

The resulting product now exists in two phases: an organic phase and an aqueous phase. The organic phase is separated from the aqueous phase and washed with one equal volume of 5% aqueous sodium carbonate solution (pH=8.2).

The resulting product is then fractionally distilled yielding the following fractions:

| Fraction Number | Vapor Temperature (°C.) | Liquid Temperature (°C.) | Vacuum mm/Hg Pressure | Reflux Ratio R/D | Weight of Fraction (grams) |
|---|---|---|---|---|---|
| 1 | 23/38 | 23/100 | 150/30 | 100 | 185 |
| 2 | 101 | 117 | 1.5 | 9:1 | 21 |
| 3 | 91 | 107 | 0.9 | 9:1 | 26 |
| 4 | 96 | 108 | 0.9 | 9:1 | 25 |
| 5 | 98 | 108 | 0.9 | 9:1 | 23 |
| 6 | 99 | 108 | 0.8 | 9:1 | 22 |
| 7 | 100 | 109 | 0.8 | 9:1 | 19 |
| 8 | 100 | 110 | 0.8 | 4:1 | 21 |
| 9 | 100 | 111 | 0.8 | 4:1 | 23 |
| 10 | 100 | 112 | 0.8 | 4:1 | 24 |
| 11 | 100 | 114 | 0.8 | 4:1 | 27 |
| 12 | 100 | 115 | 0.7 | 4:1 | 22 |
| 13 | 101 | 116 | 0.7 | 4:1 | 23 |
| 14 | 103 | 117 | 0.7 | 4:1 | 21 |
| 15 | 103 | 118 | 0.7 | 4:1 | 20 |
| 16 | 103 | 121 | 0.7 | 4:1 | 22 |
| 17 | 105 | 126 | 0.7 | 4:1 | 24 |
| 18 | 110 | 133 | 0.7 | 4:1 | 26 |
| 19 | 135 | 153 | 0.7 | 4:1 | 21 |
| 20 | 136 | 155 | 0.6 | 4:1 | 20 |
| 21 | 138 | 170 | 0.6 | 4:1 | 19 |
| 22 | 119 | 195 | 0.5 | 4:1 | 11 |

Fractions 2–10 are bulked. Bulked distillation fractions 2–10 have a seashore and ozoney aroma. Bulked distillation fractions 2–10 is the substantially pure compound having the structure:

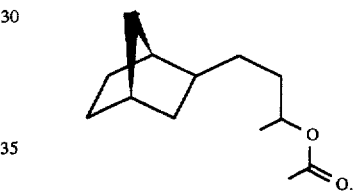

The methyl-substituted 1(2-norbornyl) alkanol acetate esters of our invention can be used alone or can be admixed with other seashore aroma nuance imparting materials, such as picoline derivatives defined according to the structure:

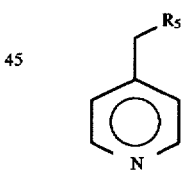

wherein $R_5$ represents myrcenyl, geranyl, 1-cyclohexenyl, 2-cyclohexenyl or 3-cyclohexenyl.

EXAMPLE III

Herbal/"Seashore" Fragrance Formulation

The following mixtures are prepared:

| Ingredients | Parts by Weight | | | |
|---|---|---|---|---|
| | III(A) | III(B) | III(C) | III(D) |
| Amyl cinnamic aldehyde | 20 | 20 | 20 | 20 |
| Phenyl acetaldehyde dimethyl acetyl | 4 | 4 | 4 | 4 |
| Thyme oil white | 8 | 8 | 8 | 8 |
| Sauge sclaree French | 8 | 8 | 8 | 8 |

43
-continued

| Ingredients | Parts by Weight | | | |
|---|---|---|---|---|
| | III(A) | III(B) | III(C) | III(D) |
| Galbanum oil | 4 | 4 | 4 | 4 |
| Juniper berry oil | 10 | 10 | 10 | 10 |
| Methyl octin carbonate | 4 | 4 | 4 | 4 |
| Linalyl acetate | 2 | 2 | 2 | 2 |
| Dihydro methyl jasmonate | 10 | 10 | 10 | 10 |
| Cis-3-hexcenyl acetate | 12 | 12 | 12 | 12 |
| The mixture of compounds having the structures: | 12 | 0 | 12 | 12 |

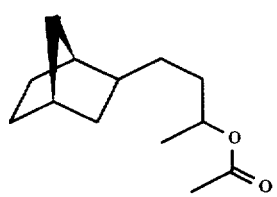

and

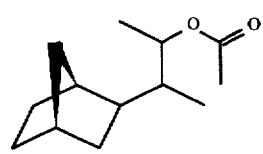

prepared according to Example I(C), distillation fraction 8.

| The compound having the structure: | 0 | 12 | 0 | 12 |

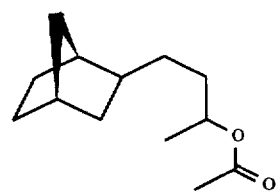

prepared according to Example II(B), bulked distillation fractions 2-10.

| The compound having the structure: | 0 | 0 | 12 | 12 |

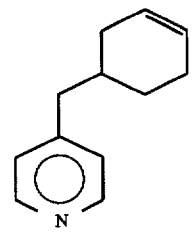

The mixture of compounds having the structures:

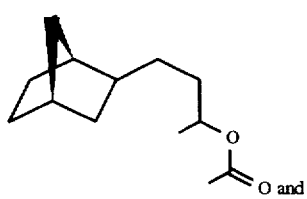

-continued

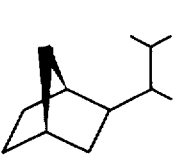

produced according to Example I(C) imparts to this herbal formulation, seashore, fruity, dry orange peel, bergamot and fatty undertones with rose, fatty, buttery, seashore and dry orange peel topnotes. Accordingly, the perfume composition of Example III(A) can be described as having:

"An herbal aroma with seashore, fruity, dry orange peel, bergamot and fatty undertones with rose, fatty, buttery, seashore and dry orange peel topnotes".

The compound having the structure:

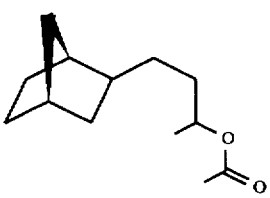

prepared according to Example II(B) imparts to this herbal fragrance formulation, seashore and ozoney undertones. Accordingly, the fragrance formulation of Example III(B) is described as having:

"An herbal aroma with seashore and ozoney undertones".

The compound having the structure:

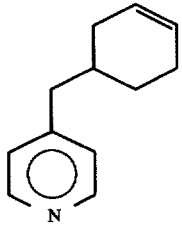

adds additional, intense "fresh salt air" undertones to each of the formulations of Examples III(C) and III(D). Accordingly, the formulation of Example III(C) can be described as having:

"An herbal aroma with seashore, fresh salt air, fruity, dry orange peel, bergamot and fatty undertones with rose, fatty, buttery, seashore and dry orange peel topnotes".

The aroma of Example III(D) can be described as having:

"An herbal aroma with seashore, fresh salt air, ozoney, fruity, dry orange peel, bergamot and fatty undertones with rose, fatty, buttery, seashore and dry orange peel topnotes".

EXAMPLE IV

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| The mixture od compounds having the structures: [structure 1] and [structure 2] produced according to Example I(C). | A seashore, fruity, dry orange peel, bergamot and fatty aroma with rose, fatty, buttery, seashore and dry orange peel topnotes. |
| [structure 3] prepared according to Example II(B). | A seashore and ozoney aroma. |
| Perfume composition of Example III(A). | An herbal aroma with seashore, fruity, dry orange peel, bergamot and fatty undertones with rose, fatty, buttery, seashore and dry orange peel topnotes. |
| Perfume composition of Example III(B). | An herbal aroma with seashore and ozoney undertones. |
| Perfume composition of Example III(C). | An herbal aroma with seashore, fresh salt air, fruity, dry orange peel, bergamot and fatty undertones with rose, fatty, buttery, seashore and dry orange peel topnotes. |
| Perfume composition of Example III(D). | An herbal aroma with seashore, fresh salt air, ozoney, fruity, dry orange peel, bergamot and fatty undertones with rose, fatty, buttery, seashore and dry orange peel topnotes. |

EXAMPLE V

Perfumed Liquid Detergents

Concentrated liquid detergents (lysine salt of n-dodecylbenzene sulfonic acid as more specifically described in U.S. Pat. No. 3,948,818 issued Apr. 6, 1976, incorporated by reference herein) with aroma nuances as set forth in Table II of Example IV are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentrations of substance as set forth in Table II of Example IV.

EXAMPLE VI

Preparation of Cologne and Handkerchief Perfumes

Compositions as set forth in Table II of Example IV, are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example IV are imparted to the colognes and to the handkerchief perfumes at all levels indicated.

EXAMPLE VII

Preparation of a Soap Composition

100 Grams of soap chips (per sample) (IVORY® produced by the Procter & Gamble Company of Cincinnati, Ohio) are each mixed with 1 gram samples of substances as set forth in Table II of Example IV until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example IV.

EXAMPLE VIII

Preparation of Solid Detergent Compositions

Detergents are prepared using the following ingredients according to Example I of Canadian Patent No. 1,007,948 (incorporated by reference herein):

| Ingredient | Parts by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I of column 15 of U.S. Pat. No. 3,632,396 (the disclosure of which is incorporated herein by reference), non-woven cloth substrates useful as dryer-added fabric softening articles of manufacture are prepared wherein the substrate, the substrate coating, the outer coating and the perfuming material are as follows:

1. a water "dissolvable" paper ("Dissolvo Paper");
2. Adogen 448 (m.p. about 140° F.) as the substrate coating; and 3. an outer coating having the following formulation (m.p. about 150° F.):

57% $C_{20-22}$ HAPS;
22% isopropyl alcohol;
20% antistatic agent; and
1% of one of the perfume materials as set forth in Table II of Example IV.

Fabric softening compositions prepared according to Example I at column 15 of U.S. Pat. No. 3,632,396 having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener, non-woven fabrics and these aroma characteristics are described in Table II of Example IV.

EXAMPLE X

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| Ingredient | Weight Percent |
| --- | --- |
| Dioctyl sebacate | 0.05 |
| Benzyl alcohol | 0.10 |
| Dow Corning 473 fluid prepared by the Dow Corning Corporation | 0.10 |
| TWEEN ® 20 surfactant (prepared by ICI America Corporation) | 0.03 |
| One of the perfumery substances as set forth in Table II of Example IV | 0.10 |

The perfuming substances as set forth in Table II of Example IV add aroma characteristics as set forth in Table II of Example IV which are rather intense and aesthetically pleasing to the users of the soft-feel, good-hold pump hair sprays.

What is claimed is:

1. A compound defined according to structure:

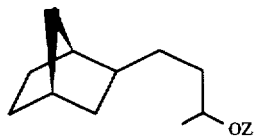

wherein Z represents hydrogen or acetyl.

2. The mixture compounds having the structures:

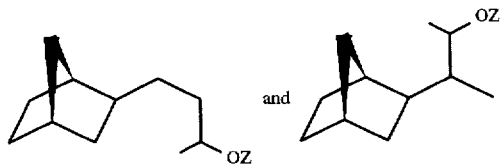

wherein Z represents hydrogen or acetyl.

3. The compound of claim 1 wherein Z is acetyl.
4. The mixture of claim 2 wherein Z is acetyl.
5. The compound having the structure:

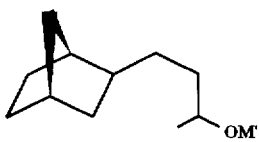

wherein M' represents MgX or Li and wherein X is chloro, bromo or iodo.

6. The mixture of compounds having the structures:

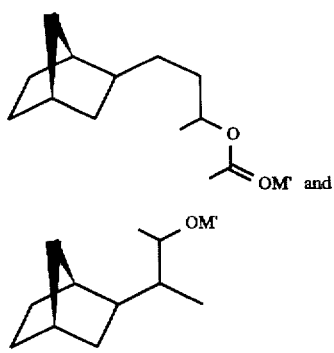

wherein M' represents MgX or Li and wherein X is chloro, bromo or iodo.

7. A perfume composition comprising a perfume base and intimately admixed therewith an aroma augmenting, enhancing or imparting quantity and concentration of the compound of claim 3.

8. A perfume composition comprising a perfume base and intimately admixed therewith an aroma augmenting, enhancing or imparting quantity and concentration of the mixture of claim 4.

9. A perfumed article comprising a perfumed article base and intimately admixed therewith an aroma augmenting, enhancing or imparting quantity and concentration of the compound of claim 3.

10. A perfumed article comprising a perfumed article base and intimately admixed therewith an aroma augmenting, enhancing or imparting quantity and concentration of the mixture of claim 4.

11. A cologne comprising water, ethanol and an aroma imparting quantity of the compound of claim 3.

12. A cologne comprising ethanol, water and an aroma imparting quantity of the mixture of claim 4.

13. A perfumed polymer comprising a microporous polymer and intimately admixed therewith and in the interstices thereof an aroma imparting quantity of the compound of claim 3.

14. A perfumed polymer comprising a microporous polymer and intimately admixed in the interstices thereof an aroma imparting quantity of the mixture of claim 4.

15. The mixture of the compound of claim 3 and the compound having the structure:

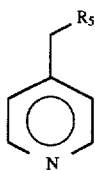

wherein $R_5$ represents myrcenyl, geranyl or cyclohexenyl.

16. A mixture comprising the mixture of claim 4 and the compound having the structure:

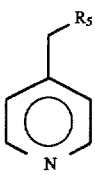

wherein $R_5$ represents myrcenyl, geranyl or cyclohexenyl.

17. A perfume composition comprising a perfume base and intimately admixed therewith an aroma agumenting, enhancing or imparting quantity and concentration of the composition of claim 15.

18. A cologne comprising water, ethanol and an aroma imparting quantity and concentration of the mixture of claim 15.

19. A perfumed article comprising a perfumed article base and intimately admixed therewith an aroma augmenting, enhancing or imparting quantity and concentration of the composition of claim 15.

20. A perfumed polymer comprising a microporous polymer and intimately admixed therewith in the interstices thereof an aroma imparting quantity of the composition of claim 15.

21. A process for augmenting, imparting or enhancing an aroma in or to a consumable material selected from the group consisting of perfumed articles, perfume compositions, colognes and perfumed polymers comprising the step of intimately admixing with said consumable material an aroma imparting, augmenting or enhancing quantity and concentration of the compound of claim 3.

22. A process for augmenting, enhancing or imparting an aroma in or to a consumable material comprising intimately admixing with said consumable material an aroma augmenting, enhancing or imparting quantity and concentration of the mixture of claim 4.

23. A process for augmenting, enhancing or imparting an aroma in or to a consumable material comprising intimately admixing with said consumable material an aroma augmenting, enhancing or imparting quantity and concentration of the mixture of claim 15.

24. A process for augmenting, enhancing or imparting an aroma in or to a consumable material comprising intimately admixing with said consumable material an aroma augmenting, enhancing or imparting quantity and concentration of the mixture of claim 16.

25. A perfume composition comprising a perfume base and intimately admixed therewith an aroma agumenting, enhancing or imparting quantity and concentration of the composition of claim 16.

26. A cologne comprising water, ethanol and an aroma imparting quantity and concentration of the mixture of claim 16.

27. A perfumed article comprising a perfumed article base and intimately admixed therewith an aroma augmenting, enhancing or imparting quantity and concentration of the composition of claim 16.

28. A perfumed polymer comprising a microporous polymer and intimately admixed therewith in the interstices thereof an aroma imparting quantity of the composition of claim 16.

29. A salt defined according to the structure:

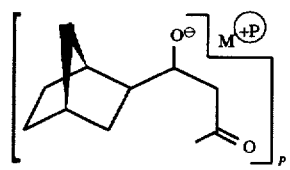

wherein M represents an alkali metal ion or an alkaline earth metal ion and wherein P is the valence of M.

30. The compound of claim 29 wherein M is barium ion and P is +2.

* * * * *